US011242572B2

(12) United States Patent
Wang et al.

(10) Patent No.: US 11,242,572 B2
(45) Date of Patent: Feb. 8, 2022

(54) IMMUNOGENIC CEDAR VIRUS COMPOSITIONS

(71) Applicant: The Henry M. Jackson Foundation for the Advancement of Military Medicine, Inc., Bethesda, MD (US)

(72) Inventors: Linfa Wang, Wandana Heights (AU); Glenn A. Marsh, Leopold (AU); Hume Field, Ormiston (AU); Christopher Broder, Silver Spring, MD (US)

(73) Assignee: THE HENRY M. JACKSON FOUNDATION FOR THE ADVANCEMENT OF MILITARY MEDICINE, INC., Bethesda, MD (US)

( * ) Notice: Subject to any disclaimer, the term of this patent is extended or adjusted under 35 U.S.C. 154(b) by 0 days.

(21) Appl. No.: 16/351,380

(22) Filed: Mar. 12, 2019

(65) Prior Publication Data

US 2020/0123623 A1 Apr. 23, 2020

Related U.S. Application Data

(63) Continuation of application No. 15/180,544, filed on Jun. 13, 2016, now Pat. No. 10,227,664, which is a continuation of application No. 14/412,533, filed as application No. PCT/US2013/049069 on Jul. 2, 2013, now abandoned.

(60) Provisional application No. 61/667,194, filed on Jul. 2, 2012.

(51) Int. Cl.

| | |
|---|---|
| ***A61K 39/12*** | (2006.01) |
| ***C07K 14/005*** | (2006.01) |
| ***C07K 16/10*** | (2006.01) |
| ***C12N 7/00*** | (2006.01) |
| ***C12Q 1/70*** | (2006.01) |
| *A61K 39/00* | (2006.01) |

(52) U.S. Cl.

CPC .............. *C12Q 1/701* (2013.01); *A61K 39/12* (2013.01); *C07K 14/005* (2013.01); *C07K 16/1027* (2013.01); *C12N 7/00* (2013.01); *C12Q 1/70* (2013.01); *A61K 39/00* (2013.01); *A61K 2039/543* (2013.01); *C07K 2317/76* (2013.01); *C12N 2760/18221* (2013.01); *C12N 2760/18222* (2013.01); *C12N 2760/18231* (2013.01); *C12N 2760/18234* (2013.01); *C12Q 2600/136* (2013.01)

(58) Field of Classification Search

None

See application file for complete search history.

(56) References Cited

U.S. PATENT DOCUMENTS

| | | | |
|---|---|---|---|
| 2006/0053501 | A1 | 3/2006 | Courbot et al. |
| 2007/0031455 | A1 | 2/2007 | Audonnet |
| 2016/0362755 | A1 | 12/2016 | Wang et al. |

FOREIGN PATENT DOCUMENTS

| | | | |
|---|---|---|---|
| WO | 2010/039778 | A2 | 4/2010 |

OTHER PUBLICATIONS

Abubakar et al., Nipah Virus, Complete Genome, Isolate NV/MY/99NRI-2794, GenBank Accession Version: AJ564621.1 [database online] Apr. 15, 2005, [retrieved on Feb. 13, 2014 http://blasl.ncbi.nlm.nih.gov/Blasl.cgi].

Chan et al., Nipah Virus Isolate UMMC1, Comlete Genome, Gen Bank Accession Version: AY029767 .1 [database online] Sep. 7, 2001 [retrived on Feb. 14, 2014 http://blasl.ncbi.nlm.nih.cov/Blasl.cgi].

Marsh et al., Cedar Virus Isolate CG1a, Complete Genome, GenBank Accession Version: JQ001776.1 [database online] Aug. 19, 2012 [retrived on Feb. 13, 2014 http://blasl.ncbi.nlm.nih.cov/Blasl.cgi].

Marsh et al., "Cedar Virus: A Novel Henipavirus Isolated From Australian Bats," PLoS Pathogenes, 8 (8):1-11 (2012).

Persaud et al., Pol Protein [Human Immunodeficiency Virus], GenBank Accession Version: ADY92592.1 [database online] Aug. 11, 2011 [retrived on Feb. 13, 2014 http://blasl.ncbi.nlm.nih.cov/Blasl.cgi].

International Search Report issued in PCT/US2013/049069, dated Mar. 4, 2014.

*Primary Examiner* — Nicole Kinsey White

(74) *Attorney, Agent, or Firm* — Foley & Lardner LLP

(57) ABSTRACT

The present disclosure is directed towards a virus, called Cedar Virus, and its methods of use.

12 Claims, 13 Drawing Sheets

Specification includes a Sequence Listing.

A. LEADER AND TRAILER REGIONS OF THE ANTIGENOME SEQUENCE

| | |
|---|---|
| CedPV | 5′-ACCAGAAAAAGG.....CCTTTTTTAGGA-3′ |
| HeV | 5′-ACCGAACAAGGG.....CCCTTGTTCGGA-3′ |
| NiV | 5′-ACCAAACAAGGG.....CCCTTGTTCGGA-3′ |

B. SEQUENCE OF INTERGENIC REGIONS (IGR) AND TRANSCRIPTIONAL START AND STOP SIGNALS

| GENES | GENE START | IGR | GENE STOP |
|---|---|---|---|
| /N | | CTT | AGGATCCCGG |
| N/P | TTACAAAAAA | CTT | AGGATCCAAG |
| P/M | TTAGAAAAAA | CTT | AGGATCCCAG |
| M/F | TTAAGAAAAA | CTT | AGGATCCCAG |
| F/G | TTAAATAAAA | CTT | AGGATCCCAG |
| G/L | TTAAAGAAAA | CTT | AGGATCCCAG |
| L/ | TTAAAGAAAA | CTT | |

CONSENSUS

| | | | |
|---|---|---|---|
| CedPV | TTAvrdAAAA | CTT | AGGATCCmrG |
| HeV | TTAmrDAAAA | CTT | AGGAnmCArG |
| NiV | TwAwrDAAAA | CTT | AGGAnmCArG |

FIG. 2

SEQUENCE LISTING

<160> NUMBER OF SEQ ID NOS: 16

<210> SEQ ID NO 1
<211> LENGTH: 18162
<212> TYPE: DNA
<213> ORGANISM: Cedar virus

<400> SEQUENCE: 1
accagacaaa ggaagtctag tctccggatt aaatcatatt cgtatgatta atcttaggat 60
cccggtatct agaatctgga tctggattcg gtttaattga attgcgatcg tttataaatt 120
agaaaggaga tttactactc aaaatgtctg acattttcaa tgagactcaa tcatttagaa 180
actatcagtc caacttaggc agagatggca gggccagtgc agcaacgact actttgacaa 240
ctaaagtgag gatctttgtt ccagcgaata ataatccaaa cctcagatgg cgtttaacac 300
tattcttgat ggatgtcgtg aggtcacctg cctccgcaga gtctatgaaa gtgggtgctg 360
ggatatcctt ggtatctatg tatgctgaaa aacccggggc tcttgtgaga gcattattga 420
atgacccaga tgttgaagcg ataatcatag atgtttatgg ctttgatgaa ggtattccta 480
taatggaacg aagaggtgat aaagctacag atgacatgga ttccctaaga aagattgtta 540
aagctgcaca tgatttcagc agaggaagga gtttatttgt tgatcaaagg gtccaggata 600
ttgttatgtc agatatgggg tcatttgtga atgctattac ttccatagag acgcagatat 660
ggattttgat cgcaaaggct gtaactgccc cagatacagc agaagagagc gaaggaagaa 720
gatgggcaaa atatgttcag caaaagaggg ttaatccttt gttcttgatt tctccacaat 780
ggatcaatga catgagatcc ctgattgcgg caagtctttc gcttcgtaaa ttcatggttg 840
aactactgat ggaagctaag aaaggacggg ggacaaaagg aagaataatg gagattgtat 900
ccgatatcgg aaattacgtt gaagagacag gaatggcagg gttcttcgct acaataaagt 960
tcggtcttga gaccaaattc cctgctttgg cacttaatga gctccagagt gacttgaaca 1020
caatgaaaag tctcatgata ctgtacagaa gcataggacc aaaggccccc tttatggtgt 1080
tgttggaaga ttcaattcag accaaatttg ctccaggaag ctatccactt ctttggagtt 1140
ttgcgatggg tgtaggcaca actattgaca gagctatggg tgccttgaac attaacagaa 1200
gttatcttga acctgtctat tttaggctag ggcaacaatc agctaaacat caagcaggaa 1260
atgttgacaa agaaatggca gaaaagttag gattgacaga agaccagatc gtgcacctat 1320
cagctaatgt gaaggatgca agtcaaggta gagatgacaa tcaaatcaac atccgagaag 1380
ggaagttcac aaatgttgtt gatgacatcc aggatcatgc ccagagttcc tctgaggatt 1440
acaatcctag taaaaagagt ttctcaatat tgacgagcat cacatccacc gtagatagtg 1500
ctgacagtag gtctgcaatg aatgagtcaa tgacaacaac atccttgctg aaattgagac 1560
agaggctggc agagaagaaa ggagactcca agaacagtca agacacacct ccaaaaccac 1620
ccagagcaaa agatcaaccc actgatgagg tctccttcat ggattccaat atatgatcag 1680
aatgatggtt aaaatcaacc aactaagggc gcgtagagta ccttcagata gaacactaca 1740
ttaatcgggt gaaacaatag atttatgggt ttggtgctta atttttattt aatcttactt 1800
gcaaaacagg cagctgctac actcgtaacc actcctcaca gtaagggcaa cacgggtcat 1860
agaacttatg cctatagatt acctctatct gtatatctag ctatgattaa aatgtatact 1920
tctgctgacc ggttttctag caacagtcca cattattact ttatgggtat tttttaatca 1980
accttttata atcaaatata ttacaaaaaa cttaggatcc aagtggtcca aacttttttt 2040
gatcaagagt catattggct actttaggag gacactttaa acacaaattg ttacaagagg 2100

-continued

```
atattcatca gatggacaaa ctacaattga ttgaagatgg cctctctact atcaatttta   2160
tacaggaaaa taaggaaaaa ttacagcatt cttacggaag atcctccatc agagagccac   2220
ccacaagtgt cagggttgaa gagtgggaga aatttattcg aaagatcgct tctggacctg   2280
aacaagttca agggggagga tctgagactg agatcacagg cgataatgga gatagaggca   2340
attttaccaa tcctgatcag ggaggcggag tcacaggaca attcgaagaa aggtatcaaa   2400
aatgggggtc acaagattca gaattacaac tggacccaat ggttgtacac gatttcttct   2460
atgacgagag aagggagaat cccgacaatg gaaaatatga ccgcagctct aaaaaacggg   2520
ataatatcag agaaggaaca cgacaggata agtacaataa tcagtctact gatgaattac   2580
tgtcctgcct acaaccatct tctaagaacg atgtcatcaa gaatgaaagt acatcagtgt   2640
caaatttgca tgttacagga aataaactga atcctgacgc aaaacccttt gaacccacct   2700
cccagtcgaa agagcaccca accaccacac agcacaacaa aaatgaccat cagaccgatg   2760
atgattataa gaatagaaga tccagtgaaa acaatgtgat ctctgatcat gccaccacaa   2820
tggaagacaa caacaatttt atcccggcga ccaaaagaaa gaatgcattg agcgaaccca   2880
tatacgtcca ggtattgccc tcaaacacag agggtttctc gggaaaagat tatccactcc   2940
tcaaggacaa ctctgtcaag aagcgtgcag agccagtcat cctagaaact gccaaccacc   3000
ctgcaggctc tgccgaccaa gacacaaatc agattgaaga aaacatgcag ttcaaccttc   3060
caaaactgct cacagaagat acagacgatg aaccagagga taacaatgat tccatgcctc   3120
ttgaggaaga cattagagag atcggttcca tgctaaaaga tggaaccaaa gatatcaaga   3180
caaggatgaa tgagatagat gacgcaatca agaagataaa taagaaatca aaaaatagaa   3240
gtctggatct agaatcagac ggtaaagatc aggggagaag agatccatca gtagacctcg   3300
ggattaaaaa aagaaaggaa gggctaaagg ccgcaatgca aaagacaaaa gagcaattgt   3360
ctataaaagt ggagagagag attggattga acgacaggat atgtcaaaat tcgaagatga   3420
gtacagaaaa gaaattgata tatgctggga tggaaatgga gtatggacaa acgagtactg   3480
ggtcaggagg tccacaagga tcaaaggatg ggacttctga tgatgtccag gtagacgaag   3540
actacgatga aggggaagac tatgaggcta tgccgtcaga taggttttat acaacattat   3600
caggtgaaca aaaggataga tttgatctag atgctaacca aatgtctcag tatgacctcg   3660
aggcccaggt ggatgaatta accagaatga atctcatact ctattctaga ttagaaacta   3720
ctaataagtt gcttattgac atattagatc tagctaaaga aatgccaaag ttagttagaa   3780
aagtggataa tcttgagaga cagatgggta acttgaatat gttaacctct acccttgagg   3840
gtcacctatc ttctgtaatg attatgatac ccggtaagga taagagcgaa aaggaaatcc   3900
ctaaaaatcc ggacctgaga ccaatactgg ggagaagcaa cacgtcgtta actgatgtta   3960
tcgacctaga ccattaccct gataaaggct ccaaaggtat caaaccaagt ggatctggag   4020
acagacagta catcggctct ctagagagca aattttctat aaatgatgag tacaattttg   4080
ctccataccc tatcagggac gaactcctat tgccaggttt aagagatgac aaaaccaatg   4140
cttcatcgtt catcccagat gacacggaca ggtctccaat ggtgctcaaa ataataattc   4200
gacagaacat ccatgatgaa gaagtgaagg atgagctact gtccatacta gaacaacata   4260
acactgtgga ggaattgaat gaaatatgga atactgtgaa tgattacctc gatggcaaca   4320
tctgattaac agatattgag attgatccta ttctaaacaa gtaatctctg ataatgatag   4380
tatggaataa gaatactaat cacactattg tactcttgta gaatcttaac gagtgtctaa   4440
```

-continued

```
tgtcagattt tagcaacaca tactaataac ttgtaatcca tttctcctta ttccatttaa   4500
tctcacatta gaaaaaactt aggatcccag atttgcaaag tcaaaacggg atctactatc   4560
aggtgttgga gctaacaata gcggagtctg cataacaaat agcgttcaaa gaagtttgaa   4620
aaccatcata gaatatggat ccgtcagatt tgaggaggat tataatggag gatgataaga   4680
gtctggtcaa caatgatgat agtacagaaa ctgattttct cgagaaaact tggagagaag   4740
ggagtaagat tgacaagatc acaccagagg ttgatgaaaa cgggaatatg gtccccaagt   4800
acgttgtctt caacccgggg aaaaatgaga ggaaaacatc cggatatcaa tatatgattt   4860
gttatggttt cattgaggat ggacctatca atggctcacc aagagtcaaa ggtaatatca   4920
gaaccaccgc ttcttttcct ttgggtgttg gaaaaactta ctcgtctcca gaagagatct   4980
tacaagagct gacaacactc aagatcactg tcagaaggac agccggatca aatgagaagt   5040
tggtgtatgg aataacaggg cctttaaatc acctttaccc gtggtataaa gttttgacag   5100
gtggctccat ttttagtgcg gtgaaggtct gtaggaatgt ggatcaaata ctattagaca   5160
gaccccaaat acttagagta ttctttctaa gtataactaa attaacagat aaaggtgtgt   5220
atatgatacc caaaagtgtt ctcgacttca gatcggataa ttcgatggcc ttcaatctgc   5280
ttgtgtatct caagatagac actgacatca ccaaagcagg catcagaggg attgtcaaca   5340
aagaagggga gaggataacg tcattcatgt tacacatcgg taactttaca agaagaggag   5400
gaaaacatta ctcagtggag tattgcaaaa ggaaaattga caaaatgaag ctcacattcg   5460
ccttaggcac tataggcggt ctaagcttac atatcaggat cgatggaagg ataagtaaaa   5520
ggctccaagc acaagttggc tttcagagaa acatttgcta ctcactaatg gacacaaacc   5580
catggttgaa taaattaacg tggaacaata gttgtgaaat acacaaagtc accgctgtca   5640
ttcagccatc tgtgccaaag gacttcatgt tgtatgagga catcttaata gataatacag   5700
gcaagatctt aaaataaagt aggagagtca gtcattaccc agtatattga atactaatga   5760
caactttatt aatccaattc tatctccagt tactagaatt tctaaaacaa ttctactgct   5820
cagcaacgca tctcaaacat tgtgatcttc aattatgatc gacgcattgt aatctatata   5880
gcttttagtt catgaaatac taaaaagggc ttaatcttgt aagttctcag caaatactcc   5940
aatgcaaaag agcgcctcaa catctcaagc agcaccaaaa taaaccacaa tcaatgtgca   6000
acaagagcaa tcgtctaaag tgtgaaaacc aaaatcacag atcagaaagg gcacatattt   6060
cagtcctgta aaaataccaa gtgggattaa taaaagagga tcaatcctta tcattttaag   6120
aaaaacttag gatcccagag atcctaaaga gccaattcct ttatattttg atcttgaagg   6180
gctagaagtc aggctgaaac acagaggtgg aggaacacag gaactaaaat tgatgaaatc   6240
aaccttagct caacatctaa tcaatcaagc ttaagtcatc ctaatactgt atacaaccag   6300
cagcgtagag agtggatttg atttcggcac ccttgcgaag tgaaggctat tactgcctgt   6360
cctttcaatc agaaaattac atttacccat aaagtaatct caacatgtct aacaagagga   6420
caacagtatt gatcataata agctatacgt tattttattt gaataatgca gcaattgtag   6480
ggtttgattt tgataaattg aataaaatag gtgtggtgca agggagagtc ctaaattata   6540
aaattaaagg agatccaatg acaaaagacc ttgtcttgaa atttatccct aacatagtga   6600
atatcactga atgtgtgaga gagcccttga gtaggtacaa tgagaccgtg aggagattgc   6660
ttttacctat acacaacatg cttgggttat acttgaataa cacaaatgct aaaatgactg   6720
ggttgatgat cgcgggtgtg atcatgggtg ggatagcaat aggtatagcc acagcagctc   6780
agatcacagc aggttttgct ctttatgagg caaaaaagaa cacagaaaat attcagaaat   6840
```

-continued

```
taacagacag catcatgaaa acacaggact cgattgataa acttactgac agtgtgggga   6900
caagcatact tatattgaat aagctacaga catacatcaa caatcaactg gtaccaaatc   6960
tagagcttct atcctgccga caaaacaaaa ttgagtttga tctaatgtta accaagtatt   7020
tggtggatct tatgactgtt attggtccta atatcaataa tcctgttaat aaagatatga   7080
ctattcaatc tttgtcactt ctttttgatg gcaattatga tataatgatg tcagaacttg   7140
gttatacacc tcaggatttc ttagatttga tagagagtaa gagtataaca gggcaaataa   7200
tttatgttga tatggaaaac ttgtacgttg tgatcaggac atatctacct accctaattg   7260
aagtacctga tgcccaaata tatgagttca acaaaataac tatgagtagc aatggaggag   7320
aatacttgtc aaccatacct aatttcatat taataagagg taattatatg tctaatatag   7380
atgttgcaac atgttatatg accaaagcaa gcgtaatttg taatcaagat tattcactcc   7440
cgatgagcca aaacttaaga agctgttatc aaggtgagac agaatactgt cctgttgagg   7500
cagtcatcgc gtcacactct ccaagatttg ctcttacaaa tggagttatt ttcgccaatt   7560
gtataaatac aatttgtagg tgtcaagaca atggtaagac tatcactcaa aacataaacc   7620
aattcgtaag catgatcgac aacagtactt gtaatgatgt catggtagat aagtttacta   7680
tcaaggtagg aaaatatatg gggagaaaag atatcaataa tattaatatc cagataggac   7740
cgcagatcat aattgataag gttgacttgt ctaatgaaat aaacaagatg aatcaatctt   7800
taaaagatag tatttttctac ctgagagaag ccaagagaat tttagactca gtaaatatca   7860
gtcttatatc tccaagcgtt caattgtttc taataataat atcagtcctc tcatttatta   7920
tattattgat tatcatagta tacttgtact gtaaatcaaa acattcatat aaatataaca   7980
aatttataga tgatcctgat tattacaatg attacaaaag agaacgtatt aatggcaaag   8040
ccagtaagag taacaatata tattatgtag gtgattaaca atcgataatc taaaggatta   8100
cctcactatc actaccaagg taacttccat gtaagatcgg accttccccg aagacattaa   8160
ataaaactta ggatcccaga gtatccctct aagtgatcct tctagattgg ttactgatat   8220
atatacatat ttatcctctt tccgtcgttg tttattgatc attaataatg ctttctcagc   8280
tccaaaaaaa ttacttagac aactcaaacc aacaaggtga taaaatgaac aacccagata   8340
agaaattaag tgtcaacttc aaccctttag aattagataa aggtcaaaaa gatctcaata   8400
agtcttatta tgttaaaaac aagaattata acgtttcaaa tctattaaat gaaagtctgc   8460
acgatatcaa gttttgtatt tattgtatat tctcactgct aattatcatt acaataatca   8520
atataatcac aatatcaatt gttataactc gtctgaaagt acatgaagag aataatggca   8580
tggaatctcc taatttacaa tctattcaag atagtctctc atctcttact aacatgatca   8640
atacagagat aactcctaga atagggattt tagttacagc cacttctgtt actctctctt   8700
catctatcaa ttatgtcggg actaagacaa atcaactggt caatgaatta aaagattata   8760
taaccaaaag ttgtggcttt aaggtccctg aattaaagtt acatgaatgc aacataagtt   8820
gtgctgatcc aaaaattagc aaatctgcaa tgtacagcac caatgcctat gccgagcttg   8880
ctggtccacc taagatattt tgtaaaagtg tatccaaaga ccccgacttt agactgaagc   8940
agatagatta tgtaatacca gtgcagcaag atcggtctat ttgtatgaac aaccctttat   9000
tggatatttc tgatgggttt tttacctaca tacattatga aggaataaat agctgtaaaa   9060
aatcagattc atttaaagtg ctgctgtcac atggtgaaat agttgacagg ggtgattatc   9120
gaccatcatt atatctatta tcaagtcatt accatcctta ttcaatgcag gtaataaact   9180
```

-continued

```
gtgtacctgt gacttgtaac cagtcatcct ttgtattctg tcatatctcc aacaacacta   9240
aaacattgga caattcagat tactcgtcag acgagtacta cataacatat ttcaatggca   9300
tagatcgtcc caaaaccaag aagattccca ttaacaatat gacagcagac aatcgttata   9360
tccattttac attctcaggt gggggaggtg tatgtttagg tgaagaattt attattcctg   9420
ttaccacagt catcaatact gatgtattca cgcatgatta ttgtgagagt ttcaactgtt   9480
cagtccaaac cggtaaaagt ctaaaggaga tatgctctga gtcattaaga tctccaacga   9540
actcatcgcg atacaattta aacggaatca tgattataag tcaaaacaac atgacagatt   9600
ttaagattca gttgaatggt ataacttata acaaactgtc attcggaagt cctggaagac   9660
tgagcaagac actgggccag gtcctttatt accaatcttc aatgagttgg gatacttatc   9720
taaaggcagg atttgtcgag aaatggaaac cctttacccc gaattggatg aacaatactg   9780
tgatatccag acctaaccaa ggtaattgtc caaggtatca taaatgcccc gagatatgtt   9840
atggagggac atacaatgat attgctcctt tagatctagg aaaagacatg tatgttagcg   9900
ttattctaga ttcagatcag cttgcagaga atccagagat tacagtattt aactctacta   9960
ctatacttta taaggagaga gtatccaaag atgaactaaa cacaagaagt actacaacga  10020
gctgttttct tttcctagat gaaccttggt gtatatcagt attagaaaca aacagattta  10080
acggcaaatc tattaggccc gagatttatt catacaaaat tcctaagtat tgttaatttg  10140
atgagcttat tcctcatact tcaatcaaat ttaatataac taatatcaaa ttgttgcact  10200
cagctattat taaaactgga tcatcagaca ataaagatgt atacaaagat atatcgaaga  10260
gggtattaaa gaaaacttag gatcccagat ccttcaataa ggcagagcct tgattgtatc  10320
agcgtcattt acaattgaat ctcaattaac aacactgatt aataacttaa gcagaatact  10380
cctattacag tgtttaattg acttaatttt aattgaggat tttataatcc tataattgga  10440
gcagatctaa actctcaccg attcagttct aatcctttat taactaaaga acaaattcta  10500
aataattgga tgacgtcaca ggagacaagc tggaaacaat ttagttagaa ggaagaaacc  10560
ttttaccaga tatggaaagt gactttgata tatctgttag cgacgtactg tacccagaat  10620
gtcatttgga cagtcctata gtcggcggta agctcattac ttctcttgag tatgcgaatt  10680
tgactcataa ccaacctcat gaagatcaga cattgctgac taatataaat gtcaataaaa  10740
agaagaagat aaaaagtcct ctaatatccc aacaatcttt atttggaaat gaggttaata  10800
aggagatttt cgatcttaaa aattattacc atgtccccta tccagaatgt aacagagatt  10860
tattcttaat ctctgatgac aaaatagcat tcaaactcag taaaatcatg gataattcta  10920
ataaactgtt tgatggttta gagaggaaac tgagtcgctt aatttcgaat gtagataatc  10980
aactattaaa tgcaacctct cttcataata attctgagat ggatcggaag ggaaaagaac  11040
atccttgctt cccagaaaag agcacaattg atgatgtaag acagcagaga cagacacgag  11100
attttccaaa gaattcaact agagagggaa gatctccaaa acaccctgat gccggtccta  11160
cacctgaaaa cagtgccaaa aacgatttgc atagagacaa cacagacaat atgccaacag  11220
gccatagttc gacatctatg aaaaaaccta aaatatctgg agaagaatat cttagtatgt  11280
ggctagactc agaggatttg ggttctaaac gaatttctgc acaattaggg aaggatgtat  11340
catgtaaagg ccatctgcac acgacagaag acaaaccgat aatagttcct gacactcgat  11400
atatccaaaa tcatgaatct aataacgata ttttccccaa aaaagagaaa aaattctgca  11460
aacttccacc gtcatcggat aatttaacca aaatcatggt gaattcaaaa tggtacaatc  11520
ctttcctttt ttggtttact gtcaagactg aacttagagc ctgccagaag gagaactaca  11580
```

aaaggaaaaa cagaaaattg ggaattatca catcgattaa aggttcatgc tataagttga 11640
tactcaacca gaatctagta gcaatattcg aggaagacag cagtggatac tcagatcata 11700
aaaaaagaaa aaaacgatgc tactatctaa ctcccgaaat ggtccttatg ttctccgatg 11760
taactgaagg aagattgatg attgatgttg caatgagatt tgacaaaaag tacaaaactc 11820
tagagaaaaa ggctttgaaa ttatggtttc ttatagacga gttatttcct tctatgggaa 11880
atagagtgta taatattata tccatgcttg agcctttgac tctcgcgata ttacaggtta 11940
aggatgagtc aaggttgttg agaggtgcat tcatgcatca ttgtttaggt gacctcttcg 12000
aagaacttcg agagtccaag aactacccgg aagatgagat caagagattt gccaacgacc 12060
taataaatgt catgacctgt cgggacattc atttagtagc agaattcttc tcattcttta 12120
ggactttcgg acatccaata ttgaacgctc aaactgcagc caggaaagtt agagagtaca 12180
tgttagcaga taaaatcctt gagtacgaac ctatcatgaa aggtcatgcg attttctgtg 12240
ctataatcat aaatggattt agagatagac atggaggagt ttggcctcct cttgatcttc 12300
caaaacattg ttcaaagaac ataatatctc tcaaaaatac aggtgaaggg gtaacttatg 12360
aagtagcaat aaacaattgg agatcatttg tcgggttaaa gttcaaatgt tttatgggtc 12420
tcaatttaga caatgatctc agcatgtaca tgaaagataa agcattatca cctttaaggg 12480
atctttggga ttcaatctat tcacgtgaag taatgtccta ccaaccacct agaaacaaaa 12540
aatcaagaag attggttgag gttttcgttg atgatcagga ctttgatccc gttgatatga 12600
taaattatgt tctgaccgga gaatatctca gagatgatga tttcaatgct tcttatagtt 12660
taaaagagaa agagaccaaa caagttggca ggttgtttgc taagatgact tataaaatga 12720
gggcctgtca agttattgct gagaatttaa ttgcacatgg gattgggaga tatttccatg 12780
aaaacgggat ggttaaggat gagcatgagc tcagcaaatc actgtttcaa ttgtctatat 12840
caggaatacc aagagggaac aaaaacaaca aatcgacgaa cgacacaatc cacgaaagca 12900
agatcgagaa taaccattcc tttaaaaaca tccagaatcg atcatttcga aagacggata 12960
acccatacaa tagatttaac attgataacc caactttctt atccccaaac tgtaacccca 13020
agtataaccg taagaattca gagacaatag gtatattctc tcgtgcagaa accaaaagca 13080
tgattagaga acagaaaagt cacagagaag tcaaaataaa taagctagat atcggcagtg 13140
ataatgaaga gcaaggaaaa gagatagatg ccgccaagta caaaatcacg gacaacccaa 13200
atccacacat aaatcctcaa gatcaacccg gaatctgtca agaagacaaa ggcaaagaag 13260
gagcaaagtc agatctcaca gaaggcatga gttttctgga gatgcacaca ctctttaacc 13320
cgagtaagag cgatatcaga acaaatctcg aattggaaaa gagttcactt tcaaaccctg 13380
gatttatatc acaaaaagag aaaagaggca aaacttataa tgaatcccat tcactgggaa 13440
agttctctaa agaggatgaa gaaagatacg atgtcatcag tgcattcctg acaacagatt 13500
tacgaaaatt ctgcttaaat tggagacatg aatcaatcgg cattttttgca agaaggatgg 13560
acgaaatcta tggtttgcct ggtttcttta attggatgca cagaagacta gagcgatctg 13620
tgttatatgt tgcggaccct cattgcccgc cgtctatcaa tgaacatatc gatctaaacg 13680
attcacccga aagagacata tttatacatc atccgaaagg gggtatagaa ggatacagcc 13740
aaaaactgtg gacaatagcg actatccctt ttctattcct cagtgctcat gagacaaaca 13800
cccggatagc ggcagttgta caaggtgaca atcaatcaat tgcaattaca cataaggtcc 13860
accctcattt gccttacaaa atgaagaaag aactctctgc aatgcaggca aaaaaatatt 13920

-continued

```
tttcaaggtt acggcacaac atgaaggcat tagggcatga attgaaggcg accgagacta  13980
tcattagtac tcatttcttc atttattcca agaaaatcca ctatgacggg gctgttttat  14040
cacaatctct gaaatcaatg gcaaggtgtg tattttggtc agaaaccctt gttgatgaaa  14100
ctagagcagc atgcagtaat atcagcacaa caattgcaaa ggctattgag aatggttata  14160
gcaggagatc tggctatctg ataaatgttc ttaaaaccat ccaacaaatt aatatatcat  14220
tgagttttaa tataaatgaa tgcatgacag atgacataat cagaccgttt agagataatc  14280
caaactggat caaacatgcc gcattaatcc ccgccagctt gggaggactc aactatatga  14340
acatgtctcg attgtatgtg aggaatatag gggatccagt cacagcatcg atagcagatg  14400
ttaagagaat gattctcggt ggtgtactac ccattggaat actccacaat atcatgttgc  14460
aagaacccgg tgatgccact tatttggact ggtgtagtga tccatactcc atcaacctaa  14520
agcagactca aagtatcaca aaagttataa agaacataac ggcaagagtg atactaagga  14580
attcggtcaa tccactgctc aaaggtctat ttcatgaagg tgcttatgag gaggacactg  14640
aattagcaac attcattttg gacaggagag tcatcttacc acgagtcggt cacgagatct  14700
taaacaactc catcacagga gcaagagaag agatctcggg cttactggat accacaaaag  14760
gattgataag aattggcata gcaaagggag gattaactca gagaacatta tctcgaattt  14820
ccaattatga ttatgaacaa tttttgaacc taatgaatat gttgaagaac aaagaacaaa  14880
acagtgtcat ttccctgtca gcttgctctg ttgactttgc tatagcttta agaagcagga  14940
tgtggaggaa attggcaaaa ggaagattaa tatatggttt agaagtccct gatccaatag  15000
aagcaatgat tggctttctc attcttggga gtgaaaattg tctactctgt gattcaggaa  15060
gcaaaaacta tacctggttt ttcataccaa aggatgtaca gttggataag attgataaag  15120
atcacgcatc aataagggta ccctatgtcg gatcaactac cgaagaaaga tcagagataa  15180
agttaggatc cgtgaaaaat ccaagcaaat ccctgaaatc tgctataaga ctcgcaactg  15240
tgtacacttg ggcatttggc acaagtgatg ctgaatggtg ggaggcttgg tacttgtcta  15300
atcaacgagc aaatataccc ttagatgttc tcaaaacgat aacacctata tctacttcaa  15360
cgaatattgc tcatagatta cgagaccgat caacacaggt taaatacgcc agtacatctc  15420
ttaacagagt atcgcggcat gtaacaatta gtaacgataa catgaatttt gaatttgacg  15480
gggttaaaat ggataccaac ttgatttatc aacaagtcat gctgttaggg ctttcatgct  15540
tggagagttt attccgaaat aggaaaatga caaatagtta caatatcgtg taccatttac  15600
acgttcaaga acattgttgt gtaaaggctc tgaatgattt accttataca ccgtcaacac  15660
atccagtgcc aaattataca gaagttagag ataataggtt aatttacgat cctcaaccta  15720
tattagaatt tgatgagcta agattagcaa ttcagcaaac aaagaaagta gatttggaat  15780
tttcattgtg ggatacaaaa gaacttcatg agaatttagc tcaaagttta gcgattacag  15840
taacggatat tatgacaaaa tctgataaag atcatattaa agaccaaaga agtatagatg  15900
ttgatgataa tattaagaca ctaataactg agtttttatt agtagaccct gaaatgtttg  15960
ccgtaaattt aggattgcat atatcaataa aatggtcatt tgatattcac tttaaaagac  16020
caagaggacg ctatagcatg atagaatact tgactgatct tttggataat acttcttctc  16080
atgtttatcg aatccttact aatgtattat ctcatcccag agttatgaga aaattcacta  16140
atgccgggct actagtaccg aaatacggtc cctaccttac aagtcaagat ttcaaaaaga  16200
tggcggtaga tttcataata acagcgtata ccacattttt gaccaattgg tgtaataata  16260
acaagtttc aattctaata cctgaacaag accctgatat acttgaatta agaaaagaca  16320
```

-continued

```
tcactcatgc aaggcattta tgtatgatct cggatcttta ctgctactct ttcaagcaac  16380
cttggataaa ggagcttaca ccacaagaga agatctgcgt catggaggac ttcatagcca  16440
attgtgttgc taatgatcaa acaagtgcgg gctggaacat aacgccctta agagtttaca  16500
atctccctgc atcgaccaca tacatcagga gagggataat aaaacaatta agaatccgtc  16560
aaagcaatga gcctattgat ctggaagata ttaggattgg tcagaacccc gattttgtga  16620
ataaacctat tgagttttgt agcagtgaat tcggtatcac aatttataac cttgaagaaa  16680
ttcttcaatc aaatgtgcat ctcagtgtaa atatgaacat tgactcctca acaagtaaca  16740
atactgaaaa tcatttattt agaagggtag gcttgaactc tacttcatct tataaagcac  16800
tatctttaac acctgttatt aaaagatatc atcaacagaa cactaatagg ctgtttatag  16860
gagaaggatc agggtctatg atgtatcttt accagaaaac cttgggggag acaatatgct  16920
tctttaattc gggagttcag tacaatgagg atctgggtca aagggaacaa tcattatacc  16980
cgagtgaata cagtatctgt gaacaaggag taaaaaaaga aaaccctctc accgggcatg  17040
ttataccact attcaatgga agaccagaaa ccacatgggt aggcaatgat gattctttca  17100
agtatatatt ggaacatact ataaatagag acatcgggct tgttcactcc gatatggaaa  17160
caggaatagg gaaggataat tatactatct taaatgaaca tgcacatctt atagcactga  17220
gccttacagt aatgattgat gatggaatct tggtgtctaa ggtagcttat gcccctgggt  17280
tttgcatctc ttcattattg aatatgtacc ggacattttt ttcattagtt ctatgtgcgt  17340
ttccaccgta tagcaatttt gaatcaactg aattttacct gatttgcttg caaaaaagta  17400
tacccggacc tatcacacca gctagagcca tccaacaaac gacgaagcaa tctagagaag  17460
aggataatag tataactaat aatatcctca aaatcaaaaa tcttgttcag aaagaattta  17520
tcaaaacagt aaagaaaaaa tacgaaatcc atccttcgtt taactgtcct atcaacttca  17580
caaaggatga taaatattta atgagtgttg ggtttcaagc caatggtcct gatatgatac  17640
gtaaagagac gggctatgac ataggtagca atgtagagaa tctccgagat gtcttaatca  17700
agttgtttgc agatgcagtc accttctatg atgatgtcac aaataaaaag aactttttaa  17760
atccttatcc agtctacaca agaactcagt ataaaattct gatggataaa atatgcaaga  17820
aagtcacctt atacacctta atcatatcat gtaaaggatc caatcaatat tgctgggaaa  17880
ttaaatccca aataagaaag cattgtctca tacttgattt gaaaagtaag gtttttacaa  17940
aacttattcc aaagggatta agagaaaggg gtgactcaaa agggatgaag agcatatggt  18000
tcactaaact aaccagtcaa gaggtgaaaa gatggtggaa gatgatatct tacatcgtga  18060
taataagcaa tccataacca catccaactt gtcagttaaa cacttaaatc acaataaact  18120
tgtcatcaga ttaaagaaaa cttataattc cctttttag gt                      18162
```

<210> SEQ ID NO 2
<211> LENGTH: 510
<212> TYPE: PRT
<213> ORGANISM: Cedar virus

<400> SEQUENCE: 2

```
Met Ser Asp Ile Phe Asn Glu Thr Gln Ser Phe Arg Asn Tyr Gln Ser
1               5                   10                  15

Asn Leu Gly Arg Asp Gly Arg Ala Ser Ala Ala Thr Thr Thr Leu Thr
            20                  25                  30

Thr Lys Val Arg Ile Phe Val Pro Ala Asn Asn Asn Pro Asn Leu Arg
        35                  40                  45
```

-continued

```
Trp Arg Leu Thr Leu Phe Leu Met Asp Val Val Arg Ser Pro Ala Ser
    50                  55                  60

Ala Glu Ser Met Lys Val Gly Ala Gly Ile Ser Leu Val Ser Met Tyr
65                  70                  75                  80

Ala Glu Lys Pro Gly Ala Leu Val Arg Ala Leu Leu Asn Asp Pro Asp
                85                  90                  95

Val Glu Ala Ile Ile Ile Asp Val Tyr Gly Phe Asp Glu Gly Ile Pro
            100                 105                 110

Ile Met Glu Arg Arg Gly Asp Lys Ala Thr Asp Asp Met Asp Ser Leu
        115                 120                 125

Arg Lys Ile Val Lys Ala Ala His Asp Phe Ser Arg Gly Arg Ser Leu
    130                 135                 140

Phe Val Asp Gln Arg Val Gln Asp Ile Val Met Ser Asp Met Gly Ser
145                 150                 155                 160

Phe Val Asn Ala Ile Thr Ser Ile Glu Thr Gln Ile Trp Ile Leu Ile
                165                 170                 175

Ala Lys Ala Val Thr Ala Pro Asp Thr Ala Glu Glu Ser Glu Gly Arg
            180                 185                 190

Arg Trp Ala Lys Tyr Val Gln Gln Lys Arg Val Asn Pro Leu Phe Leu
        195                 200                 205

Ile Ser Pro Gln Trp Ile Asn Asp Met Arg Ser Leu Ile Ala Ala Ser
    210                 215                 220

Leu Ser Leu Arg Lys Phe Met Val Glu Leu Leu Met Glu Ala Lys Lys
225                 230                 235                 240

Gly Arg Gly Thr Lys Gly Arg Ile Met Glu Ile Val Ser Asp Ile Gly
                245                 250                 255

Asn Tyr Val Glu Glu Thr Gly Met Ala Gly Phe Phe Ala Thr Ile Lys
            260                 265                 270

Phe Gly Leu Glu Thr Lys Phe Pro Ala Leu Ala Leu Asn Glu Leu Gln
        275                 280                 285

Ser Asp Leu Asn Thr Met Lys Ser Leu Met Ile Leu Tyr Arg Ser Ile
    290                 295                 300

Gly Pro Lys Ala Pro Phe Met Val Leu Leu Glu Asp Ser Ile Gln Thr
305                 310                 315                 320

Lys Phe Ala Pro Gly Ser Tyr Pro Leu Leu Trp Ser Phe Ala Met Gly
                325                 330                 335

Val Gly Thr Thr Ile Asp Arg Ala Met Gly Ala Leu Asn Ile Asn Arg
            340                 345                 350

Ser Tyr Leu Glu Pro Val Tyr Phe Arg Leu Gly Gln Gln Ser Ala Lys
        355                 360                 365

His Gln Ala Gly Asn Val Asp Lys Glu Met Ala Glu Lys Leu Gly Leu
    370                 375                 380

Thr Glu Asp Gln Ile Val His Leu Ser Ala Asn Val Lys Asp Ala Ser
385                 390                 395                 400

Gln Gly Arg Asp Asp Asn Gln Ile Asn Ile Arg Glu Gly Lys Phe Thr
                405                 410                 415

Asn Val Val Asp Asp Ile Gln Asp His Ala Gln Ser Ser Ser Glu Asp
            420                 425                 430

Tyr Asn Pro Ser Lys Lys Ser Phe Ser Ile Leu Thr Ser Ile Thr Ser
        435                 440                 445

Thr Val Asp Ser Ala Asp Ser Arg Ser Ala Met Asn Glu Ser Met Thr
    450                 455                 460
```

```
Thr Thr Ser Leu Leu Lys Leu Arg Gln Arg Leu Ala Glu Lys Lys Gly
465                 470                 475                 480

Asp Ser Lys Asn Ser Gln Asp Thr Pro Pro Lys Pro Pro Arg Ala Lys
                485                 490                 495

Asp Gln Pro Thr Asp Glu Val Ser Phe Met Asp Ser Asn Ile
            500                 505                 510


<210> SEQ ID NO 3
<211> LENGTH: 737
<212> TYPE: PRT
<213> ORGANISM: Cedar virus

<400> SEQUENCE: 3

Met Asp Lys Leu Gln Leu Ile Glu Asp Gly Leu Ser Thr Ile Asn Phe
1               5                   10                  15

Ile Gln Glu Asn Lys Glu Lys Leu Gln His Ser Tyr Gly Arg Ser Ser
            20                  25                  30

Ile Arg Glu Pro Pro Thr Ser Val Arg Val Glu Glu Trp Glu Lys Phe
        35                  40                  45

Ile Arg Lys Ile Ala Ser Gly Pro Glu Gln Val Gln Gly Gly Gly Ser
    50                  55                  60

Glu Thr Glu Ile Thr Gly Asp Asn Gly Asp Arg Gly Asn Phe Thr Asn
65                  70                  75                  80

Pro Asp Gln Gly Gly Gly Val Thr Gly Gln Phe Glu Glu Arg Tyr Gln
                85                  90                  95

Lys Trp Gly Ser Gln Asp Ser Glu Leu Gln Leu Asp Pro Met Val Val
            100                 105                 110

His Asp Phe Phe Tyr Asp Glu Arg Arg Glu Asn Pro Asp Asn Gly Lys
        115                 120                 125

Tyr Asp Arg Ser Ser Lys Lys Arg Asp Asn Ile Arg Glu Gly Thr Arg
    130                 135                 140

Gln Asp Lys Tyr Asn Asn Gln Ser Thr Asp Glu Leu Leu Ser Cys Leu
145                 150                 155                 160

Gln Pro Ser Ser Lys Asn Asp Val Ile Lys Asn Glu Ser Thr Ser Val
                165                 170                 175

Ser Asn Leu His Val Thr Gly Asn Lys Leu Asn Pro Asp Ala Lys Pro
            180                 185                 190

Phe Glu Pro Thr Ser Gln Ser Lys Glu His Pro Thr Thr Thr Gln His
        195                 200                 205

Asn Lys Asn Asp His Gln Thr Asp Asp Asp Tyr Lys Asn Arg Arg Ser
    210                 215                 220

Ser Glu Asn Asn Val Ile Ser Asp His Ala Thr Thr Met Glu Asp Asn
225                 230                 235                 240

Asn Asn Phe Ile Pro Ala Thr Lys Arg Lys Asn Ala Leu Ser Glu Pro
                245                 250                 255

Ile Tyr Val Gln Val Leu Pro Ser Asn Thr Glu Gly Phe Ser Gly Lys
            260                 265                 270

Asp Tyr Pro Leu Leu Lys Asp Asn Ser Val Lys Lys Arg Ala Glu Pro
        275                 280                 285

Val Ile Leu Glu Thr Ala Asn His Pro Ala Gly Ser Ala Asp Gln Asp
    290                 295                 300

Thr Asn Gln Ile Glu Glu Asn Met Gln Phe Asn Leu Pro Lys Leu Leu
305                 310                 315                 320

Thr Glu Asp Thr Asp Asp Glu Pro Glu Asp Asn Asn Asp Ser Met Pro
                325                 330                 335
```

-continued

```
Leu Glu Glu Asp Ile Arg Glu Ile Gly Ser Met Leu Lys Asp Gly Thr
            340                 345                 350

Lys Asp Ile Lys Thr Arg Met Asn Glu Ile Asp Asp Ala Ile Lys Lys
        355                 360                 365

Ile Asn Lys Lys Ser Lys Asn Arg Ser Leu Asp Leu Glu Ser Asp Gly
    370                 375                 380

Lys Asp Gln Gly Arg Arg Asp Pro Ser Val Asp Leu Gly Ile Lys Lys
385                 390                 395                 400

Arg Lys Glu Gly Leu Lys Ala Ala Met Gln Lys Thr Lys Glu Gln Leu
                405                 410                 415

Ser Ile Lys Val Glu Arg Glu Ile Gly Leu Asn Asp Arg Ile Cys Gln
            420                 425                 430

Asn Ser Lys Met Ser Thr Glu Lys Lys Leu Ile Tyr Ala Gly Met Glu
        435                 440                 445

Met Glu Tyr Gly Gln Thr Ser Thr Gly Ser Gly Gly Pro Gln Gly Ser
    450                 455                 460

Lys Asp Gly Thr Ser Asp Asp Val Gln Val Asp Glu Asp Tyr Asp Glu
465                 470                 475                 480

Gly Glu Asp Tyr Glu Ala Met Pro Ser Asp Arg Phe Tyr Thr Thr Leu
                485                 490                 495

Ser Gly Glu Gln Lys Asp Arg Phe Asp Leu Asp Ala Asn Gln Met Ser
            500                 505                 510

Gln Tyr Asp Leu Glu Ala Gln Val Asp Glu Leu Thr Arg Met Asn Leu
        515                 520                 525

Ile Leu Tyr Ser Arg Leu Glu Thr Thr Asn Lys Leu Leu Ile Asp Ile
    530                 535                 540

Leu Asp Leu Ala Lys Glu Met Pro Lys Leu Val Arg Lys Val Asp Asn
545                 550                 555                 560

Leu Glu Arg Gln Met Gly Asn Leu Asn Met Leu Thr Ser Thr Leu Glu
                565                 570                 575

Gly His Leu Ser Ser Val Met Ile Met Ile Pro Gly Lys Asp Lys Ser
            580                 585                 590

Glu Lys Glu Ile Pro Lys Asn Pro Asp Leu Arg Pro Ile Leu Gly Arg
        595                 600                 605

Ser Asn Thr Ser Leu Thr Asp Val Ile Asp Leu Asp His Tyr Pro Asp
    610                 615                 620

Lys Gly Ser Lys Gly Ile Lys Pro Ser Gly Ser Gly Asp Arg Gln Tyr
625                 630                 635                 640

Ile Gly Ser Leu Glu Ser Lys Phe Ser Ile Asn Asp Glu Tyr Asn Phe
                645                 650                 655

Ala Pro Tyr Pro Ile Arg Asp Glu Leu Leu Leu Pro Gly Leu Arg Asp
            660                 665                 670

Asp Lys Thr Asn Ala Ser Ser Phe Ile Pro Asp Asp Thr Asp Arg Ser
        675                 680                 685

Pro Met Val Leu Lys Ile Ile Ile Arg Gln Asn Ile His Asp Glu Glu
    690                 695                 700

Val Lys Asp Glu Leu Leu Ser Ile Leu Glu Gln His Asn Thr Val Glu
705                 710                 715                 720

Glu Leu Asn Glu Ile Trp Asn Thr Val Asn Asp Tyr Leu Asp Gly Asn
                725                 730                 735

Ile
```

<210> SEQ ID NO 4
<211> LENGTH: 177
<212> TYPE: PRT
<213> ORGANISM: Cedar virus

<400> SEQUENCE: 4

```
Met Ala Ser Leu Leu Ser Ile Leu Tyr Arg Lys Ile Arg Lys Asn Tyr
1               5                   10                  15

Ser Ile Leu Thr Glu Asp Pro Pro Ser Glu Ser His Pro Gln Val Ser
            20                  25                  30

Gly Leu Lys Ser Gly Arg Asn Leu Phe Glu Arg Ser Leu Leu Asp Leu
        35                  40                  45

Asn Lys Phe Lys Gly Glu Asp Leu Arg Leu Arg Ser Gln Ala Ile Met
    50                  55                  60

Glu Ile Glu Ala Ile Leu Pro Ile Leu Ile Arg Glu Ala Glu Ser Gln
65                  70                  75                  80

Asp Asn Ser Lys Lys Gly Ile Lys Asn Gly Gly His Lys Ile Gln Asn
                85                  90                  95

Tyr Asn Trp Thr Gln Trp Leu Tyr Thr Ile Ser Ser Met Thr Arg Glu
            100                 105                 110

Gly Arg Ile Pro Thr Met Glu Asn Met Thr Ala Ala Leu Lys Asn Gly
        115                 120                 125

Ile Ile Ser Glu Lys Glu His Asp Arg Ile Ser Thr Ile Ile Ser Leu
    130                 135                 140

Leu Met Asn Tyr Cys Pro Ala Tyr Asn His Leu Leu Arg Thr Met Ser
145                 150                 155                 160

Ser Arg Met Lys Val His Gln Cys Gln Ile Cys Met Leu Gln Glu Ile
                165                 170                 175

Asn
```

<210> SEQ ID NO 5
<211> LENGTH: 360
<212> TYPE: PRT
<213> ORGANISM: Cedar virus

<400> SEQUENCE: 5

```
Met Asp Pro Ser Asp Leu Arg Arg Ile Ile Met Glu Asp Asp Lys Ser
1               5                   10                  15

Leu Val Asn Asn Asp Asp Ser Thr Glu Thr Asp Phe Leu Glu Lys Thr
            20                  25                  30

Trp Arg Glu Gly Ser Lys Ile Asp Lys Ile Thr Pro Glu Val Asp Glu
        35                  40                  45

Asn Gly Asn Met Val Pro Lys Tyr Val Val Phe Asn Pro Gly Lys Asn
    50                  55                  60

Glu Arg Lys Thr Ser Gly Tyr Gln Tyr Met Ile Cys Tyr Gly Phe Ile
65                  70                  75                  80

Glu Asp Gly Pro Ile Asn Gly Ser Pro Arg Val Lys Gly Asn Ile Arg
                85                  90                  95

Thr Thr Ala Ser Phe Pro Leu Gly Val Gly Lys Thr Tyr Ser Ser Pro
            100                 105                 110

Glu Glu Ile Leu Gln Glu Leu Thr Thr Leu Lys Ile Thr Val Arg Arg
        115                 120                 125

Thr Ala Gly Ser Asn Glu Lys Leu Val Tyr Gly Ile Thr Gly Pro Leu
    130                 135                 140

Asn His Leu Tyr Pro Trp Tyr Lys Val Leu Thr Gly Gly Ser Ile Phe
145                 150                 155                 160
```

```
Ser Ala Val Lys Val Cys Arg Asn Val Asp Gln Ile Leu Leu Asp Arg
                165                 170                 175

Pro Gln Ile Leu Arg Val Phe Phe Leu Ser Ile Thr Lys Leu Thr Asp
            180                 185                 190

Lys Gly Val Tyr Met Ile Pro Lys Ser Val Leu Asp Phe Arg Ser Asp
        195                 200                 205

Asn Ser Met Ala Phe Asn Leu Leu Val Tyr Leu Lys Ile Asp Thr Asp
    210                 215                 220

Ile Thr Lys Ala Gly Ile Arg Gly Ile Val Asn Lys Glu Gly Glu Arg
225                 230                 235                 240

Ile Thr Ser Phe Met Leu His Ile Gly Asn Phe Thr Arg Arg Gly Gly
                245                 250                 255

Lys His Tyr Ser Val Glu Tyr Cys Lys Arg Lys Ile Asp Lys Met Lys
            260                 265                 270

Leu Thr Phe Ala Leu Gly Thr Ile Gly Gly Leu Ser Leu His Ile Arg
        275                 280                 285

Ile Asp Gly Arg Ile Ser Lys Arg Leu Gln Ala Gln Val Gly Phe Gln
    290                 295                 300

Arg Asn Ile Cys Tyr Ser Leu Met Asp Thr Asn Pro Trp Leu Asn Lys
305                 310                 315                 320

Leu Thr Trp Asn Asn Ser Cys Glu Ile His Lys Val Thr Ala Val Ile
                325                 330                 335

Gln Pro Ser Val Pro Lys Asp Phe Met Leu Tyr Glu Asp Ile Leu Ile
            340                 345                 350

Asp Asn Thr Gly Lys Ile Leu Lys
        355                 360


<210> SEQ ID NO 6
<211> LENGTH: 557
<212> TYPE: PRT
<213> ORGANISM: Cedar virus

<400> SEQUENCE: 6

Met Ser Asn Lys Arg Thr Thr Val Leu Ile Ile Ile Ser Tyr Thr Leu
1               5                   10                  15

Phe Tyr Leu Asn Asn Ala Ala Ile Val Gly Phe Asp Phe Asp Lys Leu
            20                  25                  30

Asn Lys Ile Gly Val Val Gln Gly Arg Val Leu Asn Tyr Lys Ile Lys
        35                  40                  45

Gly Asp Pro Met Thr Lys Asp Leu Val Leu Lys Phe Ile Pro Asn Ile
    50                  55                  60

Val Asn Ile Thr Glu Cys Val Arg Glu Pro Leu Ser Arg Tyr Asn Glu
65                  70                  75                  80

Thr Val Arg Arg Leu Leu Leu Pro Ile His Asn Met Leu Gly Leu Tyr
                85                  90                  95

Leu Asn Asn Thr Asn Ala Lys Met Thr Gly Leu Met Ile Ala Gly Val
            100                 105                 110

Ile Met Gly Gly Ile Ala Ile Gly Ile Ala Thr Ala Ala Gln Ile Thr
        115                 120                 125

Ala Gly Phe Ala Leu Tyr Glu Ala Lys Lys Asn Thr Glu Asn Ile Gln
    130                 135                 140

Lys Leu Thr Asp Ser Ile Met Lys Thr Gln Asp Ser Ile Asp Lys Leu
145                 150                 155                 160

Thr Asp Ser Val Gly Thr Ser Ile Leu Ile Leu Asn Lys Leu Gln Thr
```

-continued

```
                165                 170                 175

Tyr Ile Asn Asn Gln Leu Val Pro Asn Leu Glu Leu Leu Ser Cys Arg
            180                 185                 190

Gln Asn Lys Ile Glu Phe Asp Leu Met Leu Thr Lys Tyr Leu Val Asp
        195                 200                 205

Leu Met Thr Val Ile Gly Pro Asn Ile Asn Asn Pro Val Asn Lys Asp
    210                 215                 220

Met Thr Ile Gln Ser Leu Ser Leu Leu Phe Asp Gly Asn Tyr Asp Ile
225                 230                 235                 240

Met Met Ser Glu Leu Gly Tyr Thr Pro Gln Asp Phe Leu Asp Leu Ile
                245                 250                 255

Glu Ser Lys Ser Ile Thr Gly Gln Ile Ile Tyr Val Asp Met Glu Asn
            260                 265                 270

Leu Tyr Val Val Ile Arg Thr Tyr Leu Pro Thr Leu Ile Glu Val Pro
        275                 280                 285

Asp Ala Gln Ile Tyr Glu Phe Asn Lys Ile Thr Met Ser Ser Asn Gly
    290                 295                 300

Gly Glu Tyr Leu Ser Thr Ile Pro Asn Phe Ile Leu Ile Arg Gly Asn
305                 310                 315                 320

Tyr Met Ser Asn Ile Asp Val Ala Thr Cys Tyr Met Thr Lys Ala Ser
                325                 330                 335

Val Ile Cys Asn Gln Asp Tyr Ser Leu Pro Met Ser Gln Asn Leu Arg
            340                 345                 350

Ser Cys Tyr Gln Gly Glu Thr Glu Tyr Cys Pro Val Glu Ala Val Ile
        355                 360                 365

Ala Ser His Ser Pro Arg Phe Ala Leu Thr Asn Gly Val Ile Phe Ala
    370                 375                 380

Asn Cys Ile Asn Thr Ile Cys Arg Cys Gln Asp Asn Gly Lys Thr Ile
385                 390                 395                 400

Thr Gln Asn Ile Asn Gln Phe Val Ser Met Ile Asp Asn Ser Thr Cys
                405                 410                 415

Asn Asp Val Met Val Asp Lys Phe Thr Ile Lys Val Gly Lys Tyr Met
            420                 425                 430

Gly Arg Lys Asp Ile Asn Asn Ile Asn Ile Gln Ile Gly Pro Gln Ile
        435                 440                 445

Ile Ile Asp Lys Val Asp Leu Ser Asn Glu Ile Asn Lys Met Asn Gln
    450                 455                 460

Ser Leu Lys Asp Ser Ile Phe Tyr Leu Arg Glu Ala Lys Arg Ile Leu
465                 470                 475                 480

Asp Ser Val Asn Ile Ser Leu Ile Ser Pro Ser Val Gln Leu Phe Leu
                485                 490                 495

Ile Ile Ile Ser Val Leu Ser Phe Ile Ile Leu Leu Ile Ile Ile Val
            500                 505                 510

Tyr Leu Tyr Cys Lys Ser Lys His Ser Tyr Lys Tyr Asn Lys Phe Ile
        515                 520                 525

Asp Asp Pro Asp Tyr Tyr Asn Asp Tyr Lys Arg Glu Arg Ile Asn Gly
    530                 535                 540

Lys Ala Ser Lys Ser Asn Asn Ile Tyr Tyr Val Gly Asp
545                 550                 555
```

<210> SEQ ID NO 7
<211> LENGTH: 622
<212> TYPE: PRT
<213> ORGANISM: Cedar virus

<400> SEQUENCE: 7

```
Met Leu Ser Gln Leu Gln Lys Asn Tyr Leu Asp Asn Ser Asn Gln Gln
1               5                   10                  15

Gly Asp Lys Met Asn Asn Pro Asp Lys Lys Leu Ser Val Asn Phe Asn
            20                  25                  30

Pro Leu Glu Leu Asp Lys Gly Gln Lys Asp Leu Asn Lys Ser Tyr Tyr
        35                  40                  45

Val Lys Asn Lys Asn Tyr Asn Val Ser Asn Leu Leu Asn Glu Ser Leu
    50                  55                  60

His Asp Ile Lys Phe Cys Ile Tyr Cys Ile Phe Ser Leu Leu Ile Ile
65                  70                  75                  80

Ile Thr Ile Ile Asn Ile Ile Thr Ile Ser Ile Val Ile Thr Arg Leu
                85                  90                  95

Lys Val His Glu Glu Asn Asn Gly Met Glu Ser Pro Asn Leu Gln Ser
            100                 105                 110

Ile Gln Asp Ser Leu Ser Ser Leu Thr Asn Met Ile Asn Thr Glu Ile
        115                 120                 125

Thr Pro Arg Ile Gly Ile Leu Val Thr Ala Thr Ser Val Thr Leu Ser
    130                 135                 140

Ser Ser Ile Asn Tyr Val Gly Thr Lys Thr Asn Gln Leu Val Asn Glu
145                 150                 155                 160

Leu Lys Asp Tyr Ile Thr Lys Ser Cys Gly Phe Lys Val Pro Glu Leu
                165                 170                 175

Lys Leu His Glu Cys Asn Ile Ser Cys Ala Asp Pro Lys Ile Ser Lys
            180                 185                 190

Ser Ala Met Tyr Ser Thr Asn Ala Tyr Ala Glu Leu Ala Gly Pro Pro
        195                 200                 205

Lys Ile Phe Cys Lys Ser Val Ser Lys Asp Pro Asp Phe Arg Leu Lys
    210                 215                 220

Gln Ile Asp Tyr Val Ile Pro Val Gln Gln Asp Arg Ser Ile Cys Met
225                 230                 235                 240

Asn Asn Pro Leu Leu Asp Ile Ser Asp Gly Phe Phe Thr Tyr Ile His
                245                 250                 255

Tyr Glu Gly Ile Asn Ser Cys Lys Lys Ser Asp Ser Phe Lys Val Leu
            260                 265                 270

Leu Ser His Gly Glu Ile Val Asp Arg Gly Asp Tyr Arg Pro Ser Leu
        275                 280                 285

Tyr Leu Leu Ser Ser His Tyr His Pro Tyr Ser Met Gln Val Ile Asn
    290                 295                 300

Cys Val Pro Val Thr Cys Asn Gln Ser Ser Phe Val Phe Cys His Ile
305                 310                 315                 320

Ser Asn Asn Thr Lys Thr Leu Asp Asn Ser Asp Tyr Ser Ser Asp Glu
                325                 330                 335

Tyr Tyr Ile Thr Tyr Phe Asn Gly Ile Asp Arg Pro Lys Thr Lys Lys
            340                 345                 350

Ile Pro Ile Asn Asn Met Thr Ala Asp Asn Arg Tyr Ile His Phe Thr
        355                 360                 365

Phe Ser Gly Gly Gly Gly Val Cys Leu Gly Glu Glu Phe Ile Ile Pro
    370                 375                 380

Val Thr Thr Val Ile Asn Thr Asp Val Phe Thr His Asp Tyr Cys Glu
385                 390                 395                 400

Ser Phe Asn Cys Ser Val Gln Thr Gly Lys Ser Leu Lys Glu Ile Cys
```

-continued

```
                405                 410                 415

Ser Glu Ser Leu Arg Ser Pro Thr Asn Ser Ser Arg Tyr Asn Leu Asn
            420                 425                 430

Gly Ile Met Ile Ile Ser Gln Asn Asn Met Thr Asp Phe Lys Ile Gln
        435                 440                 445

Leu Asn Gly Ile Thr Tyr Asn Lys Leu Ser Phe Gly Ser Pro Gly Arg
    450                 455                 460

Leu Ser Lys Thr Leu Gly Gln Val Leu Tyr Tyr Gln Ser Ser Met Ser
465                 470                 475                 480

Trp Asp Thr Tyr Leu Lys Ala Gly Phe Val Glu Lys Trp Lys Pro Phe
                485                 490                 495

Thr Pro Asn Trp Met Asn Asn Thr Val Ile Ser Arg Pro Asn Gln Gly
            500                 505                 510

Asn Cys Pro Arg Tyr His Lys Cys Pro Glu Ile Cys Tyr Gly Gly Thr
        515                 520                 525

Tyr Asn Asp Ile Ala Pro Leu Asp Leu Gly Lys Asp Met Tyr Val Ser
    530                 535                 540

Val Ile Leu Asp Ser Asp Gln Leu Ala Glu Asn Pro Glu Ile Thr Val
545                 550                 555                 560

Phe Asn Ser Thr Thr Ile Leu Tyr Lys Glu Arg Val Ser Lys Asp Glu
                565                 570                 575

Leu Asn Thr Arg Ser Thr Thr Thr Ser Cys Phe Leu Phe Leu Asp Glu
            580                 585                 590

Pro Trp Cys Ile Ser Val Leu Glu Thr Asn Arg Phe Asn Gly Lys Ser
        595                 600                 605

Ile Arg Pro Glu Ile Tyr Ser Tyr Lys Ile Pro Lys Tyr Cys
    610                 615                 620


<210> SEQ ID NO 8
<211> LENGTH: 2501
<212> TYPE: PRT
<213> ORGANISM: Cedar virus

<400> SEQUENCE: 8

Met Glu Ser Asp Phe Asp Ile Ser Val Ser Asp Val Leu Tyr Pro Glu
1               5                   10                  15

Cys His Leu Asp Ser Pro Ile Val Gly Gly Lys Leu Ile Thr Ser Leu
            20                  25                  30

Glu Tyr Ala Asn Leu Thr His Asn Gln Pro His Glu Asp Gln Thr Leu
        35                  40                  45

Leu Thr Asn Ile Asn Val Asn Lys Lys Lys Lys Ile Lys Ser Pro Leu
    50                  55                  60

Ile Ser Gln Gln Ser Leu Phe Gly Asn Glu Val Asn Lys Glu Ile Phe
65                  70                  75                  80

Asp Leu Lys Asn Tyr Tyr His Val Pro Tyr Pro Glu Cys Asn Arg Asp
                85                  90                  95

Leu Phe Leu Ile Ser Asp Asp Lys Ile Ala Phe Lys Leu Ser Lys Ile
            100                 105                 110

Met Asp Asn Ser Asn Lys Leu Phe Asp Gly Leu Glu Arg Lys Leu Ser
        115                 120                 125

Arg Leu Ile Ser Asn Val Asp Asn Gln Leu Leu Asn Ala Thr Ser Leu
    130                 135                 140

His Asn Asn Ser Glu Met Asp Arg Lys Gly Lys Glu His Pro Cys Phe
145                 150                 155                 160
```

-continued

```
Pro Glu Lys Ser Thr Ile Asp Asp Val Arg Gln Gln Arg Gln Thr Arg
                165                 170                 175

Asp Phe Pro Lys Asn Ser Thr Arg Glu Gly Arg Ser Pro Lys His Pro
            180                 185                 190

Asp Ala Gly Pro Thr Pro Glu Asn Ser Ala Lys Asn Asp Leu His Arg
        195                 200                 205

Asp Asn Thr Asp Asn Met Pro Thr Gly His Ser Ser Thr Ser Met Lys
    210                 215                 220

Lys Pro Lys Ile Ser Gly Glu Glu Tyr Leu Ser Met Trp Leu Asp Ser
225                 230                 235                 240

Glu Asp Leu Gly Ser Lys Arg Ile Ser Ala Gln Leu Gly Lys Asp Val
                245                 250                 255

Ser Cys Lys Gly His Leu His Thr Thr Glu Asp Lys Pro Ile Ile Val
            260                 265                 270

Pro Asp Thr Arg Tyr Ile Gln Asn His Glu Ser Asn Asn Asp Ile Phe
        275                 280                 285

Pro Lys Lys Glu Lys Lys Phe Cys Lys Leu Pro Pro Ser Ser Asp Asn
    290                 295                 300

Leu Thr Lys Ile Met Val Asn Ser Lys Trp Tyr Asn Pro Phe Leu Phe
305                 310                 315                 320

Trp Phe Thr Val Lys Thr Glu Leu Arg Ala Cys Gln Lys Glu Asn Tyr
                325                 330                 335

Lys Arg Lys Asn Arg Lys Leu Gly Ile Ile Thr Ser Ile Lys Gly Ser
            340                 345                 350

Cys Tyr Lys Leu Ile Leu Asn Gln Asn Leu Val Ala Ile Phe Glu Glu
        355                 360                 365

Asp Ser Ser Gly Tyr Ser Asp His Lys Lys Arg Lys Lys Arg Cys Tyr
    370                 375                 380

Tyr Leu Thr Pro Glu Met Val Leu Met Phe Ser Asp Val Thr Glu Gly
385                 390                 395                 400

Arg Leu Met Ile Asp Val Ala Met Arg Phe Asp Lys Lys Tyr Lys Thr
                405                 410                 415

Leu Glu Lys Lys Ala Leu Lys Leu Trp Phe Leu Ile Asp Glu Leu Phe
            420                 425                 430

Pro Ser Met Gly Asn Arg Val Tyr Asn Ile Ile Ser Met Leu Glu Pro
        435                 440                 445

Leu Thr Leu Ala Ile Leu Gln Val Lys Asp Glu Ser Arg Leu Leu Arg
    450                 455                 460

Gly Ala Phe Met His His Cys Leu Gly Asp Leu Phe Glu Glu Leu Arg
465                 470                 475                 480

Glu Ser Lys Asn Tyr Pro Glu Asp Glu Ile Lys Arg Phe Ala Asn Asp
                485                 490                 495

Leu Ile Asn Val Met Thr Cys Arg Asp Ile His Leu Val Ala Glu Phe
            500                 505                 510

Phe Ser Phe Phe Arg Thr Phe Gly His Pro Ile Leu Asn Ala Gln Thr
        515                 520                 525

Ala Ala Arg Lys Val Arg Glu Tyr Met Leu Ala Asp Lys Ile Leu Glu
    530                 535                 540

Tyr Glu Pro Ile Met Lys Gly His Ala Ile Phe Cys Ala Ile Ile Ile
545                 550                 555                 560

Asn Gly Phe Arg Asp Arg His Gly Gly Val Trp Pro Pro Leu Asp Leu
                565                 570                 575

Pro Lys His Cys Ser Lys Asn Ile Ile Ser Leu Lys Asn Thr Gly Glu
```

```
            580                 585                 590

Gly Val Thr Tyr Glu Val Ala Ile Asn Asn Trp Arg Ser Phe Val Gly
        595                 600                 605

Leu Lys Phe Lys Cys Phe Met Gly Leu Asn Leu Asp Asn Asp Leu Ser
    610                 615                 620

Met Tyr Met Lys Asp Lys Ala Leu Ser Pro Leu Arg Asp Leu Trp Asp
625                 630                 635                 640

Ser Ile Tyr Ser Arg Glu Val Met Ser Tyr Gln Pro Pro Arg Asn Lys
                645                 650                 655

Lys Ser Arg Arg Leu Val Glu Val Phe Val Asp Asp Gln Asp Phe Asp
            660                 665                 670

Pro Val Asp Met Ile Asn Tyr Val Leu Thr Gly Glu Tyr Leu Arg Asp
        675                 680                 685

Asp Asp Phe Asn Ala Ser Tyr Ser Leu Lys Glu Lys Glu Thr Lys Gln
    690                 695                 700

Val Gly Arg Leu Phe Ala Lys Met Thr Tyr Lys Met Arg Ala Cys Gln
705                 710                 715                 720

Val Ile Ala Glu Asn Leu Ile Ala His Gly Ile Gly Arg Tyr Phe His
                725                 730                 735

Glu Asn Gly Met Val Lys Asp Glu His Glu Leu Ser Lys Ser Leu Phe
            740                 745                 750

Gln Leu Ser Ile Ser Gly Ile Pro Arg Gly Asn Lys Asn Asn Lys Ser
        755                 760                 765

Thr Asn Asp Thr Ile His Glu Ser Lys Ile Glu Asn Asn His Ser Phe
    770                 775                 780

Lys Asn Ile Gln Asn Arg Ser Phe Arg Lys Thr Asp Asn Pro Tyr Asn
785                 790                 795                 800

Arg Phe Asn Ile Asp Asn Pro Thr Phe Leu Ser Pro Asn Cys Asn Pro
                805                 810                 815

Lys Tyr Asn Arg Lys Asn Ser Glu Thr Ile Gly Ile Phe Ser Arg Ala
            820                 825                 830

Glu Thr Lys Ser Met Ile Arg Glu Gln Lys Ser His Arg Glu Val Lys
        835                 840                 845

Ile Asn Lys Leu Asp Ile Gly Ser Asp Asn Glu Glu Gln Gly Lys Glu
    850                 855                 860

Ile Asp Ala Ala Lys Tyr Lys Ile Thr Asp Asn Pro Asn Pro His Ile
865                 870                 875                 880

Asn Pro Gln Asp Gln Pro Gly Ile Cys Gln Glu Asp Lys Gly Lys Glu
                885                 890                 895

Gly Ala Lys Ser Asp Leu Thr Glu Gly Met Ser Phe Leu Glu Met His
            900                 905                 910

Thr Leu Phe Asn Pro Ser Lys Ser Asp Ile Arg Thr Asn Leu Glu Leu
        915                 920                 925

Glu Lys Ser Ser Leu Ser Asn Pro Gly Phe Ile Ser Gln Lys Glu Lys
    930                 935                 940

Arg Gly Lys Thr Tyr Asn Glu Ser His Ser Leu Gly Lys Phe Ser Lys
945                 950                 955                 960

Glu Asp Glu Glu Arg Tyr Asp Val Ile Ser Ala Phe Leu Thr Thr Asp
                965                 970                 975

Leu Arg Lys Phe Cys Leu Asn Trp Arg His Glu Ser Ile Gly Ile Phe
            980                 985                 990

Ala Arg Arg Met Asp Glu Ile Tyr  Gly Leu Pro Gly Phe  Phe Asn Trp
        995                 1000                1005
```

-continued

```
Met His  Arg Arg Leu Glu Arg  Ser Val Leu Tyr Val  Ala Asp Pro
    1010                 1015                 1020

His Cys  Pro Pro Ser Ile Asn  Glu His Ile Asp Leu  Asn Asp Ser
    1025                 1030                 1035

Pro Glu  Arg Asp Ile Phe Ile  His His Pro Lys Gly  Gly Ile Glu
    1040                 1045                 1050

Gly Tyr  Ser Gln Lys Leu Trp  Thr Ile Ala Thr Ile  Pro Phe Leu
    1055                 1060                 1065

Phe Leu  Ser Ala His Glu Thr  Asn Thr Arg Ile Ala  Ala Val Val
    1070                 1075                 1080

Gln Gly  Asp Asn Gln Ser Ile  Ala Ile Thr His Lys  Val His Pro
    1085                 1090                 1095

His Leu  Pro Tyr Lys Met Lys  Lys Glu Leu Ser Ala  Met Gln Ala
    1100                 1105                 1110

Lys Lys  Tyr Phe Ser Arg Leu  Arg His Asn Met Lys  Ala Leu Gly
    1115                 1120                 1125

His Glu  Leu Lys Ala Thr Glu  Thr Ile Ile Ser Thr  His Phe Phe
    1130                 1135                 1140

Ile Tyr  Ser Lys Lys Ile His  Tyr Asp Gly Ala Val  Leu Ser Gln
    1145                 1150                 1155

Ser Leu  Lys Ser Met Ala Arg  Cys Val Phe Trp Ser  Glu Thr Leu
    1160                 1165                 1170

Val Asp  Glu Thr Arg Ala Ala  Cys Ser Asn Ile Ser  Thr Thr Ile
    1175                 1180                 1185

Ala Lys  Ala Ile Glu Asn Gly  Tyr Ser Arg Arg Ser  Gly Tyr Leu
    1190                 1195                 1200

Ile Asn  Val Leu Lys Thr Ile  Gln Gln Ile Asn Ile  Ser Leu Ser
    1205                 1210                 1215

Phe Asn  Ile Asn Glu Cys Met  Thr Asp Asp Ile Ile  Arg Pro Phe
    1220                 1225                 1230

Arg Asp  Asn Pro Asn Trp Ile  Lys His Ala Ala Leu  Ile Pro Ala
    1235                 1240                 1245

Ser Leu  Gly Gly Leu Asn Tyr  Met Asn Met Ser Arg  Leu Tyr Val
    1250                 1255                 1260

Arg Asn  Ile Gly Asp Pro Val  Thr Ala Ser Ile Ala  Asp Val Lys
    1265                 1270                 1275

Arg Met  Ile Leu Gly Gly Val  Leu Pro Ile Gly Ile  Leu His Asn
    1280                 1285                 1290

Ile Met  Leu Gln Glu Pro Gly  Asp Ala Thr Tyr Leu  Asp Trp Cys
    1295                 1300                 1305

Ser Asp  Pro Tyr Ser Ile Asn  Leu Lys Gln Thr Gln  Ser Ile Thr
    1310                 1315                 1320

Lys Val  Ile Lys Asn Ile Thr  Ala Arg Val Ile Leu  Arg Asn Ser
    1325                 1330                 1335

Val Asn  Pro Leu Leu Lys Gly  Leu Phe His Glu Gly  Ala Tyr Glu
    1340                 1345                 1350

Glu Asp  Thr Glu Leu Ala Thr  Phe Ile Leu Asp Arg  Arg Val Ile
    1355                 1360                 1365

Leu Pro  Arg Val Gly His Glu  Ile Leu Asn Asn Ser  Ile Thr Gly
    1370                 1375                 1380

Ala Arg  Glu Glu Ile Ser Gly  Leu Leu Asp Thr Thr  Lys Gly Leu
    1385                 1390                 1395
```

-continued

```
Ile Arg  Ile Gly Ile Ala Lys  Gly Gly Leu Thr Gln  Arg Thr Leu
    1400                 1405                 1410

Ser Arg  Ile Ser Asn Tyr Asp  Tyr Glu Gln Phe Leu  Asn Leu Met
    1415                 1420                 1425

Asn Met  Leu Lys Asn Lys Glu  Gln Asn Ser Val Ile  Ser Leu Ser
    1430                 1435                 1440

Ala Cys  Ser Val Asp Phe Ala  Ile Ala Leu Arg Ser  Arg Met Trp
    1445                 1450                 1455

Arg Lys  Leu Ala Lys Gly Arg  Leu Ile Tyr Gly Leu  Glu Val Pro
    1460                 1465                 1470

Asp Pro  Ile Glu Ala Met Ile  Gly Phe Leu Ile Leu  Gly Ser Glu
    1475                 1480                 1485

Asn Cys  Leu Leu Cys Asp Ser  Gly Ser Lys Asn Tyr  Thr Trp Phe
    1490                 1495                 1500

Phe Ile  Pro Lys Asp Val Gln  Leu Asp Lys Ile Asp  Lys Asp His
    1505                 1510                 1515

Ala Ser  Ile Arg Val Pro Tyr  Val Gly Ser Thr Thr  Glu Glu Arg
    1520                 1525                 1530

Ser Glu  Ile Lys Leu Gly Ser  Val Lys Asn Pro Ser  Lys Ser Leu
    1535                 1540                 1545

Lys Ser  Ala Ile Arg Leu Ala  Thr Val Tyr Thr Trp  Ala Phe Gly
    1550                 1555                 1560

Thr Ser  Asp Ala Glu Trp Trp  Glu Ala Trp Tyr Leu  Ser Asn Gln
    1565                 1570                 1575

Arg Ala  Asn Ile Pro Leu Asp  Val Leu Lys Thr Ile  Thr Pro Ile
    1580                 1585                 1590

Ser Thr  Ser Thr Asn Ile Ala  His Arg Leu Arg Asp  Arg Ser Thr
    1595                 1600                 1605

Gln Val  Lys Tyr Ala Ser Thr  Ser Leu Asn Arg Val  Ser Arg His
    1610                 1615                 1620

Val Thr  Ile Ser Asn Asp Asn  Met Asn Phe Glu Phe  Asp Gly Val
    1625                 1630                 1635

Lys Met  Asp Thr Asn Leu Ile  Tyr Gln Gln Val Met  Leu Leu Gly
    1640                 1645                 1650

Leu Ser  Cys Leu Glu Ser Leu  Phe Arg Asn Arg Lys  Met Thr Asn
    1655                 1660                 1665

Ser Tyr  Asn Ile Val Tyr His  Leu His Val Gln Glu  His Cys Cys
    1670                 1675                 1680

Val Lys  Ala Leu Asn Asp Leu  Pro Tyr Thr Pro Ser  Thr His Pro
    1685                 1690                 1695

Val Pro  Asn Tyr Thr Glu Val  Arg Asp Asn Arg Leu  Ile Tyr Asp
    1700                 1705                 1710

Pro Gln  Pro Ile Leu Glu Phe  Asp Glu Leu Arg Leu  Ala Ile Gln
    1715                 1720                 1725

Gln Thr  Lys Lys Val Asp Leu  Glu Phe Ser Leu Trp  Asp Thr Lys
    1730                 1735                 1740

Glu Leu  His Glu Asn Leu Ala  Gln Ser Leu Ala Ile  Thr Val Thr
    1745                 1750                 1755

Asp Ile  Met Thr Lys Ser Asp  Lys Asp His Ile Lys  Asp Gln Arg
    1760                 1765                 1770

Ser Ile  Asp Val Asp Asp Asn  Ile Lys Thr Leu Ile  Thr Glu Phe
    1775                 1780                 1785

Leu Leu  Val Asp Pro Glu Met  Phe Ala Val Asn Leu  Gly Leu His
```

-continued

```
    1790                1795                1800

Ile Ser  Ile Lys Trp Ser Phe  Asp Ile His Phe Lys  Arg Pro Arg
    1805                1810                1815

Gly Arg  Tyr Ser Met Ile Glu  Tyr Leu Thr Asp Leu  Leu Asp Asn
    1820                1825                1830

Thr Ser  Ser His Val Tyr Arg  Ile Leu Thr Asn Val  Leu Ser His
    1835                1840                1845

Pro Arg  Val Met Arg Lys Phe  Thr Asn Ala Gly Leu  Leu Val Pro
    1850                1855                1860

Lys Tyr  Gly Pro Tyr Leu Thr  Ser Gln Asp Phe Lys  Lys Met Ala
    1865                1870                1875

Val Asp  Phe Ile Ile Thr Ala  Tyr Thr Thr Phe Leu  Thr Asn Trp
    1880                1885                1890

Cys Asn  Asn Asn Lys Phe Ser  Ile Leu Ile Pro Glu  Gln Asp Pro
    1895                1900                1905

Asp Ile  Leu Glu Leu Arg Lys  Asp Ile Thr His Ala  Arg His Leu
    1910                1915                1920

Cys Met  Ile Ser Asp Leu Tyr  Cys Tyr Ser Phe Lys  Gln Pro Trp
    1925                1930                1935

Ile Lys  Glu Leu Thr Pro Gln  Glu Lys Ile Cys Val  Met Glu Asp
    1940                1945                1950

Phe Ile  Ala Asn Cys Val Ala  Asn Asp Gln Thr Ser  Ala Gly Trp
    1955                1960                1965

Asn Ile  Thr Pro Leu Arg Val  Tyr Asn Leu Pro Ala  Ser Thr Thr
    1970                1975                1980

Tyr Ile  Arg Arg Gly Ile Ile  Lys Gln Leu Arg Ile  Arg Gln Ser
    1985                1990                1995

Asn Glu  Pro Ile Asp Leu Glu  Asp Ile Arg Ile Gly  Gln Asn Pro
    2000                2005                2010

Asp Phe  Val Asn Lys Pro Ile  Glu Phe Cys Ser Ser  Glu Phe Gly
    2015                2020                2025

Ile Thr  Ile Tyr Asn Leu Glu  Glu Ile Leu Gln Ser  Asn Val His
    2030                2035                2040

Leu Ser  Val Asn Met Asn Ile  Asp Ser Ser Thr Ser  Asn Asn Thr
    2045                2050                2055

Glu Asn  His Leu Phe Arg Arg  Val Gly Leu Asn Ser  Thr Ser Ser
    2060                2065                2070

Tyr Lys  Ala Leu Ser Leu Thr  Pro Val Ile Lys Arg  Tyr His Gln
    2075                2080                2085

Gln Asn  Thr Asn Arg Leu Phe  Ile Gly Glu Gly Ser  Gly Ser Met
    2090                2095                2100

Met Tyr  Leu Tyr Gln Lys Thr  Leu Gly Glu Thr Ile  Cys Phe Phe
    2105                2110                2115

Asn Ser  Gly Val Gln Tyr Asn  Glu Asp Leu Gly Gln  Arg Glu Gln
    2120                2125                2130

Ser Leu  Tyr Pro Ser Glu Tyr  Ser Ile Cys Glu Gln  Gly Val Lys
    2135                2140                2145

Lys Glu  Asn Pro Leu Thr Gly  His Val Ile Pro Leu  Phe Asn Gly
    2150                2155                2160

Arg Pro  Glu Thr Thr Trp Val  Gly Asn Asp Asp Ser  Phe Lys Tyr
    2165                2170                2175

Ile Leu  Glu His Thr Ile Asn  Arg Asp Ile Gly Leu  Val His Ser
    2180                2185                2190
```

```
Asp Met  Glu Thr Gly Ile Gly  Lys Asp Asn Tyr Thr  Ile Leu Asn
    2195                 2200                 2205

Glu His  Ala His Leu Ile Ala  Leu Ser Leu Thr Val  Met Ile Asp
    2210                 2215                 2220

Asp Gly  Ile Leu Val Ser Lys  Val Ala Tyr Ala Pro  Gly Phe Cys
    2225                 2230                 2235

Ile Ser  Ser Leu Leu Asn Met  Tyr Arg Thr Phe Phe  Ser Leu Val
    2240                 2245                 2250

Leu Cys  Ala Phe Pro Pro Tyr  Ser Asn Phe Glu Ser  Thr Glu Phe
    2255                 2260                 2265

Tyr Leu  Ile Cys Leu Gln Lys  Ser Ile Pro Gly Pro  Ile Thr Pro
    2270                 2275                 2280

Ala Arg  Ala Ile Gln Gln Thr  Thr Lys Gln Ser Arg  Glu Glu Asp
    2285                 2290                 2295

Asn Ser  Ile Thr Asn Asn Ile  Leu Lys Ile Lys Asn  Leu Val Gln
    2300                 2305                 2310

Lys Glu  Phe Ile Lys Thr Val  Lys Lys Lys Tyr Glu  Ile His Pro
    2315                 2320                 2325

Ser Phe  Asn Cys Pro Ile Asn  Phe Thr Lys Asp Asp  Lys Tyr Leu
    2330                 2335                 2340

Met Ser  Val Gly Phe Gln Ala  Asn Gly Pro Asp Met  Ile Arg Lys
    2345                 2350                 2355

Glu Thr  Gly Tyr Asp Ile Gly  Ser Asn Val Glu Asn  Leu Arg Asp
    2360                 2365                 2370

Val Leu  Ile Lys Leu Phe Ala  Asp Ala Val Thr Phe  Tyr Asp Asp
    2375                 2380                 2385

Val Thr  Asn Lys Lys Asn Phe  Leu Asn Pro Tyr Pro  Val Tyr Thr
    2390                 2395                 2400

Arg Thr  Gln Tyr Lys Ile Leu  Met Asp Lys Ile Cys  Lys Lys Val
    2405                 2410                 2415

Thr Leu  Tyr Thr Leu Ile Ile  Ser Cys Lys Gly Ser  Asn Gln Tyr
    2420                 2425                 2430

Cys Trp  Glu Ile Lys Ser Gln  Ile Arg Lys His Cys  Leu Ile Leu
    2435                 2440                 2445

Asp Leu  Lys Ser Lys Val Phe  Thr Lys Leu Ile Pro  Lys Gly Leu
    2450                 2455                 2460

Arg Glu  Arg Gly Asp Ser Lys  Gly Met Lys Ser Ile  Trp Phe Thr
    2465                 2470                 2475

Lys Leu  Thr Ser Gln Glu Val  Lys Arg Trp Trp Lys  Met Ile Ser
    2480                 2485                 2490

Tyr Ile  Val Ile Ile Ser Asn  Pro
    2495                 2500
```

<210> SEQ ID NO 9
<211> LENGTH: 14
<212> TYPE: DNA
<213> ORGANISM: Artificial Sequence
<220> FEATURE:
<223> OTHER INFORMATION: Hendra virus

<400> SEQUENCE: 9
ttaaaaaggg gggg 14

<210> SEQ ID NO 10
<211> LENGTH: 14

<212> TYPE: DNA
<213> ORGANISM: Artificial Sequence
<220> FEATURE:
<223> OTHER INFORMATION: Nipah virus

<400> SEQUENCE: 10
ttaaaaaggg gaca 14

<210> SEQ ID NO 11
<211> LENGTH: 14
<212> TYPE: DNA
<213> ORGANISM: Artificial Sequence
<220> FEATURE:
<223> OTHER INFORMATION: Cedar virus

<400> SEQUENCE: 11
cgaagatgag taca 14

<210> SEQ ID NO 12
<211> LENGTH: 25
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (18)..(25)
<223> OTHER INFORMATION: n is a, c, g, or t

<400> SEQUENCE: 12
gtttcccagt aggtctcnnn nnnnn 25

<210> SEQ ID NO 13
<211> LENGTH: 27
<212> TYPE: DNA
<213> ORGANISM: Artificial Sequence
<220> FEATURE:
<223> OTHER INFORMATION: primer sequence
<220> FEATURE:
<221> NAME/KEY: modified_base
<222> LOCATION: (2)..(5)
<223> OTHER INFORMATION: thiol modification

<400> SEQUENCE: 13
agcactgtag gtttcccagt aggtctc 27

<210> SEQ ID NO 14
<211> LENGTH: 22
<212> TYPE: DNA
<213> ORGANISM: Artificial Sequence
<220> FEATURE:
<223> OTHER INFORMATION: forward primer

<400> SEQUENCE: 14
tgcattgagc gaacccatat ac 22

<210> SEQ ID NO 15
<211> LENGTH: 22
<212> TYPE: DNA
<213> ORGANISM: Artificial Sequence
<220> FEATURE:
<223> OTHER INFORMATION: reverse primer

<400> SEQUENCE: 15
gcacgcttct tgacagagtt gt 22

<210> SEQ ID NO 16

-continued

```
<211> LENGTH: 27
<212> TYPE: DNA
<213> ORGANISM: Artificial Sequence
<220> FEATURE:
<223> OTHER INFORMATION: probe

<400> SEQUENCE: 16

tcccgagaaa ccctctgtgt ttgamgb                                          27
```

IMMUNOGENIC CEDAR VIRUS COMPOSITIONS

CROSS-REFERENCE TO RELATED APPLICATIONS

This application is a continuation of U.S. Application No. 15/180,544 (now U.S. Pat. No. 10,227,664) filed Jun. 13, 2016, which is a continuation of U.S. Application No. 14/412,533 filed Jan. 2, 2015, which is a National Stage Entry of International Application PCT/US2013/049069 filed on Jul. 2, 2013, which claims priority to U.S. Provisional Application No. 61/667,194, filed Jul. 2, 2012, the disclosures of which are all hereby incorporated by reference in its entirety.

STATEMENT REGARDING FEDERALLY SPONSORED RESEARCH OR DEVELOPMENT

Part of the work performed during development of this invention utilized U.S. Government funds under National Institutes of Health Grant Nos. AI054715. The U.S. Government has certain rights in this invention.

SEQUENCE LISTING SUBMISSION VIA EFS-WEB

A computer readable text file, entitled "SequenceListing.txt," created on or about Jan. 7, 2020 with a file size of about 72 kb contains the sequence listing for this application and is hereby incorporated by reference in its entirety.

BACKGROUND OF THE INVENTION

Field of the Invention

The present invention relates to a novel virus, called Cedar Virus, and its methods of use.

Background of the Invention

Henipaviruses were first discovered in the 1990s in disease outbreaks in farm animals and humans in Australia and Malaysia (1, 2). These viruses comprise the only known Biosafety Level 4 (BSL4) agents in the family Paramyxoviridae (3), and mortality is between 40% to 100% in both humans and animals (4, 5), depending upon the virus, animal species and geographic locations of outbreaks. The genus *Henipavirus* in the subfamily Paramyxovirinae currently contains two members, Hendra virus (HeV) and Nipah virus (NiV), with fruit bats, commonly known as flying foxes, as having been identified as the main natural reservoir of both viruses. Serological evidence, however, also suggests that henipaviruses may circulate in other types of bats (7-10).

The discovery of henipaviruses has had a significant impact on our overall understanding of paramyxoviruses. Indeed, Paramyxoviruses, such as measles virus and canine distemper virus, have a narrow host range and are known to be genetically stable with a close to uniform genome size shared by all members of Paramyxovirinae (3). Henipaviruses, however, shifted these paradigms as these viruses have a much wider host range and a significantly larger genome (6).

Recently, research on henipavirus has successfully identified functional cellular receptors and has driven the development of novel diagnostics, vaccine and therapeutics (15-25). There is, however, little understanding of the pathogenesis of these highly lethal viruses, due in part to the requirement of a high security BSL4 facility needed to conduct live infection studies and in part to the limited number of research tools available used in the current animal models. Research into the mechanisms of henipavirus pathogenesis is also hampered by the lack of related, non-pathogenic or less pathogenic viruses that could be used in comparative pathogenetic studies.

Recent serological investigations in China and other regions indicated the presence of cross-reactive, but not necessarily cross-neutralizing, antibodies to henipaviruses in bats of different species (8). Detection of henipavirus-like genomic sequences in African bats further support the results obtained from the serological investigations (26).

The invention disclosed herein is directed to the isolation and characterization of a newly discovered henipavirus.

SUMMARY OF THE INVENTION

The present invention is directed towards a novel virus, named Cedar Virus ("CedPV"), and its methods of use.

The present invention is also directed towards the individual proteins, and fragments thereof, as well as the coding sequences of the individual proteins that make up the CedPV.

The present invention is also directed to antibodies or fragments thereof that specifically bind to CedPV.

The present invention is also directed to vaccines and/or other therapeutic compositions comprising at least a portion of the CedPV.

BRIEF DESCRIPTION OF THE DRAWINGS

FIG. 2 depicts a comparison of genomic features among different henipaviruses. (A) Alignment of leader and trailer sequences (antigenome sequences shown). (B) Sequences of intergenic regions (IGR) and transcriptional start and stop sties of CedPV in comparison with those of HeV and niV.

AY988601; Nipah virus, Malaysian strain (NiV-M) AJ627196; Parainfluenza virus 5 (PIV5) AF052755; Peste-des-petits-ruminants (PPRV) X74443; Porcine rubulavirus (PorPV) BK005918; Rinderpest virus (RPV) Z30697; Salem virus (SalPV) AF237881; Sendai virus (SeV) M19661; Simian virus 41 (SV41) X64275; Tioman virus (TioPV) AF298895; Tupaia paramyxovirus (TupPV) AF079780. (B) The tree is based on whole genome sequence. (C) The tree is based on a 550-nt region of the L-gene.

Figure 4:
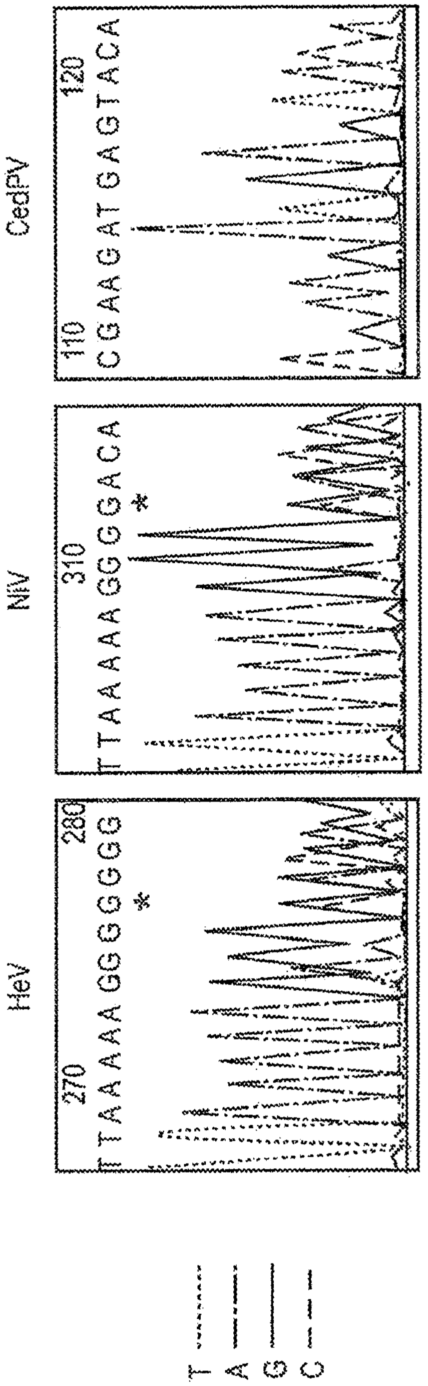

FIG. 4 depicts the sequencing trace files for the editing site of P genes for HeV and NiV in comparison to the editing site of the CedPV P gene. Trace files showing editing of the HeV and NiV P gene (indicated by the * sign) and lack of editing in CedPV P gene mRNA in infected cells. Sequencing of PCR products covering all potential editing sites in the P gene of CedPV did not reveal any RNA editing activity. A representative potential editing site of the CedPV P gene is shown.

Figure 5:
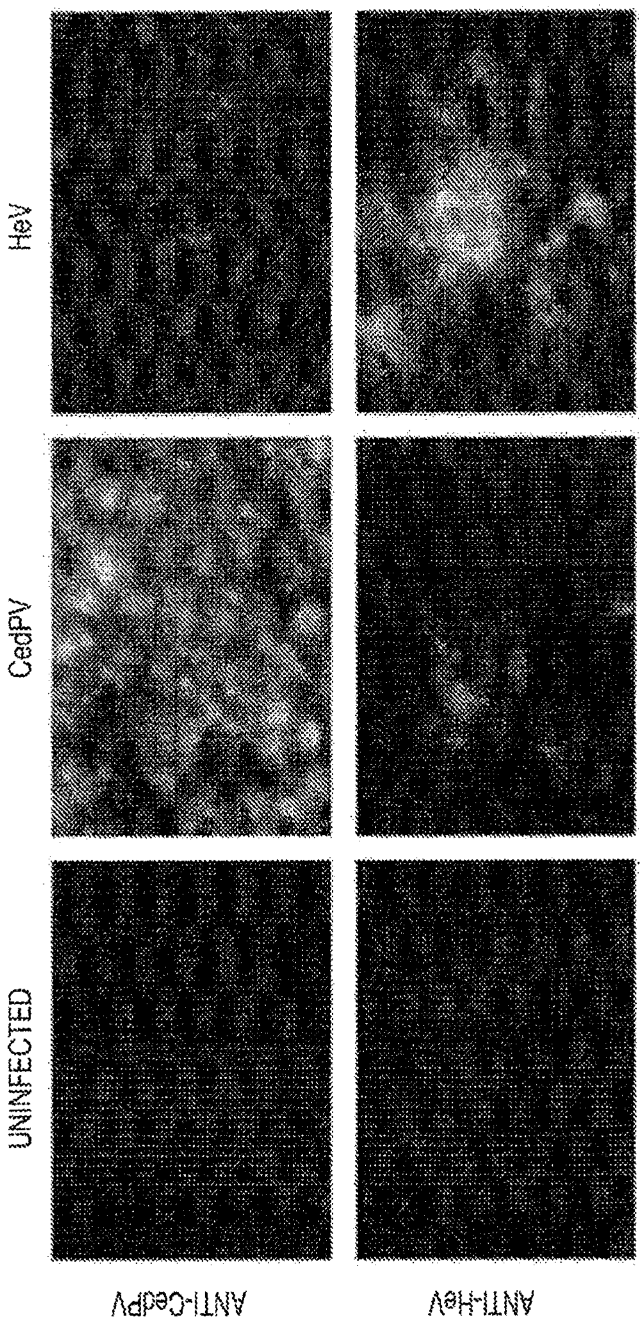

FIG. 5 depicts the antigenic cross reactivity between CedPV and HeV. Vero cells infected with CedPV and HeV, respectively, were stained with rabbit sera raised against recombinant N proteins of each virus.

Figure 6:
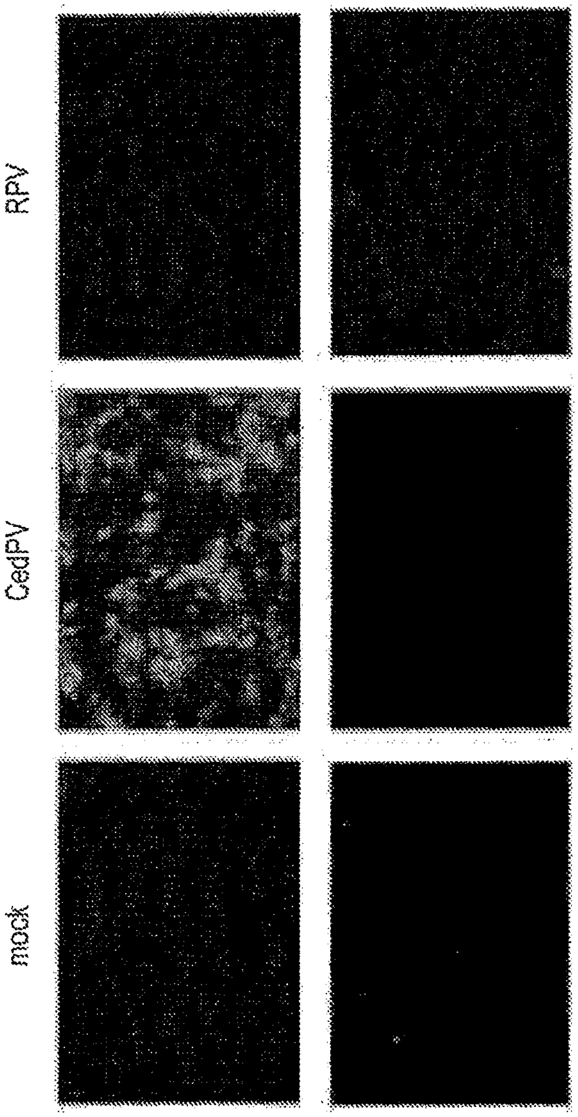

FIG. 6 depicts antigenic cross reactivity of CedPV with other paramyxoviruses. An Indirect Fluorescent Antibody (IFAT) assay conducted with anti-CedPV serum on Vero cells infected with J paramyxovirus (JPV), Rinderpest virus (RPV), Sendai virus (SeV), Menangle virus (MenPV) and CedPV, respectively. Mock infected cell monolayer was included as a negative control. The only panel showing reactivity is the CedPV panel.

Figure 7:
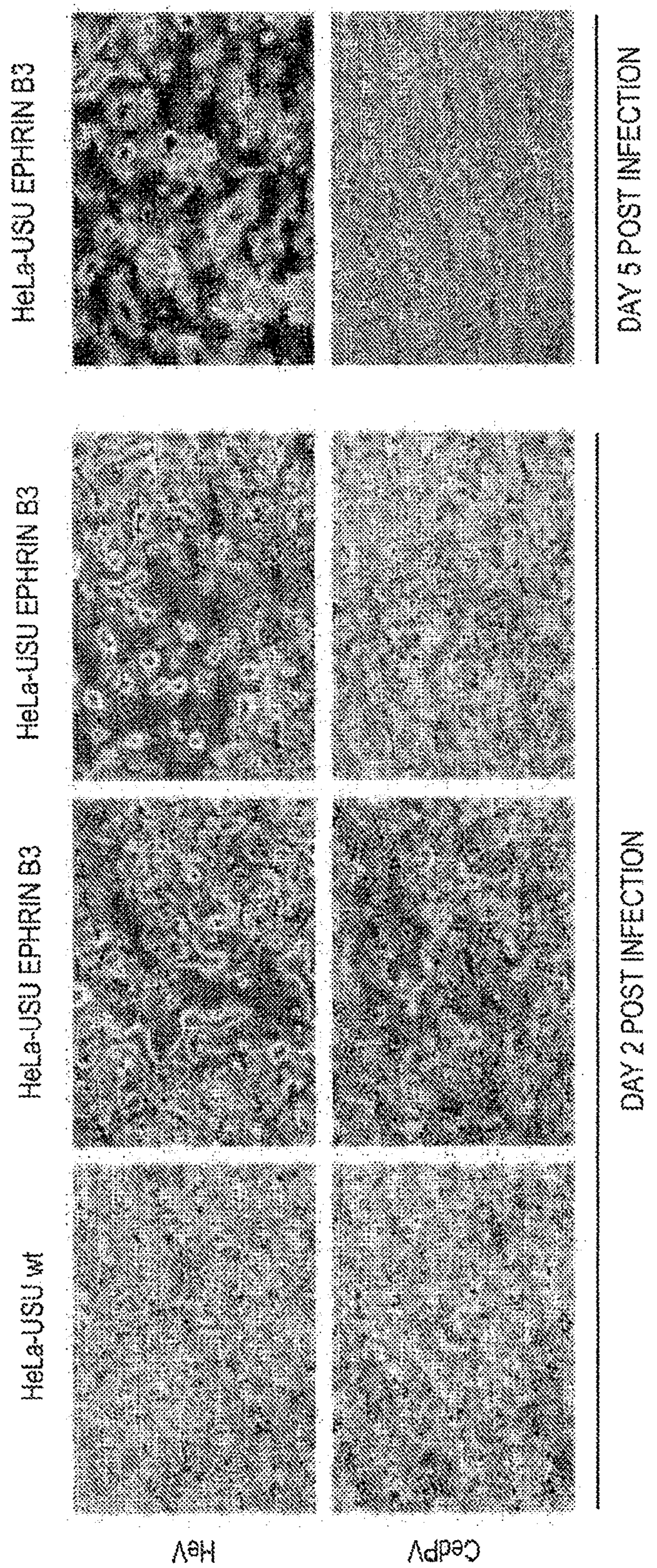
Figure 8A:
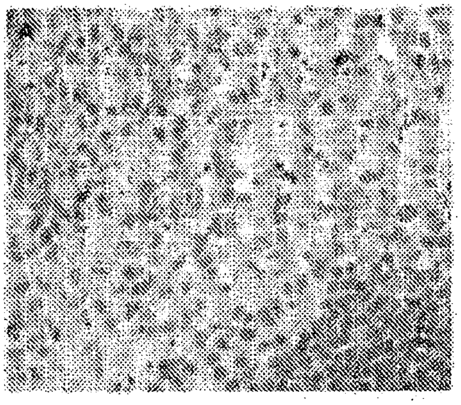
Figure 8B:
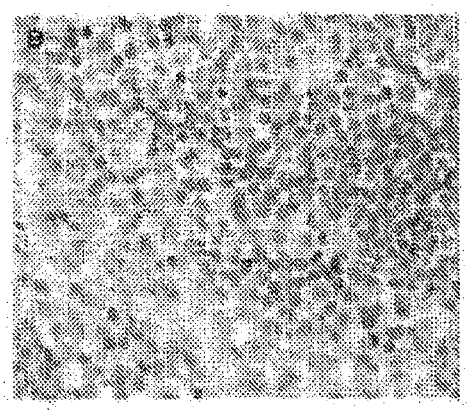
Figure 8C:
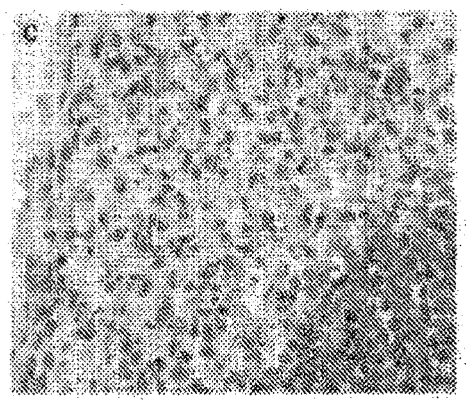
Figure 8D:
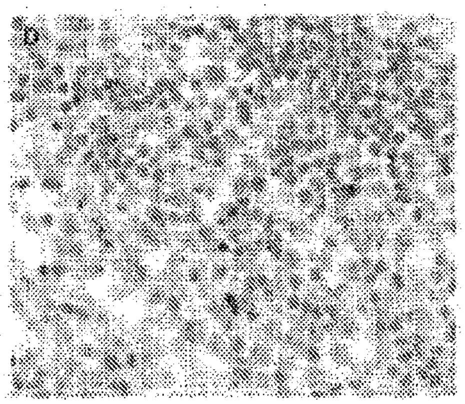

FIG. 7 depicts the functional testing of ephrin-B2 and -B3 as an entry receptor for CedPV. Infection of CedPV into HeLa-USU cells in the presence and absence of ephrin gene products is shown. The susceptibility of infection, as an indirect measurement of receptor function, is demonstrated by the formation of syncytial cytopathic effect (CPE).

FIG. 8 depicts the immunohistochemical analysis of bronchial lymph node of CedPV-infected ferrets. Bronchial lymph node of ferret #2, euthanized on day 6 pi, was stained with rabbit antiserum against recombinant N protein of CedPV (B) and NiV (D), respectively. Bronchial lymph node of an unrelated ferret (infected with influenza H5N1 from another experiment) was used as negative control and stained with the same anti-CedPV (A) and anti-NiV (C) antisera under identical conditions.

Figure 9:
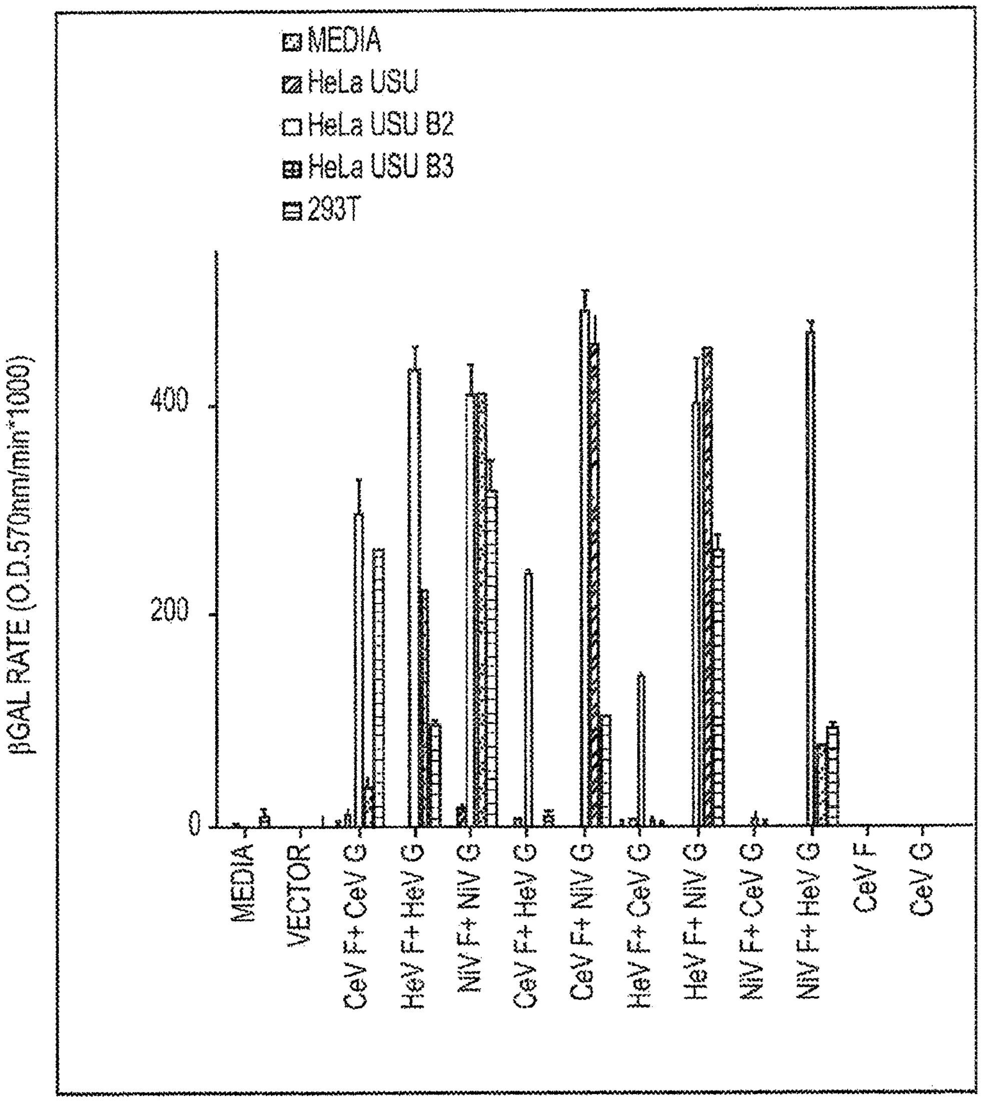

FIG. 9 depicts the results of CedPV glycoprotein mediated cell-cell fusion and heterotypic mixing with HeV and NiV glycoproteins. Various target cell populations are shown in the legend.

Figure 10:
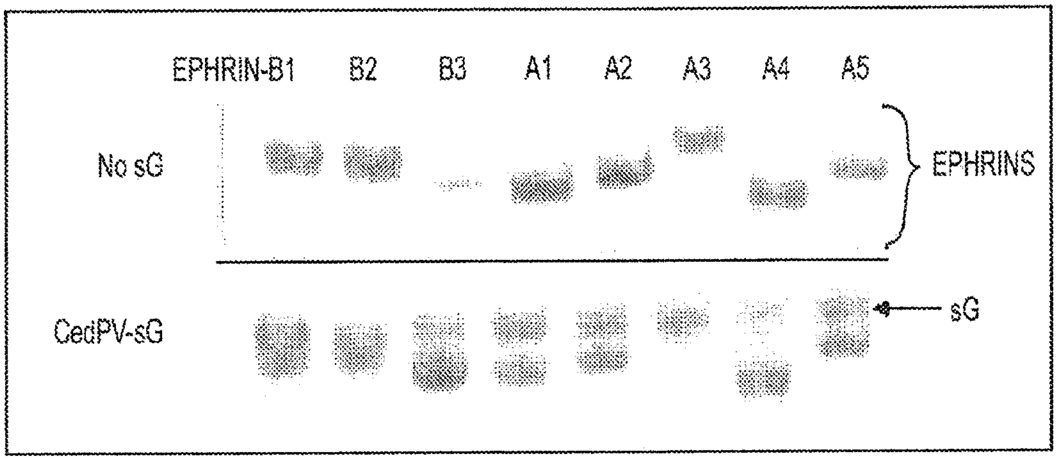

FIG. 10 depicts purified soluble ephrin-FC proteins alone or pre-mixed with CedPV-sG, precipitated and analyzed by SDS-PAGE and coomassie. The separated sG is marked and the different ephrin protein patterns are noted. CedPV-sG and ephrin-B2 run close together in lane 3.

Figure 11:
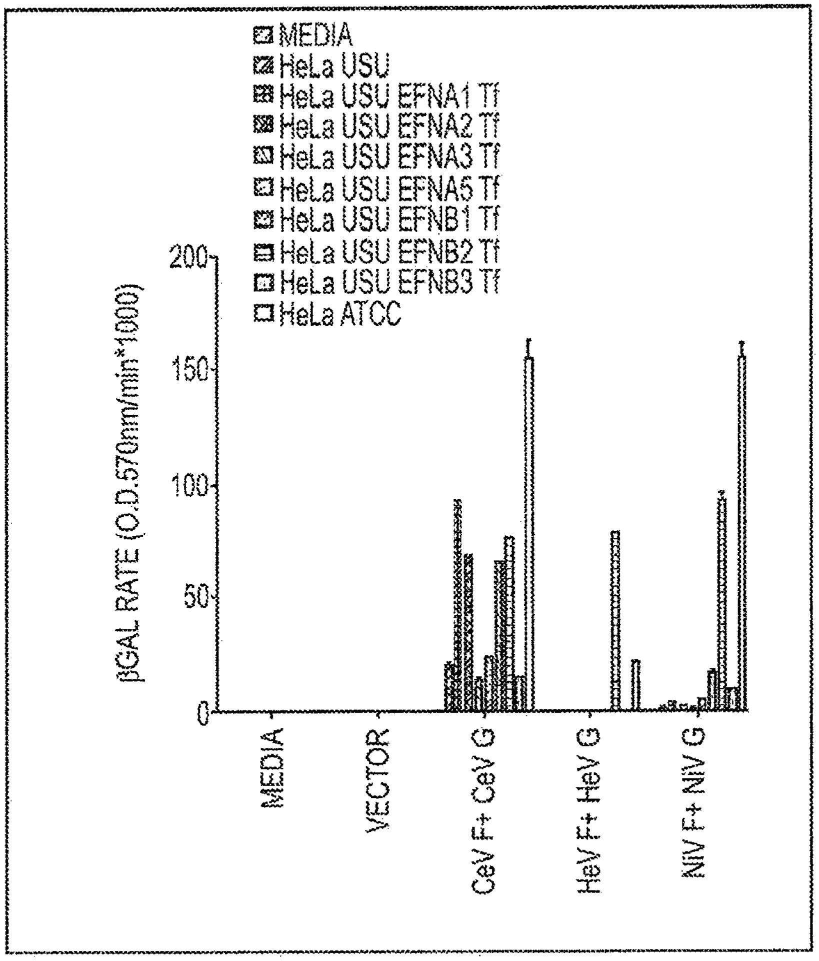

FIG. 11 depicts the results of Hela-USU target cell populations prepared by transfecting in the indicated ephrin receptor constructs and then used in cell-cell fusion assay with effector cells expressing either CedPV, HeV or NiV F and G glycoproteins, and a standard fusion-reporter gene assay was carried out.

DETAILED DESCRIPTION OF THE INVENTION

The present invention is directed towards a novel virus, named Cedar Virus ("CedPV"), and its methods of use. The present invention is also directed towards the individual proteins, and fragments thereof, as well as the coding sequences of the individual proteins that make up the CedPV.

Figure 3A:
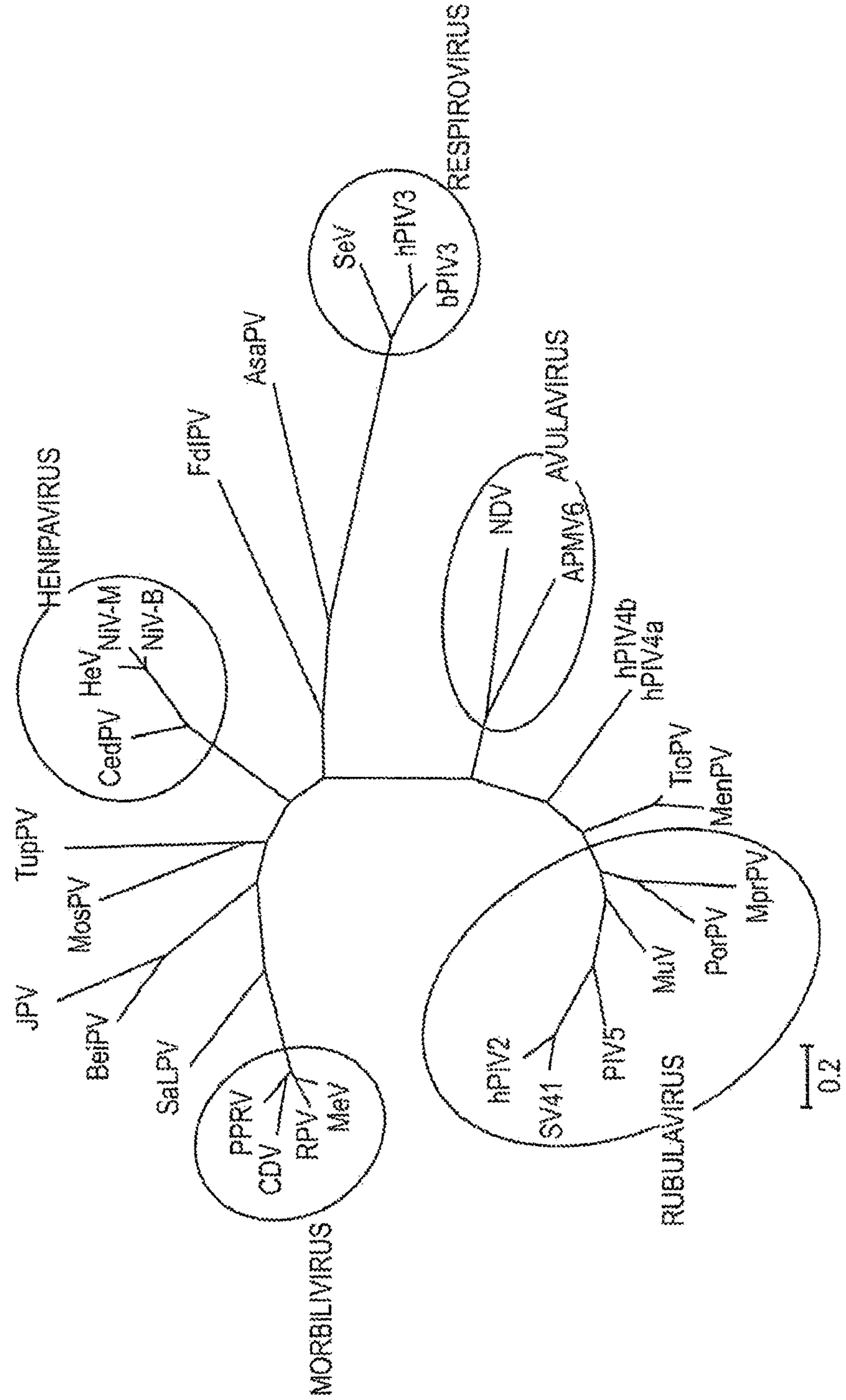
FIG. 3 depicts a phylogenetic tree of selected paramyxoviruses. 2A: The tree is based on the N protein sequences Virus name (abbreviation) and GenBank accession numbers are as follows: Avian paramyxovirus 6 (APMV6) AY029299; Atlantic salmon paramyxovirus (AsaPV) EU156171; Beilong virus (BeiPV) DQ100461; Bovine parainfluenza virus 3 (bPIV3) AF178654; Canine distemper virus (CDV) AF014953; Cedar virus (CedPV) JQ001776; Fer-de-lance virus (FdIPV) AY141760; Hendra virus (Hey) AF017149; Human parainfluenza virus 2 (hPIV2) AF533010; Human parainfluenza virus 3 (hPIV3) Z11575; Human parainfluenza virus 4a (hPIV4a) AB543336; Human parainfluenza virus 4b (hPIV4b) EU627591; J virus (JPV) AY900001; Menangle virus (MenPV) AF326114; Measles virus (MeV) AB016162; Mossman virus (MosPV) AY286409; Mapeura virus (MprPV) EF095490; Mumps virus (MuV) AB000388; Newcastle disease virus (NDV) AF077761; Nipah virus, Bangladesh strain (NiV-B)

The inventors have isolated a novel paramyxovirus, in particular a *Henipavirus*. As is well established, the *Henipavirus* genus belongs to the paramyxovirus family of viruses and includes both the *Hendrvirus* (HeV) and *Nipahvirus* (NiV). In all likelihood, the newly isolated CedPV will belong to the *Henipahvirus* genus based on phylogentic studies, see FIG. 3. Regardless of its classification, the inventors establish herein that CedPV is a novel virus that shares antigenic properties, among other properties, with Hendra virus. The newly discovered CedPV is an RNA virus containing a single strand of RNA.

The genome of the virus is presented herein as SEQ ID NO:1.

```
                                                           (SEQ ID NO: 1)
  1 accagacaaa ggaagtctag tctccggatt aaatcatatt cgtatgatta atcttaggat

 61 cccggtatct agaatctgga tctggattcg gtttaattga attgcgatcg tttataaatt

121 agaaaggaga tttactactc aaaatgtctg acattttcaa tgagactcaa tcatttagaa

181 actatcagtc caacttaggc agagatggca gggccagtgc agcaacgact actttgacaa

241 ctaaagtgag gatctttgtt ccagcgaata ataatccaaa cctcagatgg cgtttaacac

301 tattcttgat ggatgtcgtg aggtcacctg cctccgcaga gtctatgaaa gtgggtgctg

361 ggatatcctt ggtatctatg tatgctgaaa aacccggggc tcttgtgaga gcattattga

421 atgacccaga tgttgaagcg ataatcatag atgtttatgg ctttgatgaa ggtattccta

481 taatggaacg aagaggtgat aaagctacag atgacatgga ttccctaaga aagattgtta

541 aagctgcaca tgatttcagc agaggaagga gtttatttgt tgatcaaagg gtccaggata

601 ttgttatgtc agatatgggg tcatttgtga atgctattac ttccatagag acgcagatat

661 ggattttgat cgcaaaggct gtaactgccc cagatacagc agaagagagc gaaggaagaa

721 gatgggcaaa atatgttcag caaaagaggg ttaatccttt gttcttgatt tctccacaat

781 ggatcaatga catgagatcc ctgattgcgg caagtctttc gcttcgtaaa ttcatggttg
```

-continued

```
 841 aactactgat ggaagctaag aaaggacggg ggacaaaagg aagaataatg gagattgtat
 901 ccgatatcgg aaattacgtt gaagagacag gaatggcagg gttcttcgct acaataaagt
 961 tcggtcttga gaccaaattc cctgctttgg cacttaatga gctccagagt gacttgaaca
1021 caatgaaaag tctcatgata ctgtacagaa gcataggacc aaaggccccc tttatggtgt
1081 tgttggaaga ttcaattcag accaaatttg ctccaggaag ctatccactt ctttggagtt
1141 ttgcgatggg tgtaggcaca actattgaca gagctatggg tgccttgaac attaacagaa
1201 gttatcttga acctgtctat tttaggctag ggcaacaatc agctaaacat caagcaggaa
1261 atgttgacaa agaaatggca gaaaagttag gattgacaga agaccagatc gtgcacctat
1321 cagctaatgt gaaggatgca agtcaaggta gagatgacaa tcaaatcaac atccgagaag
1381 ggaagttcac aaatgttgtt gatgacatcc aggatcatgc ccagagttcc tctgaggatt
1441 acaatcctag taaaaagagt ttctcaatat tgacgagcat cacatccacc gtagatagtg
1501 ctgacagtag gtctgcaatg aatgagtcaa tgacaacaac atccttgctg aaattgagac
1561 agaggctggc agagaagaaa ggagactcca agaacagtca agacacacct ccaaaaccac
1621 ccagagcaaa agatcaaccc actgatgagg tctccttcat ggattccaat atatgatcag
1681 aatgatggtt aaaatcaacc aactaagggc gcgtagagta ccttcagata gaacactaca
1741 ttaatcgggt gaaacaatag atttatgggt ttggtgctta atttttattt aatcttactt
1801 gcaaaacagg cagctgctac actcgtaacc actcctcaca gtaagggcaa cacgggtcat
1861 agaacttatg cctatagatt acctctatct gtatatctag ctatgattaa aatgtatact
1921 tctgctgacc ggttttctag caacagtcca cattattact ttatgggtat tttttaatca
1981 accttttata atcaaatata ttacaaaaaa cttaggatcc aagtggtcca aacttttttt
2041 gatcaagagt catattggct actttaggag gacactttaa acacaaattg ttacaagagg
2101 atattcatca gatggacaaa ctacaattga ttgaagatgg cctctctact atcaatttta
2161 tacaggaaaa taaggaaaaa ttacagcatt cttacggaag atcctccatc agagagccac
2221 ccacaagtgt cagggttgaa gagtgggaga aatttattcg aaagatcgct tctggacctg
2281 aacaagttca agggggagga tctgagactg agatcacagg cgataatgga gatagaggca
2341 attttaccaa tcctgatcag ggaggcggag tcacaggaca attcgaagaa aggtatcaaa
2401 aatgggggtc acaagattca gaattacaac tggacccaat ggttgtacac gatttcttct
2461 atgacgagag aagggagaat cccgacaatg gaaaatatga ccgcagctct aaaaaacggg
2521 ataatatcag agaaggaaca cgacaggata agtacaataa tcagtctact gatgaattac
2581 tgtcctgcct acaaccatct tctaagaacg atgtcatcaa gaatgaaagt acatcagtgt
2641 caaatttgca tgttacagga aataaactga atcctgacgc aaaacccttt gaacccacct
2701 cccagtcgaa agagcaccca accaccacac agcacaacaa aaatgaccat cagaccgatg
2761 atgattataa gaatagaaga tccagtgaaa acaatgtgat ctctgatcat gccaccacaa
2821 tggaagacaa caacaatttt atcccggcga ccaaaagaaa gaatgcattg agcgaaccca
2881 tatacgtcca ggtattgccc tcaaacacag agggtttctc gggaaaagat tatccactcc
2941 tcaaggacaa ctctgtcaag aagcgtgcag agccagtcat cctagaaact gccaaccacc
3001 ctgcaggctc tgccgaccaa gacacaaatc agattgaaga aaacatgcag ttcaaccttc
3061 caaaactgct cacagaagat acagacgatg aaccagagga taacaatgat tccatgcctc
3121 ttgaggaaga cattagagag atcggttcca tgctaaaaga tggaaccaaa gatatcaaga
3181 caaggatgaa tgagatagat gacgcaatca agaagataaa taagaaatca aaaaatagaa
```

-continued

```
3241 gtctggatct agaatcagac ggtaaagatc aggggagaag agatccatca gtagacctcg
3301 ggattaaaaa aagaaaggaa gggctaaagg ccgcaatgca aaagacaaaa gagcaattgt
3361 ctataaaagt ggagagagag attggattga acgacaggat atgtcaaaat tcgaagatga
3421 gtacagaaaa gaaattgata tatgctggga tggaaatgga gtatggacaa acgagtactg
3481 ggtcaggagg tccacaagga tcaaaggatg ggacttctga tgatgtccag gtagacgaag
3541 actacgatga aggggaagac tatgaggcta tgccgtcaga taggttttat acaacattat
3601 caggtgaaca aaaggataga tttgatctag atgctaacca aatgtctcag tatgacctcg
3661 aggcccaggt ggatgaatta accagaatga atctcatact ctattctaga ttagaaacta
3721 ctaataagtt gcttattgac atattagatc tagctaaaga aatgccaaag ttagttagaa
3781 aagtggataa tcttgagaga cagatgggta acttgaatat gttaacctct acccttgagg
3841 gtcacctatc ttctgtaatg attatgatac ccggtaagga taagagcgaa aaggaaatcc
3901 ctaaaaatcc ggacctgaga ccaatactgg ggagaagcaa cacgtcgtta actgatgtta
3961 tcgacctaga ccattaccct gataaaggct ccaaaggtat caaaccaagt ggatctggag
4021 acagacagta catcggctct ctagagagca aattttctat aaatgatgag tacaattttg
4081 ctccataccc tatcagggac gaactcctat tgccaggttt aagagatgac aaaaccaatg
4141 cttcatcgtt catcccagat gacacggaca ggtctccaat ggtgctcaaa ataataattc
4201 gacagaacat ccatgatgaa gaagtgaagg atgagctact gtccatacta gaacaacata
4261 acactgtgga ggaattgaat gaaatatgga atactgtgaa tgattacctc gatggcaaca
4321 tctgattaac agatattgag attgatccta ttctaaacaa gtaatctctg ataatgatag
4381 tatggaataa gaatactaat cacactattg tactcttgta gaatcttaac gagtgtctaa
4441 tgtcagattt tagcaacaca tactaataac ttgtaatcca tttctcctta ttccatttaa
4501 tctcacatta gaaaaaactt aggatcccag atttgcaaag tcaaaacggg atctactatc
4561 aggtgttgga gctaacaata gcggagtctg cataacaaat agcgttcaaa gaagtttgaa
4621 aaccatcata gaatatggat ccgtcagatt tgaggaggat tataatggag gatgataaga
4681 gtctggtcaa caatgatgat agtacagaaa ctgattttct cgagaaaact tggagagaag
4741 ggagtaagat tgacaagatc acaccagagg ttgatgaaaa cgggaatatg gtccccaagt
4801 acgttgtctt caacccgggg aaaaatgaga ggaaaacatc cggatatcaa tatatgattt
4861 gttatggttt cattgaggat ggacctatca atggctcacc aagagtcaaa ggtaatatca
4921 gaaccaccgc ttcttttcct ttgggtgttg gaaaaactta ctcgtctcca gaagagatct
4981 tacaagagct gacaacactc aagatcactg tcagaaggac agccggatca aatgagaagt
5041 tggtgtatgg aataacaggg cctttaaatc acctttaccc gtggtataaa gttttgacag
5101 gtggctccat ttttagtgcg gtgaaggtct gtaggaatgt ggatcaaata ctattagaca
5161 gaccccaaat acttagagta ttctttctaa gtataactaa attaacagat aaaggtgtgt
5221 atatgatacc caaaagtgtt ctcgacttca gatcggataa ttcgatggcc ttcaatctgc
5281 ttgtgtatct caagatagac actgacatca ccaaagcagg catcagaggg attgtcaaca
5341 aagaagggga gaggataacg tcattcatgt tacacatcgg taactttaca agaagaggag
5401 gaaaacatta ctcagtggag tattgcaaaa ggaaaattga caaaatgaag ctcacattcg
5461 ccttaggcac tataggcggt ctaagcttac atatcaggat cgatggaagg ataagtaaaa
5521 ggctccaagc acaagttggc tttcagagaa acatttgcta ctcactaatg gacacaaacc
5581 catggttgaa taaattaacg tggaacaata gttgtgaaat acacaaagtc accgctgtca
5641 ttcagccatc tgtgccaaag gacttcatgt tgtatgagga catcttaata gataatacag
```

-continued

```
5701 gcaagatctt aaaataaagt aggagagtca gtcattaccc agtatattga atactaatga
5761 caactttatt aatccaattc tatctccagt tactagaatt tctaaaacaa ttctactgct
5821 cagcaacgca tctcaaacat tgtgatcttc aattatgatc gacgcattgt aatctatata
5881 gcttttagtt catgaaatac taaaaagggc ttaatcttgt aagttctcag caaatactcc
5941 aatgcaaaag agcgcctcaa catctcaagc agcaccaaaa taaaccacaa tcaatgtgca
6001 acaagagcaa tcgtctaaag tgtgaaaacc aaaatcacag atcagaaagg gcacatattt
6061 cagtcctgta aaaataccaa gtgggattaa taaaagagga tcaatcctta tcattttaag
6121 aaaaacttag gatcccagag atcctaaaga gccaattcct ttatattttg atcttgaagg
6181 gctagaagtc aggctgaaac acagaggtgg aggaacacag gaactaaaat tgatgaaatc
6241 aaccttagct caacatctaa tcaatcaagc ttaagtcatc ctaatactgt atacaaccag
6301 cagcgtagag agtggatttg atttcggcac ccttgcgaag tgaaggctat tactgcctgt
6361 cctttcaatc agaaaattac atttacccat aaagtaatct caacatgtct aacaagagga
6421 caacagtatt gatcataata agctatacgt tattttattt gaataatgca gcaattgtag
6481 ggtttgattt tgataaattg aataaaatag gtgtggtgca agggagagtc ctaaattata
6541 aaattaaagg agatccaatg acaaaagacc ttgtcttgaa atttatccct aacatagtga
6601 atatcactga atgtgtgaga gagcccttga gtaggtacaa tgagaccgtg aggagattgc
6661 ttttacctat acacaacatg cttgggttat acttgaataa cacaaatgct aaaatgactg
6721 ggttgatgat cgcgggtgtg atcatgggtg ggatagcaat aggtatagcc acagcagctc
6781 agatcacagc aggttttgct ctttatgagg caaaaaagaa cacagaaaat attcagaaat
6841 taacagacag catcatgaaa acacaggact cgattgataa acttactgac agtgtgggga
6901 caagcatact tatattgaat aagctacaga catacatcaa caatcaactg gtaccaaatc
6961 tagagcttct atcctgccga caaaacaaaa ttgagtttga tctaatgtta accaagtatt
7021 tggtggatct tatgactgtt attggtccta atatcaataa tcctgttaat aaagatatga
7081 ctattcaatc tttgtcactt ctttttgatg gcaattatga tataatgatg tcagaacttg
7141 gttatacacc tcaggatttc ttagatttga tagagagtaa gagtataaca gggcaaataa
7201 tttatgttga tatggaaaac ttgtacgttg tgatcaggac atatctacct accctaattg
7261 aagtacctga tgcccaaata tatgagttca acaaaataac tatgagtagc aatggaggag
7321 aatacttgtc aaccatacct aatttcatat taataagagg taattatatg tctaatatag
7381 atgttgcaac atgttatatg accaaagcaa gcgtaatttg taatcaagat tattcactcc
7441 cgatgagcca aaacttaaga agctgttatc aaggtgagac agaatactgt cctgttgagg
7501 cagtcatcgc gtcacactct ccaagatttg ctcttacaaa tggagttatt ttcgccaatt
7561 gtataaatac aatttgtagg tgtcaagaca atggtaagac tatcactcaa aacataaacc
7621 aattcgtaag catgatcgac aacagtactt gtaatgatgt catggtagat aagtttacta
7681 tcaaggtagg aaaatatatg gggagaaaag atatcaataa tattaatatc cagataggac
7741 cgcagatcat aattgataag gttgacttgt ctaatgaaat aaacaagatg aatcaatctt
7801 taaaagatag tattttctac ctgagagaag ccaagagaat tttagactca gtaaatatca
7861 gtcttatatc tccaagcgtt caattgtttc taataataat atcagtcctc tcatttatta
7921 tattattgat tatcatagta tacttgtact gtaaatcaaa acattcatat aaatataaca
7981 aatttataga tgatcctgat tattacaatg attacaaaag agaacgtatt aatggcaaag
8041 ccagtaagag taacaatata tattatgtag gtgattaaca atcgataatc taaaggatta
```

-continued

```
8101 cctcactatc actaccaagg taacttccat gtaagatcgg accttccccg aagacattaa
8161 ataaaactta ggatcccaga gtatccctct aagtgatcct tctagattgg ttactgatat
8221 atatacatat ttatcctctt tccgtcgttg tttattgatc attaataatg ctttctcagc
8281 tccaaaaaaa ttacttagac aactcaaacc aacaaggtga taaaatgaac aacccagata
8341 agaaattaag tgtcaacttc aaccctttag aattagataa aggtcaaaaa gatctcaata
8401 agtcttatta tgttaaaaac aagaattata acgtttcaaa tctattaaat gaaagtctgc
8461 acgatatcaa gttttgtatt tattgtatat tctcactgct aattatcatt acaataatca
8521 atataatcac aatatcaatt gttataactc gtctgaaagt acatgaagag aataatggca
8581 tggaatctcc taatttacaa tctattcaag atagtctctc atctcttact aacatgatca
8641 atacagagat aactcctaga atagggattt tagttacagc cacttctgtt actctctctt
8701 catctatcaa ttatgtcggg actaagacaa atcaactggt caatgaatta aaagattata
8761 taaccaaaag ttgtggcttt aaggtccctg aattaaagtt acatgaatgc aacataagtt
8821 gtgctgatcc aaaaaattagc aaatctgcaa tgtacagcac caatgcctat gccgagcttg
8881 ctggtccacc taagatattt tgtaaaagtg tatccaaaga ccccgacttt agactgaagc
8941 agatagatta tgtaatacca gtgcagcaag atcggtctat ttgtatgaac aaccctttat
9001 tggatatttc tgatgggttt tttacctaca tacattatga aggaataaat agctgtaaaa
9061 aatcagattc atttaaagtg ctgctgtcac atggtgaaat agttgacagg ggtgattatc
9121 gaccatcatt atatctatta tcaagtcatt accatcctta ttcaatgcag gtaataaact
9181 gtgtacctgt gacttgtaac cagtcatcct ttgtattctg tcatatctcc aacaacacta
9241 aaacattgga caattcagat tactcgtcag acgagtacta cataacatat ttcaatggca
9301 tagatcgtcc caaaaccaag aagattccca ttaacaatat gacagcagac aatcgttata
9361 tccattttac attctcaggt gggggaggtg tatgtttagg tgaagaattt attattcctg
9421 ttaccacagt catcaatact gatgtattca cgcatgatta ttgtgagagt ttcaactgtt
9481 cagtccaaac cggtaaaagt ctaaaggaga tatgctctga gtcattaaga tctccaacga
9541 actcatcgcg atacaattta aacggaatca tgattataag tcaaaacaac atgacagatt
9601 ttaagattca gttgaatggt ataacttata acaaactgtc attcggaagt cctggaagac
9661 tgagcaagac actgggccag gtcctttatt accaatcttc aatgagttgg gatacttatc
9721 taaaggcagg atttgtcgag aaatggaaac cctttacccc gaattggatg aacaatactg
9781 tgatatccag acctaaccaa ggtaattgtc caaggtatca taaatgcccc gagatatgtt
9841 atggagggac atacaatgat attgctcctt tagatctagg aaaagacatg tatgttagcg
9901 ttattctaga ttcagatcag cttgcagaga atccagagat tacagtattt aactctacta
9961 ctatacttta taaggagaga gtatccaaag atgaactaaa cacaagaagt actacaacga
10021 gctgttttct tttcctagat gaaccttggt gtatatcagt attagaaaca aacagattta
10081 acggcaaatc tattaggccc gagatttatt catacaaaat tcctaagtat tgttaatttg
10141 atgagcttat tcctcatact tcaatcaaat ttaatataac taatatcaaa ttgttgcact
10201 cagctattat taaaactgga tcatcagaca ataaagatgt atacaaagat atatcgaaga
10261 gggtattaaa gaaaacttag gatcccagat ccttcaataa ggcagagcct tgattgtatc
10321 agcgtcattt acaattgaat ctcaattaac aacactgatt aataacttaa gcagaatact
10381 cctattacag tgtttaattg acttaatttt aattgaggat tttataatcc tataattgga
10441 gcagatctaa actctcaccg attcagttct aatcctttat taactaaaga acaaattcta
10501 aataattgga tgacgtcaca ggagacaagc tggaaacaat ttagttagaa ggaagaaacc
```

-continued 10561 ttttaccaga tatggaaagt gactttgata tatctgttag cgacgtactg tacccagaat
10621 gtcatttgga cagtcctata gtcggcggta agctcattac ttctcttgag tatgcgaatt
10681 tgactcataa ccaacctcat gaagatcaga cattgctgac taatataaat gtcaataaaa
10741 agaagaagat aaaaagtcct ctaatatccc aacaatcttt atttggaaat gaggttaata
10801 aggagatttt cgatcttaaa aattattacc atgtccccta tccagaatgt aacagagatt
10861 tattcttaat ctctgatgac aaaatagcat tcaaactcag taaaatcatg gataattcta
10921 ataaactgtt tgatggttta gagaggaaac tgagtcgctt aatttcgaat gtagataatc
10981 aactattaaa tgcaacctct cttcataata attctgagat ggatcggaag ggaaaagaac
11041 atccttgctt cccagaaaag agcacaattg atgatgtaag acagcagaga cagacacgag
11101 attttccaaa gaattcaact agagagggaa gatctccaaa acaccctgat gccggtccta
11161 cacctgaaaa cagtgccaaa aacgatttgc atagagacaa cacagacaat atgccaacag
11221 gccatagttc gacatctatg aaaaaaccta aaatatctgg agaagaatat cttagtatgt
11281 ggctagactc agaggatttg ggttctaaac gaatttctgc acaattaggg aaggatgtat
11341 catgtaaagg ccatctgcac acgacagaag acaaaccgat aatagttcct gacactcgat
11401 atatccaaaa tcatgaatct aataacgata ttttccccaa aaaagagaaa aaattctgca
11461 aacttccacc gtcatcggat aatttaacca aaatcatggt gaattcaaaa tggtacaatc
11521 ctttcctttt ttggtttact gtcaagactg aacttagagc ctgccagaag gagaactaca
11581 aaaggaaaaa cagaaaattg ggaattatca catcgattaa aggttcatgc tataagttga
11641 tactcaacca gaatctagta gcaatattcg aggaagacag cagtggatac tcagatcata
11701 aaaaaagaaa aaaacgatgc tactatctaa ctcccgaaat ggtccttatg ttctccgatg
11761 taactgaagg aagattgatg attgatgttg caatgagatt tgacaaaaag tacaaaactc
11821 tagagaaaaa ggctttgaaa ttatggtttc ttatagacga gttatttcct tctatgggaa
11881 atagagtgta taatattata tccatgcttg agcctttgac tctcgcgata ttacaggtta
11941 aggatgagtc aaggttgttg agaggtgcat tcatgcatca ttgtttaggt gacctcttcg
12001 aagaacttcg agagtccaag aactacccgg aagatgagat caagagattt gccaacgacc
12061 taataaatgt catgacctgt cgggacattc atttagtagc agaattcttc tcattcttta
12121 ggactttcgg acatccaata ttgaacgctc aaactgcagc caggaaagtt agagagtaca
12181 tgttagcaga taaaatcctt gagtacgaac ctatcatgaa aggtcatgcg attttctgtg
12241 ctataatcat aaatggattt agagatagac atggaggagt ttggcctcct cttgatcttc
12301 caaaacattg ttcaaagaac ataatatctc tcaaaaatac aggtgaaggg gtaacttatg
12361 aagtagcaat aaacaattgg agatcatttg tcgggttaaa gttcaaatgt tttatgggtc
12421 tcaatttaga caatgatctc agcatgtaca tgaaagataa agcattatca cctttaaggg
12481 atctttggga ttcaatctat tcacgtgaag taatgtccta ccaaccacct agaaacaaaa
12541 aatcaagaag attggttgag gttttcgttg atgatcagga ctttgatccc gttgatatga
12601 taaattatgt tctgaccgga gaatatctca gagatgatga tttcaatgct tcttatagtt
12661 taaaagagaa agagaccaaa caagttggca ggttgtttgc taagatgact tataaaatga
12721 gggcctgtca agttattgct gagaatttaa ttgcacatgg gattgggaga tatttccatg
12781 aaaacgggat ggttaaggat gagcatgagc tcagcaaatc actgtttcaa ttgtctatat
12841 caggaatacc aagagggaac aaaaacaaca aatcgacgaa cgacacaatc cacgaaagca
12901 agatcgagaa taaccattcc tttaaaaaca tccagaatcg atcatttcga aagacggata -continued

```
12961 acccatacaa tagatttaac attgataacc caactttctt atccccaaac tgtaacccca
13021 agtataaccg taagaattca gagacaatag gtatattctc tcgtgcagaa accaaaagca
13081 tgattagaga acagaaaagt cacagagaag tcaaaataaa taagctagat atcggcagtg
13141 ataatgaaga gcaaggaaaa gagatagatg ccgccaagta caaaatcacg gacaacccaa
13201 atccacacat aaatcctcaa gatcaacccg gaatctgtca agaagacaaa ggcaaagaag
13261 gagcaaagtc agatctcaca gaaggcatga gttttctgga gatgcacaca ctctttaacc
13321 cgagtaagag cgatatcaga acaaatctcg aattggaaaa gagttcactt tcaaaccctg
13381 gatttatatc acaaaaagag aaaagaggca aaacttataa tgaatcccat tcactgggaa
13441 agttctctaa agaggatgaa gaaagatacg atgtcatcag tgcattcctg acaacagatt
13501 tacgaaaatt ctgcttaaat tggagacatg aatcaatcgg catttttgca agaaggatgg
13561 acgaaatcta tggtttgcct ggtttcttta attggatgca cagaagacta gagcgatctg
13621 tgttatatgt tgcggaccct cattgcccgc cgtctatcaa tgaacatatc gatctaaacg
13681 attcacccga aagagacata tttatacatc atccgaaagg gggtatagaa ggatacagcc
13741 aaaaactgtg gacaatagcg actatccctt ttctattcct cagtgctcat gagacaaaca
13801 cccggatagc ggcagttgta caaggtgaca atcaatcaat tgcaattaca cataaggtcc
13861 accctcattt gccttacaaa atgaagaaag aactctctgc aatgcaggca aaaaaatatt
13921 tttcaaggtt acggcacaac atgaaggcat tagggcatga attgaaggcg accgagacta
13981 tcattagtac tcatttcttc atttattcca agaaaatcca ctatgacggg gctgttttat
14041 cacaatctct gaaatcaatg gcaaggtgtg tattttggtc agaaaccctt gttgatgaaa
14101 ctagagcagc atgcagtaat atcagcacaa caattgcaaa ggctattgag aatggttata
14161 gcaggagatc tggctatctg ataaatgttc ttaaaaccat ccaacaaatt aatatatcat
14221 tgagttttaa tataaatgaa tgcatgacag atgacataat cagaccgttt agagataatc
14281 caaactggat caaacatgcc gcattaatcc ccgccagctt gggaggactc aactatatga
14341 acatgtctcg attgtatgtg aggaatatag gggatccagt cacagcatcg atagcagatg
14401 ttaagagaat gattctcggt ggtgtactac ccattggaat actccacaat atcatgttgc
14461 aagaacccgg tgatgccact tatttggact ggtgtagtga tccatactcc atcaacctaa
14521 agcagactca aagtatcaca aaagttataa agaacataac ggcaagagtg atactaagga
14581 attcggtcaa tccactgctc aaaggtctat ttcatgaagg tgcttatgag gaggacactg
14641 aattagcaac attcattttg gacaggagag tcatcttacc acgagtcggt cacgagatct
14701 taaacaactc catcacagga gcaagagaag agatctcggg cttactggat accacaaaag
14761 gattgataag aattggcata gcaaagggag gattaactca gagaacatta tctcgaattt
14821 ccaattatga ttatgaacaa tttttgaacc taatgaatat gttgaagaac aaagaacaaa
14881 acagtgtcat ttccctgtca gcttgctctg ttgactttgc tatagcttta agaagcagga
14941 tgtggaggaa attggcaaaa ggaagattaa tatatggttt agaagtccct gatccaatag
15001 aagcaatgat tggctttctc attcttggga gtgaaaattg tctactctgt gattcaggaa
15061 gcaaaaacta tacctggttt ttcataccaa aggatgtaca gttggataag attgataaag
15121 atcacgcatc aataagggta ccctatgtcg gatcaactac cgaagaaaga tcagagataa
15181 agttaggatc cgtgaaaaat ccaagcaaat ccctgaaatc tgctataaga ctcgcaactg
15241 tgtacacttg ggcatttggc acaagtgatg ctgaatggtg ggaggcttgg tacttgtcta
15301 atcaacgagc aaatataccc ttagatgttc tcaaaacgat aacacctata tctacttcaa
15361 cgaatattgc tcatagatta cgagaccgat caacacaggt taaatacgcc agtacatctc
```

-continued 15421 ttaacagagt atcgcggcat gtaacaatta gtaacgataa catgaatttt gaatttgacg
15481 gggttaaaat ggataccaac ttgatttatc aacaagtcat gctgttaggg ctttcatgct
15541 tggagagttt attccgaaat aggaaaatga caaatagtta caatatcgtg taccatttac
15601 acgttcaaga acattgttgt gtaaaggctc tgaatgattt accttataca ccgtcaacac
15661 atccagtgcc aaattataca gaagttagag ataataggtt aatttacgat cctcaaccta
15721 tattagaatt tgatgagcta agattagcaa ttcagcaaac aaagaaagta gatttggaat
15781 tttcattgtg ggatacaaaa gaacttcatg agaatttagc tcaaagttta gcgattacag
15841 taacggatat tatgacaaaa tctgataaag atcatattaa agaccaaaga agtatagatg
15901 ttgatgataa tattaagaca ctaataactg agtttttatt agtagaccct gaaatgtttg
15961 ccgtaaattt aggattgcat atatcaataa aatggtcatt tgatattcac tttaaaagac
16021 caagaggacg ctatagcatg atagaatact tgactgatct tttggataat acttcttctc
16081 atgtttatcg aatccttact aatgtattat ctcatcccag agttatgaga aaattcacta
16141 atgccgggct actagtaccg aaatacggtc cctaccttac aagtcaagat ttcaaaaaga
16201 tggcggtaga tttcataata acagcgtata ccacattttt gaccaattgg tgtaataata
16261 acaagttttc aattctaata cctgaacaag accctgatat acttgaatta agaaaagaca
16321 tcactcatgc aaggcattta tgtatgatct cggatcttta ctgctactct ttcaagcaac
16381 cttggataaa ggagcttaca ccacaagaga agatctgcgt catggaggac ttcatagcca
16441 attgtgttgc taatgatcaa acaagtgcgg gctggaacat aacgcccctta agagtttaca
16501 atctccctgc atcgaccaca tacatcagga gagggataat aaaacaatta agaatccgtc
16561 aaagcaatga gcctattgat ctggaagata ttaggattgg tcagaacccc gattttgtga
16621 ataaacctat tgagttttgt agcagtgaat tcggtatcac aatttataac cttgaagaaa
16681 ttcttcaatc aaatgtgcat ctcagtgtaa atatgaacat tgactcctca acaagtaaca
16741 atactgaaaa tcatttattt agaagggtag gcttgaactc tacttcatct tataaagcac
16801 tatctttaac acctgttatt aaaagatatc atcaacagaa cactaatagg ctgtttatag
16861 gagaaggatc agggtctatg atgtatcttt accagaaaac cttgggggag acaatatgct
16921 tctttaattc gggagttcag tacaatgagg atctgggtca aagggaacaa tcattatacc
16981 cgagtgaata cagtatctgt gaacaaggag taaaaaaaga aaaccctctc accgggcatg
17041 ttataccact attcaatgga agaccagaaa ccacatgggt aggcaatgat gattctttca
17101 agtatatatt ggaacatact ataaatagag acatcgggct tgttcactcc gatatggaaa
17161 caggaatagg gaaggataat tatactatct taaatgaaca tgcacatctt atagcactga
17221 gccttacagt aatgattgat gatggaatct tggtgtctaa ggtagcttat gcccctgggt
17281 tttgcatctc ttcattattg aatatgtacc ggacattttt ttcattagtt ctatgtgcgt
17341 ttccaccgta tagcaatttt gaatcaactg aattttacct gatttgcttg caaaaaagta
17401 tacccggacc tatcacacca gctagagcca tccaacaaac gacgaagcaa tctagagaag
17461 aggataatag tataactaat aatatcctca aaatcaaaaa tcttgttcag aaagaattta
17521 tcaaaacagt aaagaaaaaa tacgaaatcc atccttcgtt taactgtcct atcaacttca
17581 caaaggatga taaatattta atgagtgttg ggtttcaagc caatggtcct gatatgatac
17641 gtaaagagac gggctatgac ataggtagca atgtagagaa tctccgagat gtcttaatca
17701 agttgtttgc agatgcagtc accttctatg atgatgtcac aaataaaaag aactttttaa
17761 atccttatcc agtctacaca agaactcagt ataaaattct gatggataaa atatgcaaga

```
17821 aagtcacctt atacacctta atcatatcat gtaaaggatc caatcaatat tgctgggaaa

17881 ttaaatccca aataagaaag cattgtctca tacttgattt gaaaagtaag gtttttacaa

17941 aacttattcc aaagggatta agagaaaggg gtgactcaaa agggatgaag agcatatggt

18001 tcactaaact aaccagtcaa gaggtgaaaa gatggtggaa gatgatatct tacatcgtga

18061 taataagcaa tccataacca catccaactt gtcagttaaa cacttaaatc acaataaact

18121 tgtcatcaga ttaaagaaaa cttataattc ccttttttag gt
```

The present invention provides for nucleic acids related to the CedPV genome. In particular, the present invention provides for nucleic acids with a polynucleotide sequence at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the polynucleotide sequence of SEQ ID NO:1.

The present invention also provides for fragments of the polynucleotide of SEQ ID NO:1, for example primers and probes.

The present invention also comprises vectors containing any of the nucleic acids disclosed herein. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired: sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., .beta.-galactosidase or alkaline phosphatase), and genes which visibly affect the phenotype of transformed or transfected cells, hosts, colonies or plaques. Examples of vectors include but are not limited to those capable of autonomous replication and expression of the structural gene products present in the DNA segments to which they are operably joined.

The genomic sequence of SEQ ID NO:1 above codes for the nucleoplasmid protein ("N-protein"), the phosphoprotein ("P-protein"), the matrix protein ("M-protein"), the fusion protein ("F-protein"), the glycoprotein protein or attachment protein ("G-protein") and the large protein ("L-protein") of CedPV. In addition, the P gene also codes for the C-protein of CedPV. The terms "protein" and "polypeptide" are under interchangeably herein and refer to a polymer of amino acids.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids and proteins, the term "isolated" means not found in its native environment and includes but is not limited to such settings: (i) being amplified in vitro by, for example, polymerase chain reaction (PCR); (ii) being recombinantly produced by cloning and/or culturing; (iii) being purified, as by cleavage and gel separation; (iv) being part of a prepared plasmid or expression vector, or (v) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid or protein may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Referring to the nucleotide sequence of SEQ ID NO:1 above, the coding sequence for the N-protein begins at position 144 and ends at 1676, resulting in a polypeptide of 510 amino acids long as disclosed in SEQ ID NO:2. The present invention thus provides for nucleic acids that code for the amino acid sequence of SEQ ID NO:2. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 144-1673 of SEQ ID NO:1.

The invention also provides for polypeptides, derivatives and fragments of the CedPV N-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:2. As used herein, a "derivative" of a reference polypeptide is a polypeptide that has less than 100% amino acid identity with the reference polypeptide. For example, the invention provides for derivatives of the CedPV N-protein as described herein. The invention also provides for polypeptides comprising or consisting of the amino acid sequence of SEQ ID NO:2.

The invention also provides for fragments of the polypeptide of SEQ ID NO:2. As used herein, a fragment of the reference polypeptide is a polypeptide with a length that is less that that of the reference polypeptide. The fragment may be within a larger molecule, such as a chimeric protein, such that the total length of the molecule containing the fragment is larger than the reference protein. The polypeptide fragments of SEQ ID NO:2 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 506, 507, 508 or 509 amino acids in length. As used herein, the length of fragments disclosed above are also used to indicate a polypeptide having a number of amino acids within a certain range. For example, as used herein, a "polypeptide fragment of SEQ ID NO:2 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:2 that is, for example, "at least about . . . 440, 445 . . . amino acids in length" will include polypeptide fragments that are between 440 and 445 amino acids in length.

```
                                        (SEQ ID NO: 2)
MSDIFNETQS FRNYQSNLGR DGRASAATTT LTTKVRIFVP

ANNNPNLRWR LTLFLMDVVR SPASAESMKV GAGISLVSMY

AEKPGALVRA LLNDPDVEAI IIDVYGFDEG IPIMERRGDK

ATDDMDSLRK IVKAAHDFSR GRSLFVDQRV QDIVMSDMGS

FVNAITSIET QIWILIAKAV TAPDTAEESE GRRWAKYVQQ

KRVNPLFLIS PQWINDMRSL IAASLSLRKF MVELLMEAKK

GRGTKGRIME IVSDIGNYVE ETGMAGFFAT IKFGLETKFP

ALALNELQSD LNTMKSLMIL YRSIGPKAPF MVLLEDSIQT

KFAPGSYPLL WSFAMGVGTT IDRAMGALNI NRSYLEPVYF

RLGQQSAKHQ AGNVDKEMAE KLGLTEDQIV HLSANVKDAS
```

-continued

```
QGRDDNQINI REGKFTNVVD DIQDHAQSSS EDYNPSKKSF

SILTSITSTV DSADSRSAMN ESMTTTSLLK LRQRLAEKKG

DSKNSQDTPP KPPRAKDQPT DEVSFMDSNI
```

Referring to the nucleotide sequence of SEQ ID NO:1 above, the coding sequence for the P-protein begins at position 2112 and ends at 4325, resulting in a polypeptide of 737 amino acids long as disclosed in SEQ ID NO:3. The present invention thus provides for nucleic acids that code for the amino acid sequence of SEQ ID NO:3. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 2112-4325 of SEQ ID NO:1.

The invention also provides for nucleic acid molecules encoding the polypeptides, derivatives and fragments of the CedPV P-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:3. The invention also provides for polypeptides comprising or consisting of the amino acid sequence of SEQ ID NO:3.

The polypeptide fragments of SEQ ID NO:3 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 731, 732, 733, 734, 735 or 736 amino acids in length. As used herein, the length of fragments disclosed above are also used to indicate a polypeptide having a number of amino acids within a certain range. For example, as used herein, a "polypeptide fragment of SEQ ID NO:3 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:3 that is, for example, "at least about . . . 720, 725 . . . amino acids in length" will include polypeptide fragments that are between 720 and 725 amino acids in length.

```
                                        (SEQ ID NO: 3)
MDKLQLIEDG LSTINFIQEN KEKLQHSYGR SSIREPPTSV

RVEEWEKFIR KIASGPEQVQ GGGSETEITG DNGDRGNFTN

PDQGGGVTGQ FEERYQKWGS QDSELQLDPM VVHDFFYDER

RENPDNGKYD RSSKKRDNIR EGTRQDKYNN QSTDELLSCL
```

-continued

QPSSKNDVIK NESTSVSNLH VTGNKLNPDA KPFEPTSQSK

EHPTTTQHNK NDHQTDDDYK NRRSSENNVI SDHATTMEDN

NNFIPATKRK NALSEPIYVQ VLPSNTEGFS GKDYPLLKDN

SVKKRAEPVI LETANHPAGS ADQDTNQIEE NMQFNLPKLL

TEDTDDEPED NNDSMPLEED IREIGSMLKD GTKDIKTRMN

EIDDAIKKIN KKSKNRSLDL ESDGKDQGRR DPSVDLGIKK

RKEGLKAAMQ KTKEQLSIKV EREIGLNDRI CQNSKMSTEK

KLIYAGMEME YGQTSTGSGG PQGSKDGTSD DVQVDEDYDE

GEDYEAMPSD RFYTTLSGEQ KDRFDLDANQ MSQYDLEAQV

DELTRMNLIL YSRLETTNKL LIDILDLAKE MPKLVRKVDN

LERQMGNLNM LTSTLEGHLS SVMIMIPGKD KSEKEIPKNP

DLRPILGRSN TSLTDVIDLD HYPDKGSKGI KPSGSGDRQY

IGSLESKFSI NDEYNFAPYP IRDELLLPGL RDDKTNASSF

IPDDTDRSPM VLKIIIRQNI HDEEVKDELL SILEQHNTVE

ELNEIWNTVN DYLDGNI

The coding sequence for the C-protein is within the P-protein coding sequence and begins at position 2137 (of SEQ ID NO:1) and ends at position 2670, resulting in a polypeptide of 177 amino acids long as disclosed in SEQ ID NO:4. The present invention thus provides for nucleic acids that code for the amino acid sequence of SEQ ID NO:4. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 2137-2670 of SEQ ID NO:1.

The invention also provides for nucleic acid molecules encoding the polypeptides, derivatives and fragments of the CedPV C-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:4. The invention also provides for polypeptides comprising or consisting of the amino acid sequence of SEQ ID NO:4.

The polypeptide fragments of SEQ ID NO:4 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 166, 167m 168, 169, 170, 171, 172, 173, 174, 175 or 176 amino acids in length. As used herein, the length of fragments disclosed above are also used to indicate a polypeptide having a number of amino acids within a certain range. For example, as used herein, a "polypeptide fragment of SEQ ID NO:4 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:4 that is, for example, "at least about . . . 140, 145 . . . amino acids in length" will include polypeptide fragments that are between 140 and 145 amino adds in length.

(SEQ ID NO: 4)

MASLLSILYR KIRKNYSILT EDPPSESHPQ VSGLKSGRNL

FERSLLDLNK FKGEDLRLRS QAIMEIEAIL PILIREAESQ

DNSKKGIKNG GHKIQNYNWT QWLYTISSMT REGRIPTMEN

MTAALKNGII SEKEHDRIST IISLLMNYCP AYNHLLRTMS

SRMKVHQCQI CMLQEIN

Referring to the nucleotide sequence of SEQ ID NO:1 above, the coding sequence for the M-protein begins at position 4635 and ends at 5717, resulting in a polypeptide of 360 amino acids long as disclosed in SEQ ID NO:5. The present invention thus provides for nucleic acids that code for the amino acid sequence of SEQ ID NO:5. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 4635-5717 of SEQ ID NO:1.

The invention also provides for nucleic acid molecules encoding the polypeptides, derivatives and fragments of the CedPV M-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:5. The invention also provides for polypeptides comprising or consisting of the amino acid sequence of SEQ ID NO:5.

The polypeptide fragments of SEQ ID NO:5 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 351, 352, 353, 354, 355, 356, 357, 358 or 359 amino acids in length. As used herein, the length of fragments disclosed above are also used to indicate a polypeptide having a number of amino acids within a certain range. For example, as used herein, a "polypeptide fragment of SEQ ID NO:5 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:5 that is, for example, "at least about . . . 280, 285 . . . amino acids in length" will include polypeptide fragments that are between 280 and 285 amino acids in length.

(SEQ ID NO: 5)

MDPSDLRRII MEDDKSLVNN DDSTETDFLE KTWREGSKID

KITPEVDENG NMVPKYVVFN PGKNERKTSG YQYMICYGFI

EDGPINGSPR VKGNIRTTAS FPLGVGKTYS SPEEILQELT

TLKITVRRTA GSNEKLVYGI TGPLNHLYPW YKVLTGGSIF

SAVKVCRNVD QILLDRPQIL RVFFLSITKL TDKGVYMIPK

-continued

SVLDFRSDNS MAFNLLVYLK IDTDITKAGI RGIVNKEGER

ITSFMLHIGN FTRRGGKHYS VEYCKRKIDK MKLTFALGTI

GGLSLHIRID GRISKRLQAQ VGFQRNICYS LMDTNPWLNK

LTWNNSCEIH KVTAVIQPSV PKDFMLYEDI LIDNTGKILK

Referring to the nucleotide sequence of SEQ ID NO:1 above, the coding sequence for the F-protein begins at position 6405 and ends at 8078, resulting in a polypeptide of 557 amino acids long as disclosed in SEQ ID NO:6. The present invention thus provides for nucleic acids that code for the amino acid sequence of SEQ ID NO:6. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 6405-8078 of SEQ ID NO:1.

The invention also provides for nucleic acid molecules encoding the polypeptides, derivatives and fragments of the CedPV F-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:6. The invention also provides for polypeptides comprising or consisting of the amino acid sequence of SEQ ID NO:6.

The polypeptide fragments of SEQ ID NO:6 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 546, 547, 548, 549, 550, 551, 552, 553, 554, 555 or 556 amino acids in length. As used herein, the length of fragments disclosed above are also used to indicate a polypeptide having a number of amino acids within a certain range. For example, as used herein, a "polypeptide fragment of SEQ ID NO:6 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:6 that is, for example, "at least about . . . 515, 520 . . . amino acids in length" will include polypeptide fragments that are between 515 and 520 amino acids in length.

(SEQ ID NO: 6)

MSNKRTTVLI IISYTLFYLN NAAIVGFDFD KLNKIGVVQG

RVLNYKIKGD PMTKDLVLKF IPNIVNITEC VREPLSRYNE

TVRRLLLPIH NMLGLYLNNT NAKMTGLMIA GVIMGGIAIG

IATAAQITAG FALYEAKKNT ENIQKLTDSI MKTQDSIDKL

TDSVGISILI LNKLQTYINN QLVPNLELLS CRQNKIEFDL

MLTKYLVDLM TVIGPNINNP VNKDMTIQSL SLLFDGNYDI

MMSELGYTPQ DFLDLIESKS ITGQIIYVDM ENLYVVIRTY

LPTLIEVPDA QIYEFNKITM SSNGGEYLST IPNFILIRGN

YMSNIDVATC YMTKASVICN QDYSLPMSQN LRSCYQGETE

YCPVEAVIAS HSPRFALTNG VIFANCINTI CRCQDNGKTI

TQNINQFVSM IDNSTCNDVM VDKFTIKVGK YMGRKDINNI

NIQIGPQIII DKVDLSNEIN KMNQSLKDSI FYLREAKRIL

DSVNISLISP SVQLFLIIIS VLSFIILLII IVYLYCKSKH

SYKYNKFIDD PDYYNDYKRE RINGKASKSN NIYYVGD

One example of a fragment of an F protein is a soluble CedPV F glycoprotein comprising all or part of the extracellular domain of F glycoprotein of CedPV. The soluble forms of F glycoprotein may be produced by deleting all or part of the transmembrane and/or cytoplasmic tail domains of the F glycoprotein. By way of example, a soluble F glycoprotein may comprise the complete extracellular region of a CePV F glycoprotein. In some embodiments, the soluble F glycoprotein may be truncated at after K490 in SEQ ID NO:6 Also, by way of example, a soluble F glycoprotein may comprise all or part of the extracellular region and part of the transmembrane domain of a CedPV F glycoprotein. By way of further example, several versions of a soluble F (sF) glycoprotein can be constructed, primarily through removing the cytoplasmic tail and/or transmembrane domain that anchor the protein. As used herein, "soluble F glycoprotein" or "soluble form of F glycoprotein" or "sF glycoprotein" refers to an amino acid sequence for a fragment or portion of native F glycoprotein that contains the extracellular domain or a portion thereof. The sF glycoprotein is structurally similar to the native viral F glycoprotein.

The sF glycoproteins of the invention are structurally similar to the native viral F glycoprotein. By way of example, the sF glycoproteins of the invention may be recognized by polyclonal antibodies directed to CedPV. By way of example, the sF glycoproteins of the invention may assemble in the oligomeric form or forms (such as a trimer), comparable to native CedPV F glycoprotein.

The sF or sG glycoproteins of the present invention are suitable, for example, for vaccine development and for acting as an antigen to generate anti-viral antibodies when used as a vaccine or in the isolation of recombinant monoclonal antibodies. The sF or sG glycoproteins are suitable to generate antibodies capable of recognizing native F or G glycoprotein. The sF or sG glycoproteins of the present invention that assemble in monomeric or oligomeric forms, such as trimers, can be of further use, such as, for example, for crystallization and structural determination to provide further information to aid structural-based antiviral research. The oligomeric forms of sF or sG glycoprotein of the present invention may also generate further antibodies capable of recognizing native F or G glycoprotein and its native oligomeric forms. The term "soluble" has no bearing on the protein's ability to dissolve in an aqueous or non-aqueous solvent.

Referring to the nucleotide sequence of SEQ ID NO:1 above, the coding sequence for the G-protein begins at position 8268 and ends at 10136, resulting in a polypeptide of 622 amino acids long as disclosed in SEQ ID NO:7. The present invention thus provides for nucleic acids that code for the amino acid sequence of SEQ ID NO:7. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 8268-10136 of SEQ ID NO:1.

The invention also provides for nucleic acid molecules encoding the polypeptides, derivatives and fragments of the CedPV G-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:7. The invention also provides for polypeptides comprising or consisting of the amino acid sequence of SEQ ID NO:7.

The polypeptide fragments of SEQ ID NO:7 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 612, 613, 614, 615, 616, 617, 618, 619, 620 or 621 amino acids in length. As used herein, the length of fragments disclosed above are also used to indicate a polypeptide having a number of amino acids within a certain range. For example, as used herein, a "polypeptide fragment of SEQ ID NO:7 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:7 that is, for example, "at least about . . . 300, 305 . . . amino acids in length" will include polypeptide fragments that are between 300 and 305 amino acids in length.

```
                                        (SEQ ID NO: 7)
MLSQLQKNYL DNSNQQGDKM NNPDKKLSVN FNPLELDKGQ

KDLNKSYYVK NKNYNVSNLL NESLHDIKFC IYCIFSLLII

ITIINIITIS IVITRLKVHE ENNGMESPNL QSIQDSLSSL

TNMINTEITP RIGILVTATS VTLSSSINYV GTKINQLVNE

LKDYITKSCG FKVPELKLHE CNISCADPKI SKSAMYSTNA

YAELAGPPKI FCKSVSKDPD FRLKQIDYVI PVQQDRSICM

NNPLLDISDG FFTYIHYEGI NSCKKSDSFK VLLSHGEIVD

RGDYRPSLYL LSSHYHPYSM QVINCVPVTC NQSSFVFCHI

SNNTKTLDNS DYSSDEYYIT YFNGIDRPKT KKIPINNMTA

DNRYIHFTFS GGGGVCLGEE FIIPVTTVIN TDVFTHDYCE

SFNCSVQTGK SLKEICSESL RSPTNSSRYN LNGIMIISQN
```

-continued

```
NMTDFKIQLN GITYNKLSFG SPGRLSKTLG QVLYYQSSMS

WDTYLKAGFV EKWKPFTPNW MNNTVISRPN QGNCPRYHKC

PEICYGGTYN DIAPLDLGKD MYVSVILDSD QLAENPEITV

FNSTTILYKE RVSKDELNTR STTTSCFLFL DEPWCISVLE

TNRFNGKSIR PEIYSYKIPK YC
```

Examples of fragments of G proteins CedPV include soluble forms of CedPV G-protein that retain characteristics of the native viral G glycoprotein allowing for rapid high throughput production of vaccines, diagnostics and screening.

Soluble forms of CedPV G glycoproteins comprise at least a portion of the ectodomain (e.g. extracellular) of the G glycoprotein. In select embodiments, CedPV are generally produced by deleting all or part of the transmembrane domain of the G glycoprotein and all or part of the cytoplasmic tail of the G glycoprotein. In one embodiment, the soluble G protein of CedPV does not comprise any portion of the cytoplasmic region of the full length G protein. In another embodiment, the soluble G protein of CedPV does not comprise any portion of the transmembrane domain. In yet another embodiment, the soluble G protein of CedPV comprises no portion of the transmembrane domain and the cytoplasmic domain. As used herein, the term "soluble" simply means that the G protein is missing a portion or all of its cytoplasmic tail or that the G protein is missing all or part of its transmembrane domain, or both. In some embodiments, the soluble G glycoprotein is truncated after K87 in SEQ ID NO:7. The term "soluble" has no bearing on the protein's ability to dissolve in an aqueous or non-aqueous solvent.

The soluble CedPV G glycoproteins of the invention, generally retain one or more characteristics of the corresponding native viral glycoprotein, such as, ability to interact or bind the viral host cell receptor, can be produced in monomeric and/or oligomeric form or forms, or the ability to elicit antibodies (including, but not limited to, viral neutralizing antibodies) capable of recognizing native G glycoprotein. Examples of additional characteristics include, but are not limited to, the ability to block or prevent infection of a host cell. Conventional methodology may be utilized to evaluate soluble CedPV G glycoproteins for one of more of the characteristics. Examples of methodology that may be used include, but are not limited to, the assays described herein in the Examples.

Referring to the nucleotide sequence of SEQ ID NO:1 above, the coding sequence for the L-protein begins at position 10572 and ends at 18077, resulting in a polypeptide of 2501 amino acids long as disclosed in SEQ ID NO:8. The present invention thus provides for nucleic acids that code for the amino acid sequence of SEQ ID NO:8. In addition, the present invention also provides for nucleic acids with a polynucleotide sequence that is at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polynucleotide sequence of positions 10572-18077 of SEQ ID NO:1.

The invention also provides for nucleic acid molecules encoding the polypeptides, derivatives and fragments of the CedPV L-protein. Specifically, the present invention provides for polypeptides at least about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical to the polypeptide of SEQ ID NO:8. The invention also provides for polypeptides comprising or consisting of the amino acid sequence of SEQ ID NO:8.

The polypeptide fragments of SEQ ID NO:8 can be fragments of at least about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495, 1500, 1505, 1510, 1515, 1520, 1525, 1530, 1535, 1540, 1545, 1550, 1555, 1560, 1565, 1570, 1575, 1580, 1585, 1590, 1595, 1600, 1605, 1610, 1615, 1620, 1625, 1630, 1635, 1640, 1645, 1650, 1655, 1660, 1665, 1670, 1675, 1680, 1685, 1690, 1695, 1700, 1705, 1710, 1715, 1720, 1725, 1730, 1735, 1740, 1745, 1750, 1755, 1760, 1765, 1770, 1775, 1780, 1785, 1790, 1795, 1800, 1805, 1810, 1815, 1820, 1825, 1830, 1835, 1840, 1845, 1850, 1855, 1860, 1865, 1870, 1875, 1880, 1885, 1890, 1895, 1900, 1905, 1910, 1915, 1920, 1925, 1930, 1935, 1940, 1945, 1950, 1955, 1960, 1965, 1970, 1975, 1980, 1985, 1990, 1995, 2000, 2005, 2010, 2015, 2020, 2025, 2030, 2035, 2040, 2045, 2050, 2055, 2060, 2065, 2070, 2075, 2080, 2085, 2090, 2095, 2100, 2105, 2110, 2115, 2120, 2125, 2130, 2135, 2140, 2145, 2150, 2155, 2160, 2165, 2170, 2175, 2180, 2185, 2190, 2195, 2200, 2205, 2210, 2215, 2220, 2225, 2230, 2235, 2240, 2245, 2250, 2255, 2260, 2265, 2270, 2275, 2280, 2285, 2290, 2295, 2300, 2305, 2310, 2315, 2320, 2325, 2330, 2335, 2340, 2345, 2350, 2355, 2360, 2365, 2370, 2375, 2380, 2385, 2390, 2395, 2400, 2405, 2410, 2415, 2420, 2425, 2430, 2435, 2440, 2445, 2450, 2455, 2460, 2465, 2470, 2475, 2480, 2485, 2490, 2491, 2492, 2593, 2494, 2495, 2496, 2497, 2498, 2499 or 2500 amino acids in length. As used herein, the length of fragments disclosed above are also used to indicate a polypeptide having a number of amino acids within a certain range. For example, as used herein, a "polypeptide fragment of SEQ ID NO:8 can be fragment of at least about 15, 20, 25, 30 . . . amino acids in length" is used to mean that the fragments can be between 15 and 20 amino acids in length, and that the fragments can be between 20 and 25 amino acids in length, etc. One of skill in the art will recognize that a polypeptide fragment of SEQ ID NO:8 that is, for example, "at least about . . . 2050, 2055 . . . amino acids in length" will include polypeptide fragments that are between 2050 and 2055 amino acids in length.

(SEQ ID NO: 8)

```
MESDFDISVS DVLYPECHLD SPIVGGKLIT SLEYANLTHN
QPHEDQTLLT NINVNKKKKI KSPLISQQSL FGNEVNKEIF
DLKNYYHVPY PECNRDLFLI SDDKIAFKLS KIMDNSNKLF
DGLERKLSRL ISNVDNQLLN ATSLHNNSEM DRKGKEHPCF
PEKSTIDDVR QQRQTRDFPK NSTREGRSPK HPDAGPTPEN
SAKNDLHRDN TDNMPTGHSS TSMKKPKISG EEYLSMWLDS
EDLGSKRISA QLGKDVSCKG HLHTTEDKPI IVPDTRYIQN
HESNNDIFPK KEKKFCKLPP SSDNLTKIMV NSKWYNPFLF
WFTVKTELRA CQKENYKRKN RKLGIITSIK GSCYKLILNQ
NLVAIFEEDS SGYSDHKKRK KRCYYLTPEM VLMFSDVTEG
RLMIDVAMRF DKKYKTLEKK ALKLWFLIDE LFPSMGNRVY
NIISMLEPLT LAILQVKDES RLLRGAFMHH CLGDLFEELR
ESKNYPEDEI KRFANDLINV MTCRDIHLVA EFFSFFRTFG
HPILNAQTAA RKVREYMLAD KILEYEPIMK GHAIFCAIII
NGFRDRHGGV WPPLDLPKHC SKNIISLKNT GEGVTYEVAI
NNWRSFVGLK FKCFMGLNLD NDLSMYMKDK ALSPLRDLWD
SIYSREVMSY QPPRNKKSRR LVEVFVDDQD FDPVDMINYV
LTGEYLRDDD FNASYSLKEK ETKQVGRLFA KMTYKMRACQ
VIAENLIAHG IGRYFHENGM VKDEHELSKS LFQLSISGIP
RGNKNNKSTN DTIHESKIEN NHSFKNIQNR SFRKTDNPYN
RFNIDNPTFL SPNCNPKYNR KNSETIGIFS RAETKSMIRE
QKSHREVKIN KLDIGSDNEE QGKEIDAAKY KITDNPNPHI
NPQDQPGICQ EDKGKEGAKS DLTEGMSFLE MHTLFNPSKS
DIRTNLELEK SSLSNPGFIS QKEKRGKTYN ESHSLGKFSK
EDEERYDVIS AFLTIDLRKF CLNWRHESIG IFARRMDEIY
GLPGFFNWMH RRLERSVLYV ADPHCPPSIN EHIDLNDSPE
RDIFIHHPKG GIEGYSQKLW TIATIPFLFL SAHETNTRIA
AVVQGDNQSI AITHKVHPHL PYKMKKELSA MQAKKYFSRL
RHNMKALGHE LKATETIIST HFFIYSKKIH YDGAVLSQSL
KSMARCVFWS ETLVDETRAA CSNISTTIAK AIENGYSRRS
GYLINVLKTI QQINISLSFN INECMTDDII RPFRDNPNWI
KHAALIPASL GGLNYMNMSR LYVRNIGDPV TASIADVKRM
ILGGVLPIGI LHNIMLQEPG DATYLDWCSD PYSINLKQTQ
SITKVIKNIT ARVILRNSVN PLLKGLFHEG AYEEDTELAT
FILDRRVILP RVGHEILNNS ITGAREEISG LLDTTKGLIR
IGIAKGGLTQ RTLSRISNYD YEQFLNLMNM LKNKEQNSVI
SLSACSVDFA IALRSRMWRK LAKGRLIYGL EVPDPIEAMI
```

-continued

```
GFLILGSENC LLCDSGSKNY TWFFIPKDVQ LDKIDKDHAS
IRVPYVGSTT EERSEIKLGS VKNPSKSLKS AIRLATVYTW
AFGTSDAEWW EAWYLSNQRA NIPLDVLKTI TPISTSTNIA
HRLRDRSTQV KYASTSLNRV SRHVTISNDN MNFEFDGVKM
DTNLIYQQVM LLGLSCLESL FRNRKMTNSY NIVYHLHVQE
HCCVKALNDL PYTPSTHPVP NYTEVRDNRL IYDPQPILEF
DELRLAIQQT KKVDLEFSLW DTKELHENLA QSLAITVTDI
MTKSDKDHIK DQRSIDVDDN IKTLITEFLL VDPEMFAVNL
GLHISIKWSF DIHFKRPRGR YSMIEYLTDL LDNTSSHVYR
ILTNVLSHPR VMRKFTNAGL LVPKYGPYLT SQDFKKMAVD
FIITAYTTFL TNWCNNNKFS ILIPEQDPDI LELRKDITHA
RHLCMISDLY CYSFKQPWIK ELTPQEKICV MEDFIANCVA
NDQTSAGWNI TPLRVYNLPA STTYIRRGII KQLRIRQSNE
PIDLEDIRIG QNPDFVNKPI EFCSSEFGIT IYNLEEILQS
NVHLSVNMNI DSSTSNNTEN HLFRRVGLNS TSSYKALSLT
PVIKRYHQQN TNRLFIGEGS GSMMYLYQKT LGETICFFNS
GVQYNEDLGQ REQSLYPSEY SICEQGVKKE NPLTGHVIPL
FNGRPETTWV GNDDSFKYIL EHTINRDIGL VHSDMETGIG
KDNYTILNEH AHLIALSLTV MIDDGILVSK VAYAPGFCIS
SLLNMYRTFF SLVLCAFPPY SNFESTEFYL ICLQKSIPGP
ITPARAIQQT TKQSREEDNS ITNNILKIKN LVQKEFIKTV
KKKYEIHPSF NCPINFTKDD KYLMSVGFQA NGPDMIRKET
GYDIGSNVEN LRDVLIKLFA DAVTFYDDVT NKKNFLNPYP
VYTRTQYKIL MDKICKKVTL YTLIISCKGS NQYCWEIKSQ
IRKHCLILDL KSKVFTKLIP KGLRERGDSK GMKSIWFTKL
TSQEVKRWWK MISYIVIISN P
```

A polypeptide having an amino acid sequence at least, for example, about 95% "identical" to a reference an amino acid sequence, e.g., SEQ ID NO:7, is understood to mean that the amino acid sequence of the polypeptide is identical to the reference sequence except that the amino acid sequence may include up to about five modifications per each 100 amino acids of the reference amino acid sequence. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., *Current Protocols in Protein Science*, Vol 1, John Wiley & Sons, Inc. (2000), which is incorporated by reference.

In one embodiment of the present invention, the algorithm used to determine identity between two or more polypeptides is BLASTP. In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and reference sequences are amino sequences. The result of sequence alignment is in percent identity. In one embodiment, parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the reference sequence is shorter or longer than the query sequence because of N-terminus or C-terminus additions or deletions, but not because of internal additions or deletions, a manual correction can be made, because the FASTDB program does not account for N-terminus and C-terminus truncations or additions of the reference sequence when calculating percent identity. For query sequences truncated at the N- or C-termini, relative to the reference sequence, the percent identity is corrected by calculating the number of residues of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the reference sequence that extend past the N- or C-termini of the query sequence may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue query sequence is aligned with a 100 residue reference sequence to determine percent identity. The deletion occurs at the N-terminus of the query sequence and therefore, the FASTDB alignment does not show a match/alignment of the first 10 residues at the N-terminus. The 10 unpaired residues represent 10% of the reference sequence (number of residues at the N- and C-termini not matched/total number of residues in the reference sequence) so 10% is subtracted from the percent identity score calculated by the FASTDB program. If the remaining 90 residues were perfectly matched (100% alignment) the final percent identity would be 90% (100% alignment—10% unmatched overhang). In another example, a 90 residue query sequence is compared with a 100 reference sequence, except that the deletions are internal deletions. In this case the percent identity calculated by FASTDB is not manually corrected, since there are no residues at the N- or C-termini of the subject sequence that are not matched/aligned with the query. In still another example, a 110 amino acid query sequence is aligned with a 100 residue reference sequence to determine percent identity. The addition in the query occurs at the N-terminus of the query sequence and therefore, the FASTDB alignment may not show a match/alignment of the first 10 residues at the N-terminus. If the remaining 100 amino acid residues of the query sequence have 95% identity to the entire length of the reference sequence, the N-terminal addition of the query would be ignored and the percent identity of the query to the reference sequence would be 95%.

As used herein, the terms "correspond(s) to" and "corresponding to," as they relate to sequence alignment, are intended to mean enumerated positions within the reference protein, e.g., CedPV G protein, and those positions in the modified CedPV G protein that align with the positions on the reference protein. Thus, when the amino acid sequence of a subject CedPV G protein is aligned with the amino acid sequence of a reference CedPV G protein, e.g., SEQ ID NO:7, the amino acids in the subject sequence that "correspond to" certain enumerated positions of the reference sequence are those that align with these positions of the reference sequence, e.g., SEQ ID NO:7, but are not necessarily in these exact numerical positions of the reference sequence. Methods for aligning sequences for determining corresponding amino acids between sequences are described herein. Accordingly, the invention provides novel peptides whose sequences correspond to the sequence of SEQ ID NO:7.

Variants resulting from insertion of the polynucleotide encoding a protein disclosed herein into an expression vector system are also contemplated. For example, variants (usually insertions) may arise from when the amino terminus and/or the carboxy terminus of a modified protein is/are fused to another polypeptide.

In another aspect, the invention provides deletion variants wherein one or more amino acid residues in the modified protein are removed. Deletions can be effected at one or both termini of the modified protein, or with removal of one or more non-terminal amino acid residues of the modified protein. Deletion variants, therefore, include all fragments of the modified protein.

Within the confines of the disclosed percent identity, the invention also relates to substitution variants of disclosed polypeptides of the invention. Substitution variants include those polypeptides wherein one or more amino acid residues of a modified protein are removed and replaced with alternative residues. In one aspect, the substitutions are conservative in nature; however, the invention embraces substitutions that are also non-conservative. Conservative substitutions for this purpose may be defined as set out in the tables below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE I

Conservative Substitutions

| SIDE CHAIN CHARACTERISTIC | AMINO ACID |
|---|---|
| Aliphatic | |
| Non-polar | G, A, P, I, L, V |
| Polar - uncharged | C, S, T, M, N, Q |
| Polar - charged | D, E, K, R |
| Aromatic | H, F, W, Y |
| Other | N, Q, D, E |

Alternatively, conservative amino acids can be grouped as described in Lehninger, [Biochemsitry, Second Edition; Worth Publishers, Inc. NY, N.Y. (1975), pp. 71 77] as set out below.

TABLE II

Conservative Substitutions

| SIDE CHAIN CHARACTERISTIC | AMINO ACID |
|---|---|
| Non-polar (hydrophobic) | |
| A. Aliphatic: | A, L, I, V, P |
| B. Aromatic: | F, W |
| C. Sulfur-containing: | M |
| D. Borderline: | G |
| Uncharged-polar | |
| A. Hydroxyl: | S, T, Y |
| B. Amides: | N, Q |
| C. Sylfhydryl: | C |
| D. Borderline: | G |
| Positively Charged (Basic): | K, R, H |
| Negatively Charged (Acidic) | D, E |

And still other alternative, exemplary conservative substitutions are set out below.

TABLE III

Conservative Substitutions

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |

TABLE III-continued

| Conservative Substitutions | |
|---|---|
| Original Residue | Exemplary Substitution |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

It should be understood that the definition of peptides or polypeptides of the invention is intended to include polypeptides bearing modifications other than insertion, deletion, or substitution of amino acid residues. By way of example, the modifications may be covalent in nature, and include for example, chemical bonding with polymers, lipids, other organic and inorganic moieties. Such derivatives may be prepared to increase circulating half-life of a polypeptide, or may be designed to improve the targeting capacity of the polypeptide for desired cells, tissues or organs. Similarly, the invention further embraces modified peptides that have been covalently modified to include one or more water-soluble polymer attachments such as polyethylene glycol, polyoxyethylene glycol or polypropylene glycol.

The present invention is also directed to antibodies or fragments thereof that specifically bind to CedPV or fragments of any of the CedPV proteins disclosed herein.

In particular, the present invention provides antibodies or antibody fragments that bind to the four hydrophobic pockets in the head of the G glycoprotein of the Cedar virus. The antibodies may be monoclonal or polyclonal. Cedar virus likely begins the infection process by binding to the ephrin B2 transmembrane protein that is present on at least endothelial cells, among others. Specifically, the ephrin B2 protein contains a "GH-loop region" that inserts into the 4 hydrophobic binding pockets on the head of the G glycoprotein of Cedar virus, thus allowing the virus to bind specifically to the cell surface protein and begin the infection process. The contact residues of Cedar virus that bind the ephrin B2 are V507, F458 and I401, with the letters referring to the standard one-letter abbreviation of standard amino acids and the numbering referring to the amino acid numbering of SEQ ID NO:7 according to the sequences disclosed herein. As such, the present invention provides antibodies or antibody fragments that bind the non-linear epitope of Cedar virus defined by V507/F458/1401, provided the antibodies or antibody fragments, provided that the antibodies are not any of the antibodies disclosed in PCT/US05/040050 and PCT/US12/35806 which are hereby incorporated by reference in their entirety.

For example, antibodies encompassed by the present invention, include, but are not limited to, antibodies specific for CedPV G glycoprotein, antibodies that cross react with Hendra Virus G glycoprotein and/or Nipah Virus G Glycoprotein and neutralizing antibodies. By way of example a characteristic of a neutralizing antibody includes, but is not limited to, the ability to block or prevent infection of a host cell. The antibodies of the invention may be characterized using methods well known in the art.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. Examples of antibodies are derived from murine, rat, human, primate, or any other origin (including chimeric or humanized antibodies).

Methods of preparing monoclonal and polyclonal antibodies are well known in the art. Polyclonal antibodies can be raised in a mammal, for example, by one or more injections of an immunizing agent and, if desired an adjuvant. Examples of adjuvants include, but are not limited to, keyhole limpet, hemocyanin, serum albumin, bovine thyroglobulin, soybean trypsin inhibitor, Freund complete adjuvant and MPL-TDM adjuvant. The immunization protocol can be determined by one of skill in the art.

The antibodies may alternatively be monoclonal antibodies. Monoclonal antibodies may be produced using hybridoma methods (see, e.g., Kohler, B. and Milstein, C. (1975) Nature 256:495-497 or as modified by Buck, D. W., et al., In Vitro, 18:377-381 (1982).

If desired, the antibody of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody (e.g., genetically manipulate the antibody sequence to obtain greater affinity to the G glycoprotein and/or greater efficacy in inhibiting the fusion of a Cedar Virus, Hendra or Nipah virus to the host cell receptor.).

The antibodies may also be humanized by methods known in the art. See, for example, U.S. Pat. Nos. 4,816,567; 5,807,715; 5,866,692; 6,331,415; 5,530,101; 5,693,761; 5,693,762; 5,585,089; and 6,180,370, which are incorporated by reference. In yet another embodiment, fully human antibodies may be obtained by using commercially available mice that have been engineered to express specific human immunoglobulin proteins.

In another embodiment, antibodies may be made recombinantly and expressed using any method known in the art. By way of example, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro. Phage display can be performed in a variety of formats; for review see, e.g., Johnson, Kevin S, and Chiswell, David J., Current Opinion in Structural Biology 3:564-571 (1993). By way of example, a soluble G glycoprotein as described herein may be used as an antigen for the purposes of isolating recombinant antibodies by these techniques.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol 13:65 (1995); and Pollock, et al., J Immunol Methods 231:147 (1999), which are incorporated by reference. Methods for making derivatives of antibodies, e.g., humanized, single chain, etc. are known in the art.

The antibodies of the invention can be bound to a carrier by conventional methods, for use in, for example, isolating or purifying CedPV G glycoproteins or detecting Hendra or Nipah G glycoproteins in a biological sample or specimen. Alternatively, by way of example, the neutralizing antibodies of the invention may be administered as passive immunotherapy to a subject infected with or suspected of being infected with Hendra, Nipah and/or Cedar virus. The terms "subject" and "patient" are used interchangeably and include but are not limited to humans, simians, farm animals, sport animals and pets. Veterinary uses are also encompassed by the invention.

Diagnostics

The proteins, protein fragment and/or antibodies of the invention may be used in a variety of immunoassays for Cedar virus. The recombinant expressed protein fragments of the invention can be produced with high quality control and are suitable as a antigen for the purposes of detecting antibody in biological samples. By way of example, and not limitation, a soluble CedPV G glycoprotein could be used as an antigen in an ELISA assay to detect antibody in a biological sample from a subject.

The nucleic acids, including primers and probes, of the invention are also be used in a variety of assays for Cedar virus. The primers and probes of the invention are used to detect the presence of ribonucleic acids encoding the Cedar virus in a subject. The present invention also includes a method for detecting the presence of Cedar virus utilizing nucleic acid amplification techniques, for example reverse transcriptase-PCR methods, utilizing repeated cycles of denaturations, primer annealing and extension carried out with DNA polymerase, for example Taq polymerase, to lead to exponential increases in derived nucleic acid, so as to facilitate detection of the presence of the virus.

Vaccines

This invention also relates to vaccines for Cedar virus. In one aspect the vaccines are DNA based vaccines. One skilled in the art is familiar with administration of expression vectors to obtain expression of an exogenous protein in vivo. See, e.g., U.S. Pat. Nos. 6,436,908; 6,413,942; and 6,376,471. Viral-based vectors for delivery of a desired polynucleotide and expression in a desired cell are well known in the art and non-limiting examples are described herein. In another aspect, the vaccines are protein-based and comprise one or more fragments of the proteins or protein fragment of the invention. Examples of protein fragments include but are not limited to ectodomains, transmembranes domains, cytoplasmic domains and functional portions thereof, as well as portions that are specifically reactive to neutralizing antibodies. Vaccines may also be antibody-based vaccines for more immediate treatment as well as prophylaxis against infection.

Administration of expression vectors includes but is not limited to local or systemic administration, including injection, oral administration, particle gun or catheterized administration, and topical administration. Targeted delivery of therapeutic compositions containing an expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Non-viral delivery vehicles and methods can also be employed, including, but not limited to, polyeationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) (all of which are incorporated by reference) and nucleic charge neutralization or fusion with cell membranes. Naked DNA can also be employed. Exemplary naked DNA introduction methods are described in PCT Publication No. WO 90/11092 and U.S. Pat. No. 5,580,859, which are incorporated by reference. Liposomes that can act as gene delivery vehicles are described in U.S. Pat. No. 5,422,120; PCT Publication Nos. WO 95/13796; WO 94/23697; WO 91/14445; and EP 0524968, which are incorporated by reference. Additional approaches are described in Philip, Mol. Cell. Biol. (1994) 14:2411, and in Woffendin, Proc. Natl. Acad. Sci. (1994) 91:1581, which are incorporated by reference.

For human administration, codons comprising a polynucleotide encoding a protein or fragment thereof may be optimized for human use.

In another aspect of the invention, a soluble CedPV G glycoprotein is used as a subunit vaccine. The soluble CedPV glycoprotein or combination thereof may be administered by itself or in combination with an adjuvant. Examples of adjuvants include, but are not limited, aluminum salts, water-in-soil emulsions, oil-in-water emulsions, saponin, QuilA and derivatives, iscoms, liposomes, cytokines including gamma interferon or interleukin 12, DNA, microencapsulation in a solid or semi-solid particle, Freunds complete and incomplete adjuvant or active ingredients thereof including muramyl dipeptide and analogues, DEAE dextran/mineral oil, Alhydrogel, Auspharm adjuvant, and Algammulin.

The subunit vaccine comprising soluble CedPV G glycoprotein or combinations thereof can be administered orally, intravenously, subcutaneously, intraarterially, intramuscularly, intracardially, intraspinally, intrathoracically, intraperitoneally, intraventricularly, sublingually, and/or transdermally.

Dosage and schedule of administration can be determined by methods known in the art. Efficacy of the soluble CedPV G glycoprotein or combinations thereof as a vaccine for Cedar, Hendra, Nipah or related *Henipavirus* viruses may also be evaluated by methods known in the art.

EXAMPLES

Example 1

Urine (approximately 0.5-1 ml) was collected off plastic sheets placed underneath a colony of flying foxes (predominantly *Pteropus alecto* with some *P. Poliocephalus* in the mixed population) in Cedar Grove, South East Queensland, Australia and pooled into 2 ml tubes containing 0.5 ml of viral transport medium (SPGA: a mix of sucrose, phosphate, glutamate and albumin plus penicillin, streptomycin and fungizone). The tubes were temporarily stored on ice after collection and transported to a laboratory in Queensland, frozen at −80° C. The samples were thawed at 4° C. and centrifuged at 16,000×g for 1 min to pellet debris. Urine in the supernatant (approximately 0.5-1 ml) was diluted 1:10 in cell culture media.

The diluted urine was centrifuged at 1,200×g for 5 min and split evenly over Vero, PaKi, PaBr, PaSp and PaPI cell monolayers in 75-$cm^2$ tissue culture flasks. Cell lines used this study were Vero (ATCC), HeLa-USU (22), and the *P. alecto* primary cell lines derived from kidney (PaKi), brain (PaBr), (spleen) PaSp and placenta (PaPI). Cells were grown in Dulbecco's Modified Eagle's Medium Nutrient Mixture F-12 Ham supplemented with double strength antibiotic-antimycotic (Invitrogen), 10 μg/ml ciprofloxacin (MP Biomedicals) and 10% fetal calf serum at 37° C. in the presence of 5% $CO_2$. The flasks were rocked for 2 h at 37° C., 14 ml of fresh cell culture media was added and then incubated for 7 days at 37° C. The flasks were observed daily for toxicity, contamination, or viral cytopathic effect (CPE).

Syncytial CPE was observed in kidney cell (PaKi) monolayers 5 days post inoculation (dpi) with two different urine samples. No CPE was observed in any of the four other cell lines. Supernatant harvested 6 dpi was used to inoculate fresh PaKi cell monolayers. After two passages in PaKi cells, the virus was able to infect and cause CPE in Vero cells. The CPE morphology of the virus, however, in Vero cells was different from that of HeV infection. Further analysis using HeV-specific PCR primers indicated that the new bat virus was not an isolate of HeV.

Example 2

Cells from Example 1 showing syncytial CPE were screened using published broadly reactive primers (31) for all known paramyxoviruses and a subset of paramyxoviruses. PCR products were gel extracted and cloned into pGEM T-Easy (Promega) to facilitate sequencing using M13 primers. Sequences were obtained and aligned with known paramyxovirus sequences allowing for initial classification.

The entire genomic sequence was analyzed using a combination of 454 sequencing (43) and conventional Sanger sequencing. Virions from tissue culture supernatant were collected by centrifugation at 30,000×g for 60 min and resuspended in 140 μl of PBS and mixed with 560 μl of freshly made AVL for RNA extraction using QIAamp Viral RNA mini kit (Qiagen). Synthesis of cDNA and random amplification was conducted using a modification of a published procedure (44). Briefly, cDNA synthesis was performed using a random octomer-linked to a 17-mer defined primer sequence: (5'-GTTTCCCAGTAGGTCTCNNN -3'; SEQ ID NO: 12) and SuperScript III Reverse Transcriptase (Life Technologies). 8 μl of ds-cDNA was amplified in 200 μl PCR reactions with hot-start Taq polymerase enzyme (Promega) and 5'-A*G*C*A*CTGTAGGTTTCCCAGTAGGTCTC-3' (SEQ ID NO: 13; * denotes thiol modifications) as amplification primers for 40 cycles of 95° C/1 min, 48° C/1 min, 72° C/1 min after an initial denaturation step of 5 min at 95° C. and followed by purification with the QIAquick PCR purification kit (Qiagen). Sample preparation for Roche 454 sequencing (454 Life Sciences Branford, Conn., USA) was performed according to the manufacturer's suggested protocol (Rapid Library Preparation and emPCR Lib-L SV).

To obtain an accurate CedPV genome sequence, 454 generated data (after removing low quality, ambiguous and adapter sequences) was analysed by both de novo assembly and read mapping of raw reads onto the CedPV draft genome sequence derived from Sanger sequencing. For 454 read mapping, SNPs and DIPs generated with the CLC software were manually assessed for accuracy by visualising the mapped raw reads (random PCR errors are obvious compared to real SNPs and DIPs especially when read coverage is deep). Consensus sequences for both 454 de novo and read mapping assembly methods were then compared to the Sanger sequence with the latter used to resolve conflicts within the low coverage regions as well as to resolve 454 homopolymer errors.

Sequences of genome termini were determined by 3'- and 5'-RACE using a previously published protocol (45). Briefly, approximately 100 ng of RNA was ligated with adaptor DT88 (see reference for sequence information) using T4 RNA ligase (Promega) followed by cDNA synthesis using the SuperScript III RT kit (Life Technologies) and an adaptor-specific primer, DT89. PCR amplification was then carried out using DT89 and one or more genome-specific primers. PCR products were sequenced directly using either DT89 or genome specific primers by an in-house service group on the ABI Sequencer 3100.

The CLC Genomics Workbench v4.5.1 (CLC Inc, Aarhus, Denmark) was used to trim 454 adapter and cDNA/PCR primer sequences, to remove low quality, ambiguous and small reads <15 bp and to perform de novo and read mapping assemblies all with default parameters. Clone Manager Professional version 9.11 (Scientific and Educational Software, Cary, N.C., USA) was used to join overlapping contigs generated by de novo assembly. Phylogenetic trees were constructed using the neighbor-joining algorithm with bootstrap values determined by 1,000 replicates in the MEGA4 software package (46).

Considering the formation of syncytial CPE by this new virus and the previous success in isolating paramyxoviruses from bat urine, paramyxovirus family-specific and genus-specific primers were used to determine whether this new virus was a member of the family Paramyxoviridae. Positive PCR fragments of the expected sizes were obtained from the Paramyxovirinae and Respirovirus/Morbillivirus/Henipavirus primer sets developed by Tong et al (31).

Sequencing of the PCR products indicated that it was a new paramyxovirus most closely related to HeV and NiV. Based on these preliminary data, the virus was named Cedar virus (CedPV) after the location of the bat colony sampled.

Figure 1:
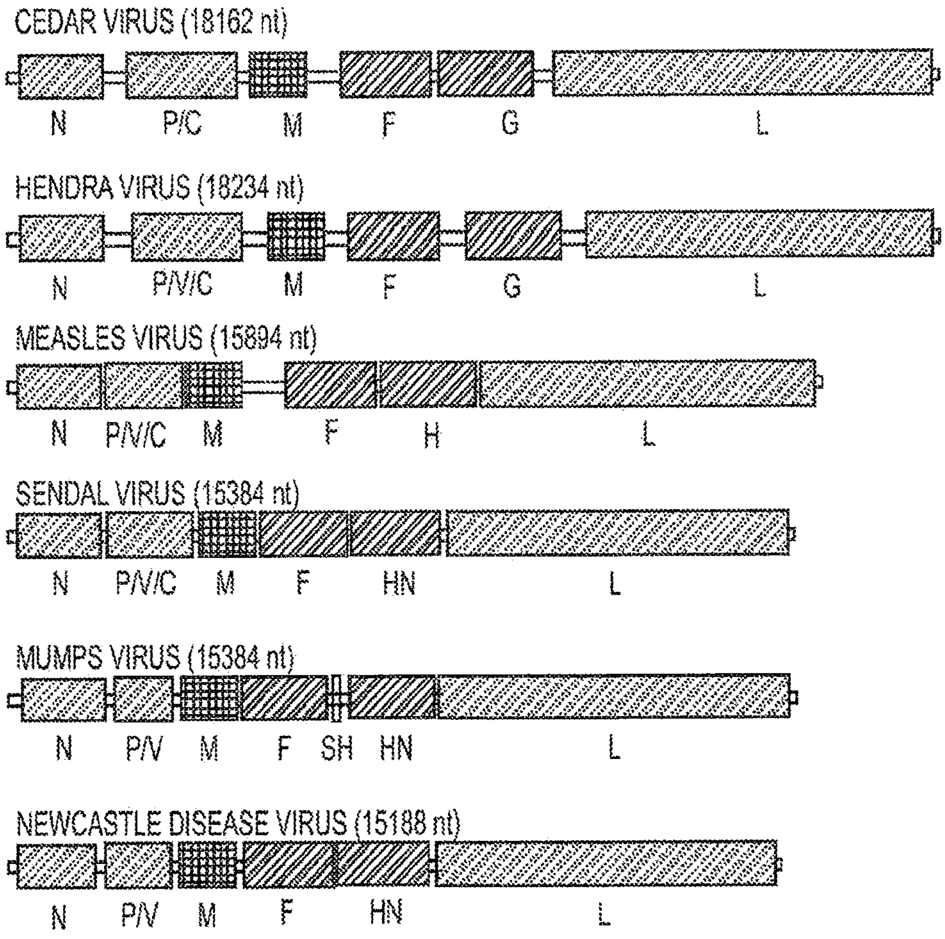
FIG. 1 depicts the genome sizes and organization of CedPV compared to those of the prototype viruses of the five existing genera in the subfamily Paramyxovirinae. Each of the coding and non-coding regions is drawn to scale. The six major genes present in all paramyxovirus genomes are indicated as follows: shaded=RNA polymerase and nucleocapsid genes (N, P and L); slanted=envelope membrane protein genes (F and attachment protein); dotted=matrix protein (M). The small in the genome of the mumps virus represents the gene (SH) not commonly shared among members of the subfamily.

As shown in FIG. 1, the genome of CedPV is 18,162 nt in length and is most similar to that of HeV in the family. The full genome sequence has been deposited to GenBank (Accession No. JQ001776). The genome size is a multiple of 6, which is in perfect agreement with the Rule-of-Six observed for all known members of the subfamily *Paramyxovirinae* (3). The genome of CedPV has a 3-nt intergenic sequence of CTT absolutely conserved at all seven positions and highly conserved gene start and stop signals similar to those present in HeV and NiV (FIG. 2).

Also similar to the HeV genome is the presence of relatively large non-coding regions in the CedPV genome (FIG. 1 and Table 1). The overall protein-coding capacity of the CedPV genome is 87.41% which is higher than HeV at 82.12%. As the genome size of CedPV and HeV is very similar, the increased coding capacity of CedPV is attributed to an increase in protein sizes for five of the six major proteins, with the L protein being 257-aa larger (Table 1). At 2,501 aa, the CedPV L protein is the largest, not only in the family Paramyxoviridae but also for all known viruses in the order Mononegavirale.

TABLE 1

| Comparison of common genes among CedPV, HeV and NiV | | | | | | |
|---|---|---|---|---|---|---|
| | | Open Reading Frame | | | Length of Untranslated Regions (nt) | |
| Gene | Virus | Length (aa) | % sequence identity to CedPV | % sequence identity to HeV | 5' UTR | 3'UTR |
| N | CedPV | 510 | | | 88 | 334 |
| | HeV | 532 | 58 | | 57 | 568 |
| | NiV | 532 | 59 | 92 | 57 | 586 |
| P | CedPV | 737 | | | 98 | 192 |
| | HeV | 707 | 25 | | 105 | 469 |
| | NiV | 709 | 27 | 65 | 105 | 469 |
| C | CedPV | 177 | | | | |
| | HeV | 166 | 26 | | | |
| | NiV | 166 | 25 | 83 | | |
| M | CedPV | 359 | | | 114 | 408 |
| | HeV | 352 | 60 | | 100 | 200 |
| | NiV | 352 | 60 | 89 | 100 | 200 |
| F | CedPV | 557 | | | 276 | 88 |
| | HeV | 546 | 42 | | 272 | 418 |
| | NiV | 546 | 43 | 87 | 284 | 412 |
| G | CedPV | 622 | | | 98 | 139 |
| | HeV | 604 | 29 | | 233 | 516 |
| | NiV | 602 | 30 | 78 | 233 | 504 |
| L | CedPV | 2501 | | | 293 | 63 |
| | HeV | 2244 | 50 | | 153 | 67 |
| | NiV | 2244 | 50 | 86 | 153 | 67 |

Figure 3B:
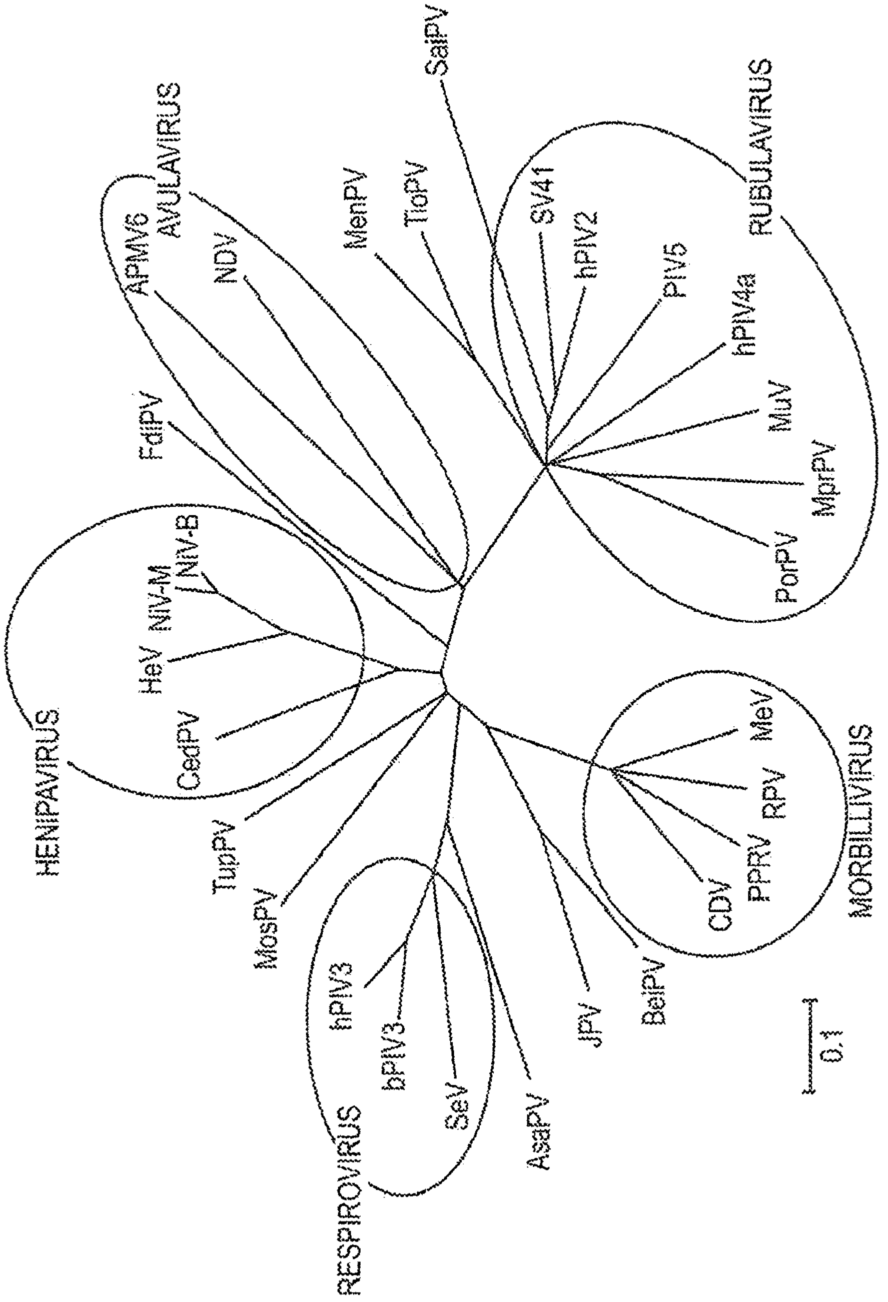
Figure 3C:
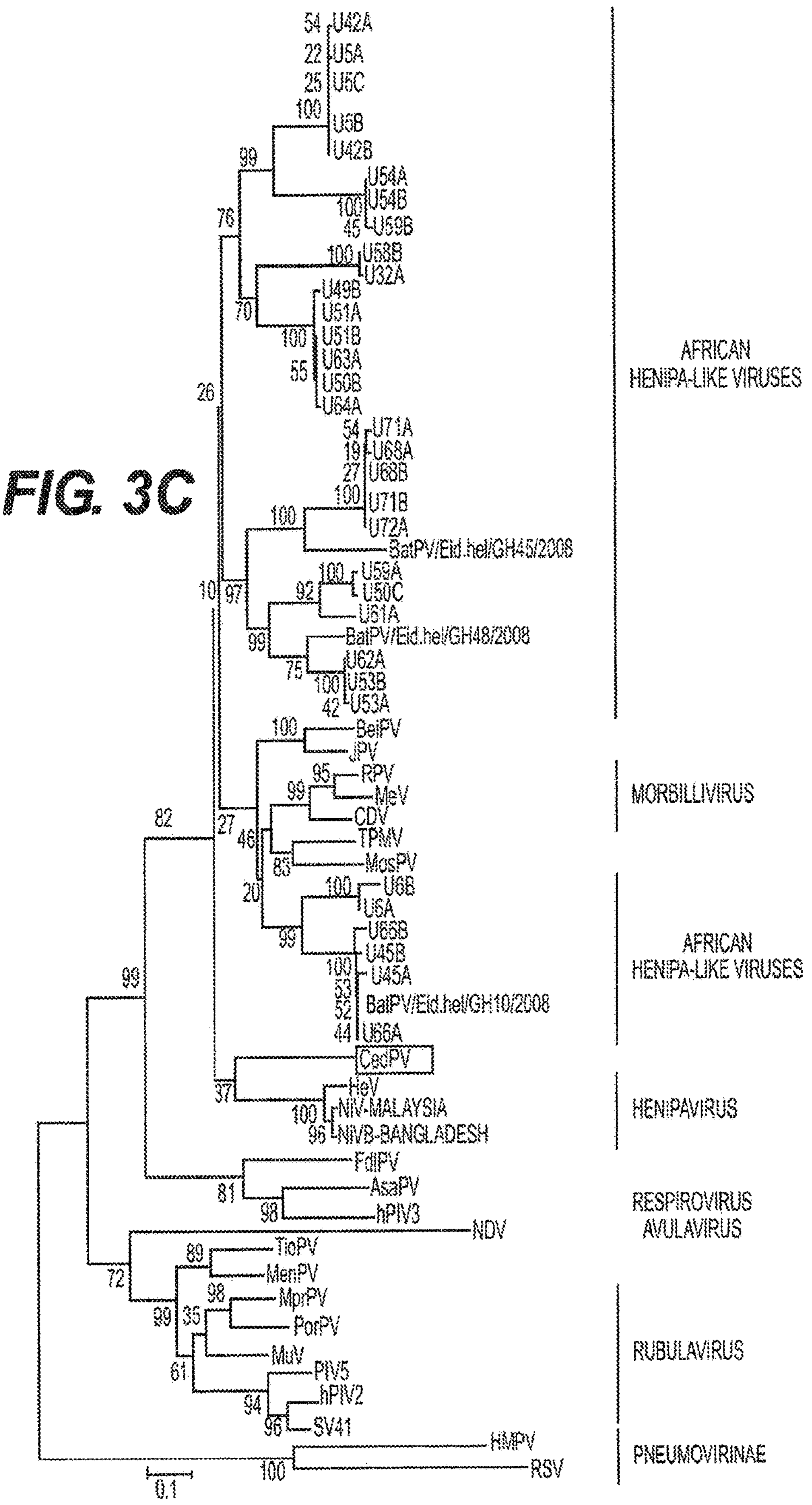

Phylogenetic analysis based on the full length genome sequence and the deduced amino acid sequences of each structural protein confirmed the initial observation that CedPV is most closely related to henipaviruses in the family. A phylogenetic tree based on the deduced sequences of the nucleocapsid protein (N) is presented in FIG. 3A. A phylogenetic tree analysis based on whole genome sequences gave similar results (FIG. 3B). Indeed, CedPV is more closely related to HeV and NiV than henipavirus-like sequences detected in African bats (26, 32) as shown in a phylogenetic tree based on the only sequences available of a 550-nt L gene fragment (FIG. 3C).

Example 3

First discovered for the parainfluenza virus 5 (PIV5, previously known as simian virus 5), almost all members of *Paramyxovirinae* have a P gene which produces multiple proteins through an RNA editing mechanism by addition of non-templated G residues leading to production of N-terminal co-linear proteins from different reading frames downstream from the editing site (3, 33). These multiple gene products are known to play a key role in antagonizing the innate response of susceptible hosts (3).

The CedPV genome codes for P protein of 737-aa and a C protein of 177-aa. PCR analysis, however, failed to find the highly conserved, cysteine-rich V protein ORF that is present in most other paramyxoviruses. The absence of the V protein ORF is attributed to the RNA editing site, with a sequence of AAAAGGG (e.g., nucleotides 5903-5909 of SEQ ID NO: 1) that is conserved in all other known HeV and NiV isolates discovered to date, is missing from the CedPV P gene sequence.

To verify that there are no multiple mRNAs produced from the CedPV P gene, direct sequencing of P gene transcripts was conducted from CedPV-infected Vero cells using multiple sets of primers generating overlapping fragments covering the entire coding region of the P gene. Briefly, quantitative PCR assays (qPCR) were established based on CedPV-specific sequences obtained from the high throughput sequencing. A TaqMan assay on the P gene was developed and used for all subsequent studies. The sequences of the primer/probe were as follows: forward primer, 5'-TGCAT TGAGC GAACC CATAT AC (SEQ ID NO: 14); reverse primer, 5'-GCACG CTTCT TGACA GAGTT GT (SEQ ID NO: 15); probe, 5'-TCCCG AGAAA CCCTC TGTGT TTGA-MGB (SEQ ID NO: 16).

Each produced uniform trace files indicating a lack of RNA editing activities, which is very different from the mixed peaks generated by HeV and NiV immediately after the editing site (FIG. 4). It appears that CedPV is the first-identified member of *Paramyxovirinae* that lacks both RNA editing and any V-related coding sequence in its P gene.

Example 4

The striking similarity in genome size and organization and the presence of highly conserved protein domains among the N, M and L proteins between CedPV and henipaviruses would indicate that CedPV may be antigenically related to HeV and/or NiV. To prepare antibodies directed against CedPV, the coding region for the CedPV N protein was amplified by PCR with a pair of primers flanked by AscI (5' end) and NotI (3' end) sites for cloning into a previously described GST-fusion expression vector (47). The expression and purification by gel elution was conducted as previously described (48). For antibody production, purified protein was injected subcutaneously into 4 different sites of 2 adult (at a dose of 100 μg per animal) New Zealand white female rabbits at days 0 and 27. A previously published triple adjuvant (49) was used for the immunization. Animals were checked for specific antibodies after days 5 and 42 and euthanized at day 69 for the final blood collection.

For immunofluorescence antibody test, Vero cell monolayers were prepared in 8-well chamber slides by seeding at a concentration of 30,000 cells/well in 300 μl of cell media and incubating over night at 37° C. The cell monolayers were infected with an MOI of 0.01 of CedPV, HeV or NiV and fixed with 100% ice-cold methanol at 24 hours post-infection. The chamber slides were blocked with 100 μl/well of 1% BSA in PBS for 30 min at 37° C. before adding 50 μl/well of rabbit sera against CedPV N or NiV N diluted 1:1000. After incubation at 37° C. for 30 min, the slides were washed three times in PBS-T and incubated with 50 μl/well of anti-rabbit 488 Alexafluore conjugate (Life Technologies) diluted 1:1000 at 37° C. for 30 min. The slides were then washed three times in PBS-T and mounted in 50% glycerol/PBS for observation under a fluorescence microscope.

For virus neutralization test, serial two-fold dilutions of sera were prepared in duplicate in a 96-well tissue culture plate in 50 μl cell media (Minimal Essential Medium containing Earle's salts and supplemented with 2 mM glutamine, antibiotic-antimycotic and 10% fetal calf serum). An equal volume containing 200 $TCID_{50}$ of target virus was added and the virus-sera mix incubated for 30 min at 37° C. in a humidified 5% $CO_2$ incubator. 100 μl of Vero cell suspension containing $2\times10^5$ cells/ml was added and the plate incubated at 37° C. in a humidified 5% $CO_2$ incubator. After 4 days, the plate was examined for viral CPE. The highest serum dilution generating complete inhibition of CPE was defined as the final neutralizing titer.

Staining of CedPV-infected Vero cells using rabbit anti-henipavirus antibodies indicated the presence of cross-reactivity. This cross-reactivity was further confirmed in reverse by staining of HeV-infected Vero cells using a rabbit serum raised against a recombinant CedPV N protein (FIG. 5). Analysis by virus neutralization test, however, found that henipavirus-neutralizing antibodies were unable to neutralize CedPV and vice versa. See also FIG. 6 which shows IFAT conducted with anti-CedPV serum on Vero cells infected with J paramyxovirus (JPV), Rinderpest virus (RPV), Sendai virus (SeV), Menangle virus (MenPV) and CedPV, respectively. Mock infected cell monolayer was included as a negative control Example 5

To further investigate the relationship between CedPV and recognized henipaviruses, CedPV's use of the ephrin-B2 and -B3 host cell proteins was examined. Typically, HeV and NiV use ephrin-B2 receptor as points of entry for infection for CedPV infection (22, 34). Human ephrin B2 and B3 genes were cloned into pQCXIH (Clontech) and the resulting plasmids packaged into retrovirus particles in the GP2-293 packaging cell line (Clontech) and pseudotyped with vesicular stomatitis virus G glycoprotein (VSV-G) following the manufacturer's instructions. HeLa-USU cell line (22) was infected with the VSV-G pseudotyped retrovirus particles in the presence of 1 μg/ml polybrene (Sigma). 8 hours post infection, the medium was changed and the cells were allowed to recover for 24 hours, which allows time for completion of the retroviral insert into the cellular genome and for expression of the hygromycin resistance gene.

24 hours post-infection, cells transformed by the retrovirus were selected for by the addition of 200 μg/ml hygromycin in the media. Stocks of cells that were resistant to hygromycin were prepared and frozen. HeLa-USU cells and ephrin-expressing HeLa-USU cells were seeded in 6-well tissue culture plates at a density of 250,000 cells/well overnight. The viruses (HeV and CedPV) were diluted to give an MOI of 0.01 and inoculated into the wells. The cell monolayers were examined daily for syncytial CPE.

For CedPV, similar observations were made with respect to the ephrin-B2 receptor. As shown in FIG. 7, CedPV failed to infect HeLa-USU, but was able to infect and cause syncytial CPE when the human ephrin-B2 gene was expressed. In contrast, when ephrin-B3 molecule was introduced, there was no evidence of infection.

Example 6

Ferrets, guinea pigs, and mice exhibit differing responses to HeV and NiV infections, with ferrets and guinea pigs, but not mice, developing severe disease characterized by systemic vasculitis (20, 35, 36, 37, 38). CedPV ($2\times10^6$ $TCID_{50}$/ml), which was passaged twice in bat PaKi cells, was administered to 2 male ferrets (1 ml oronasally), 4 female guinea pigs (1 ml intraperitoneally) and 5 female Balb-C mice (50 μl oronasally). Guinea pigs and mice were implanted with temperature sensing microchips (LifeChip Bio-Thermo®, Destron Fearing) and weighed daily. Ferret rectal temperature and weight was recorded at sampling times. Animals were observed daily for clinical signs of illness and were euthanized at 21 days post-inoculation. Sera were collected on days 10, 15 and 21 to test for neutralizing antibody against CedPV.

Based on the asymptomatic seroconversion to CedPV noted in the ferrets, 7 additional female ferrets were exposed by the oronasal route to a lower dose of $3\times10^3$ $TCID_{50}$. Two animals were euthanized on each of days 6, 8 and 10 post-inoculation and one on day 20. Nasal washes, oral swabs, and rectal swabs were collected on days 2, 4, 6, 8 and 10 and urine was sampled on the day of euthanazia. Each collected specimen was assessed for the CedPV genome. A wide range of tissue samples were collected at post mortem examination and assessed by routine histology, immunohistochemistry (using rabbit antibodies raised against recombinant CedPV and NiV N proteins, respectively), qPCR (see above) and virus isolation using reagents and procedures previously established (16).

In contrast to the response from exposure to NiV and HeV, the ferrets and guinea pigs exposed to CedPV remained clinically well, although neutralizing antibody was detected in serum between 10 to 21 days pi (Table 2). Balb-C mice exposed to CedPV also remained clinically well but did not develop neutralizing antibody in serum by day 21 pi. In ferrets electively euthanized at earlier time-points, there was reactive hyperplasia of tonsillar lymphoid tissue, retropharyngeal and bronchial lymph nodes, accompanied by edema and erythrophagocytosis. CedPV antigen was detected in bronchial lymph node of one animal euthanized on day 6 pi, consistent with viral replication in that tissue. Cross-reactive immunostaining against anti-NiV N protein antibodies was also noted (FIG. 8). No other significant histological lesions were identified.

TABLE 2

Antibody responses in CedPV-infected ferrets and guinea pigs

| Animal # | Days post inoculation | Neutralizing antibody titers CedPV | HeV |
|---|---|---|---|
| Ferret 1 | 0 | −ve | −ve |
| | 10 | 1:320 | −ve |
| | 15 | 1:640 | −ve |
| | 21 | 1:1280 | −ve |
| Ferret 2 | 0 | −ve | −ve |
| | 10 | 1:320 | −ve |
| | 15 | 1:640 | −ve |
| | 21 | 1:1280 | −ve |
| Guinea pig 1 | 0 | −ve | −ve |
| | 10 | −ve | −ve |
| | 21 | 1:80 | −ve |
| Guinea pig 2 | 0 | −ve | −ve |
| | 10 | −ve | −ve |
| | 21 | −ve | −ve |
| Guinea pig 3 | 0 | −ve | −ve |
| | 10 | −ve | −ve |
| | 21 | −ve | −ve |
| Guinea pig 4 | 0 | −ve | −ve |
| | 10 | −ve | −ve |
| | 21 | 1:160 | −ve |

Viral RNA was detected in selected lymphoid tissues of 3 of 4 ferrets sampled day 6 to 8 pi, including pharynx, spleen, and retropharyngeal and bronchial lymph nodes, as well as the submandibular lymph node of the ferret euthanized on day 20 pi. This pattern of lymphoid involvement suggests that there may be transient replication in the upper and lower respiratory tracts although CedPV genome was not recovered from nasal washes, oral swabs, pharynx or lung tissue of affected animals.

Example 7

Sera from 100 flying foxes collected during 2003-2005 from Queensland, Australia were screened for neutralizing antibodies to CedPV. Virus neutralization test was conducted as described above (antibody tests). All serum samples were tested at a dilution of 1:20. Due to the antigenic cross-reactivity observed between HeV and CedPV described above, virus neutralization tests were conducted to obtain more accurate infection data for each virus. Overall, 23% of the sera were CedPV-positive and 37% HeV-positive. Co-infection was reflected in 8% of the sera tested.

Example 8

The CedPV-G and F glycoproteins also represent an important system to explore the mapping of the henipavirus G and F functional domains. The CedPV-F is only 42% and 43% identical with HeV-F and NiV-F respectively; and CedPV-G is 29% and 30% identical with HeV-G and NiV-G. CedPV functional ephrin receptor usage was characterized along with heterotypic F and G coexpression and fusion assays using combinations of CedPV, HeV and NiV. Codon optimized clones were prepared in a pCDNA vector and tagged for detection with the S-peptide tag. Both constructs have been expressed, detected, and found to be functional in our reporter gene cell-cell fusion assay. A pilot assay (FIG. 9) indicates this feasibility of this approach. Ephrin-B2 and -B3 negative HeLa-USU cells are negative CedPV cell-cell fusion, as has the ephrin-B3 expressing cell line Hela-B3.

Fusion is observed with 293T target cells and ephrin-B2 expressing HeLa-B2 cell line. Importantly, CedPV-F has heterotypic function with both HeV-G and NiV-G, but further; CedPV-G has heterotypic function only with HeV-F and not NiV-F (FIG. 9) and also correlates with ephrin use.

Example 9

Significant detail is available for the binding between HeV and NiV-G and either ephrin-B2 or -B3 Mutations in G can render it non-functional in fusion promotion activity and virus infectivity, while retaining ephrin receptor binding ability, at locations in the stalk or globular head. In a co-ip assay with the 3 sG proteins (HeV, NiV and CedPV) along with a series of ephrin receptors it was observed that CedPV-sG is able to bind multiple ephrin subtypes including: B1, B2, B3-weak, A1, A2, A4-weak, and A5 (FIG. 10). This remarkably wide receptor binding profile is in sharp contrast to NiV and HeV-G which bind only ephrin-B2 and -83.

Example 10

A pilot cell-cell fusion experiment using a HeLa-USU target cell will the various ephrin receptor constructs transfected and expressed is shown in FIG. 11. Hela-USU target cell populations were prepared by transfecting in the indicated ephrin receptor constructs and then used in cell-cell fusion assay with effector cells expressing either CedPV, HeV or NiV F and G glycoproteins, and a standard fusion-reporter gene assay was carried out. CedPV G and F mediated fusion was highly permissive when either ephrin A1 or A2; or ephrin B1 or B2 was utilized; whereas we know that HeV and NiV make use of only ephrin B2 and B3.

Further, the background endogenous levels of ephrin A1 (based on gene array data) in the Hela-USU cells is the cause of the fusion signal in untransfected cells. The results of this experiment indicate the ephrin receptor binding data with CedPV G glycoprotein (FIG. 10) correlates well with CedPV receptor binding and functional cell-cell fusion carried out in vitro. A summary of the ephrin receptor binding and fusion data obtained so far is shown in Table 3 below.

| Ephrin | Binding | Fusing |
|---|---|---|
| A1 | + | + |
| A2 | + | + |
| A3 | − | − |
| A4 | +/− | − |
| A5 | + | |
| B1 | + | + |
| B2 | + | + |
| B3 | +/− | − |

The following references are referred to herein by number and are incorporated by reference in their entirety.

1. Murray K, Selleck P, Hooper P, Hyatt A, Gould A, et al. (1995) A morbillivirus that caused fatal disease in horses and humans. Science 268: 94-97.
2. Chua K B, Bellini W J, Rota P A, Harcourt B H, Tamin A, et al. (2000) Nipah virus: a recently emergent deadly paramyxovirus. Science 288: 1432-1435.
3. Lamb R A, Parks G D (2007) *Paramyxoviridae*: The viruses and their replication. In: Knipe D M, Griffin D E, Lamb R A, Straus S E, Howley P M et al., editors. Fields Virology. Philadelphia: Lippincott Williams & Wilkins. pp. 1449-1496.
4. Eaton B T, Broder C C, Middleton D, Wang L F (2006) Hendra and Nipah viruses: different and dangerous. Nat Rev Microbiol 4: 23-35.
5. Pallister J, Middleton D, Broder C C, Wang L-F (2011) Henipavirus vaccine development. Journal of Bioterrorism and Biodefense: S1:005.
6. Eaton B T, Mackenzie J S, Wang L-F (2007) Henipaviruses. In: Knipe D M, Griffin D E, Lamb R A, Straus S E, Howley P M et al., editors. Fields Virology. Philadelphia: Lippincott Williams & Wilkins. pp. 1587-1600.
7. Yob J M, Field H, Rashdi A M, Morrissy C, van der Heide B, et al. (2001) Nipah virus infection in bats (order Chiroptera) in peninsular Malaysia. Emerg Infect Dis 7: 439-441.
8. Li Y, Wang J, Hickey A C, Zhang Y, Li Y, et al. (2008) Antibodies to Nipah or Nipah-like viruses in bats, China. Emerg Infect Dis 14: 1974-1976.
9. Hayman D T, Suu-Ire R, Breed A C, McEachern J A, Wang L, et al. (2008) Evidence of henipavirus infection in West African fruit bats. PLoS One 3: e2739.
10. Halpin K, Hyatt A D, Fogarty R, Middleton D, Bingham J, et al. (2011) Pteropid Bats are Confirmed as the Reservoir Hosts of Henipaviruses: A Comprehensive Experimental Study of Virus Transmission. Am J Trop Med Hyg 85: 946-951.
11. Leroy E M, Kumulungui B, Pourrut X, Bouquet P, Hassanin A, et al. (2005) Fruit bats as reservoirs of Ebola virus. Nature 438: 575-576.
12. Towner J S, Pourrut X, Albarino C G, Nkogue C N, Bird B H, et al. (2007) Marburg virus infection detected in a common African bat. PLoS ONE 2: e764.
13. U W, Shi Z, Yu M, Ren W, Smith C, et al. (2005) Bats are natural reservoirs of SARS-like coronaviruses. Science 310: 676-679.
14. Chua K B, Crameri G, Hyatt A, Yu M, Tompang M R, et al. (2007) A previously unknown reovirus of bat origin is associated with an acute respiratory disease in humans. Proc Natl Acad Sci USA 104: 11424-11429.
15. Weingartl H M, Berhane Y, Caswell J L, Loosmore S, Audonnet J C, et al. (2006) Recombinant Nipah virus vaccines protect pigs against challenge. J Virol 80: 7929-7938.

16. Mungall B A, Middleton D, Crameri G, Bingham J, Halpin K, et al. (2006) Feline model of acute Nipah virus infection and protection with a soluble glycoprotein-based subunit vaccine. J Virol 80: 12293-12302.

17. McEachern J A, Bingham J, Crameri G, Green D J, Hancock T J, et al. (2008) A recombinant subunit vaccine formulation protects against lethal Nipah virus challenge in cats. Vaccine 26: 3842-3852.

18. Pallister J, Middleton D, Wang L F, Klein R, Haining J, et al. (2011) A recombinant Hendra virus G glycoprotein-based subunit vaccine protects ferrets from lethal Hendra virus challenge. Vaccine 29: 5623-5630.

19. Bossart K N, Geisbert T W, Feldmann H, Zhu Z, Feldmann F, et al. (2011) A neutralizing human monoclonal antibody protects african green monkeys from hendra virus challenge. Sci Transl Med 3: 105ra103.

20. Bossart K N, Zhu Z, Middleton D, Klippel J, Crameri G, et al. (2009) A neutralizing human monoclonal antibody protects against lethal disease in a new ferret model of acute Nipah virus infection. PLoS Pathog 5: e1000642.

21. Bossart K N, McEachern J A, Hickey A C, Choudhry V, Dimitrov D S, et al. (2007) Neutralization assays for differential henipavirus serology using Bio-Plex Protein Array Systems. J Virol Methods 142: 29-40.

22. Bonaparte M I, Dimitrov A S, Bossart K N, Crameri G, Mungall B A, et al. (2005) Ephrin-B2 ligand is a functional receptor for Hendra virus and Nipah virus. Proc Natl Acad Sci USA 102: 10652-10657.

23. Negrete O A, Levroney E L, Aguilar H C, Bertolotti-Ciarlet A, Nazarian R, et al. (2005) EphrinB2 is the entry receptor for Nipah virus, an emergent deadly paramyxovirus. Nature 436: 401-405.

24. Negrete O A, Wolf M C, Aguilar H C, Enterlein S, Wang W, et al. (2006) Two key residues in ephrinB3 are critical for its use as an alternative receptor for Nipah virus. PLoS Pathog 2: e7.

25. Guillaume V, Contamin H, Loth P, Georges-Courbot M C, Lefeuvre A, et al. (2004) Nipah virus: vaccination and passive protection studies in a hamster model. J Virol 78: 834-840.

26. Drexler J F, Corman V M, Gloza-Rausch F, Seebens A, Annan A, et al. (2009) Henipavirus RNA in African bats. PLoS ONE 4: e6367.

27. Crameri G, Todd S, Grimley S, McEachern J A, Marsh G A, et al. (2009) Establishment, immortalisation and characterisation of pteropid bat cell lines. PLoS ONE 4: e8266.

28. Chua K B, Wang L F, Lam S K, Crameri G, Yu M, et al. (2001) Tioman virus, a novel paramyxovirus isolated from fruit bats in malaysia. Virology 283: 215-229.

29. Chua K B, Lek Koh C, Hooi P S, Wee K F, Khong J H, et al. (2002) Isolation of Nipah virus from Malaysian Island flying-foxes. Microbes Infect 4: 145-151.

30. Chua K B (2003) A novel approach for collecting samples from fruit bats for isolation of infectious agents. Microbes Infect 5: 487-490.

31. Tong S, Chern S W, Li Y, Pallansch M A, Anderson U (2008) Sensitive and broadly reactive reverse transcription-PCR assays to detect novel paramyxoviruses. J Clin Microbiol 46: 2652-2658.

32. Baker K S, Todd S, Marsh G, Fernandez-Loras A, Suu-Ire R, et al. (2012) Co-circulation of diverse paramyxoviruses in an urban African fruit bat population. 1 Gen Virol 93: 850-856.

33. Thomas S M, Lamb R A, Paterson R G (1988) Two mRNAs that differ by two nontemplated nucleotides encode the amino coterminal proteins P and V of the paramyxovirus SV5. Cell 54: 891-902.

34. Bossart K N, Tachedjian M, McEachern J A, Crameri G, Zhu Z, et al. (2008) Functional studies of host-specific ephrin-B ligands as Henipavirus receptors. Virology 372: 357-371.

35. Pallister J, Middleton D, Crameri G, Yamada M, Klein R, et al. (2009) Chloroquine administration does not prevent Nipah virus infection and disease in ferrets. J Virol 83: 11979-11982.

36. Williamson M M, Hooper P T, Selleck P W, Westbury H A, Slocombe R F (2000) Experimental hendra virus infectionin pregnant guinea-pigs and fruit Bats (*Pteropus poliocephalus*). J Comp Pathol 122: 201-207.

37. Westbury H A, Hooper P T, Selleck P W, Murray P K (1995) Equine morbillivirus pneumonia: susceptibility of laboratory animals to the virus. Aust Vet J 72: 278-279.

38. Wong K T, Grosjean I, Brisson C, Blanquier B, Fevre-Montange M, et al. (2003) A golden hamster model for human acute Nipah virus infection. Am J Pathol 163: 2127-2137.

39. Negredo A (2011) Discovery of an ebolavirus-like filovirus in Europe. PLoS Pathogens 7: e1002304.

40. Lamb R A, Collins P L, Kolakofsky D, Melero J A, Nagai Y, et al. (2005) Family Paramyxoviridae. In: Fauquet C M, Mayo J, Maniloff J, Desselberger U, Ball L A, editors. Virus Taxonomy: 8th Report of the International Comittee on Taxonomy of Viruses. San Diego: Elsevier Academic Press. pp. 655-668.

41. Chambers R, Takimoto T (2009) Antagonism of innate immunity by paramyxovirus accessory proteins. Viruses 1: 574-593.

42. Matsuoka Y, Curran J, Pelet T, Kolakofsky D, Ray R, et al. (1991) The P gene of human parainfluenza virus type 1 encodes P and C proteins but not a cysteine-rich V protein. J Virol 65: 3406-3410.

43. Margulies M, Egholm M, Altman W E, Attiya S, Bader J S, et al. (2005) Genome sequencing in microfabricated high-density picolitre reactors. Nature 437: 376-380.

44. Palacios G, Quan P L, Jabado O J, Conlan S, Hirschberg D L, et al. (2007) Panmicrobial oligonucleotide array for diagnosis of infectious diseases. Emerg Infect Dis 13: 73-81.

45. Li Z, Yu M, Zhang H, Wang H Y, Wang L F (2005) Improved rapid amplification of cDNA ends (RACE) for mapping both the 5' and 3' terminal sequences of paramyxovirus genomes. J Virol Methods 130: 154-156.

46. Tamura K, Dudley J, Nei M, Kumar S (2007) MEGA4: Molecular Evolutionary Genetics Analysis (MEGA) software version 4.0. Mol Biol Evol 24: 1596-1599.

47. Wang L F, Yu M, White J R, Eaton B T (1996) BTag: a novel six-residue epitope tag for surveillance and purification of recombinant proteins. Gene 169: 53-58.

48. Wang L F, Gould A R, Selleck P W (1997) Expression of equine morbillivirus (EMV) matrix and fusion proteins and their evaluation as diagnostic reagents. Arch Virol 142: 2269-2279.

49. Prowse S (2000) A new adjuvant. ANZCCART News 13: 7.

What is claimed is:

1. An immunogenic composition comprising a soluble Cedar virus (CedPV) glycoprotein selected from a soluble CedPV F glycoprotein, a soluble CedPV G glycoprotein, and a combination thereof, in an amount effective to produce an immune response in a human subject, and a pharmaceutically acceptable carrier.

2. The immunogenic composition of claim 1, further comprising one or more CedPV proteins selected from N-protein, P-protein, M-protein, and L-protein of Cedar virus.

3. The immunogenic composition of claim 2, wherein the composition comprises a soluble CedPV F glycoprotein.

4. The immunogenic composition of claim 2, wherein the composition comprises a soluble CedPV G glycoprotein.

5. The immunogenic composition of claim 1, wherein the composition comprises a soluble CedPV glycoprotein encoded by a Cedar virus genome comprising the nucleotide sequence of SEQ ID NO: 1 or a fragment thereof.

6. The immunogenic composition of claim 1, further comprising an adjuvant.

7. The immunogenic composition of claim 1, wherein the composition is formulated for a route of administration selected from the group consisting of orally, intravenously, subcutaneously, intraarterially, intramuscularly, intracardially, intraspinally, intrathoracically, intraperitoneally, intraventricularly, sublingually, and transdermally.

8. The immunogenic composition of claim 1, wherein the composition comprises a soluble CedPV F glycoprotein.

9. The immunogenic composition of claim 1, wherein the composition comprises a soluble CedPV G glycoprotein.

10. The immunogenic composition of claim 1, wherein the composition comprises a soluble CedPV F glycoprotein and a soluble CedPV G glycoprotein.

11. The immunogenic composition of claim 1, wherein the composition comprises a soluble F glycoprotein consisting of amino acids 1-490 of SEQ ID NO: 6.

12. The immunogenic composition of claim 1, wherein the composition comprises a soluble G glycoprotein consisting of amino acids 87-622 of SEQ ID NO: 7.

* * * * *